United States Patent
Franklin et al.

(10) Patent No.: US 9,439,416 B2
(45) Date of Patent: Sep. 13, 2016

(54) COMPOSITIONS AND METHODS COMPRISING TERPENES OR TERPENE MIXTURES SELECTED FROM THYMOL, EUGENOL, GERANIOL, CITRAL, AND L-CARVONE

(75) Inventors: Lanny Franklin, Atlanta, GA (US); Elizabeth Cloud, legal representative, Houston, TX (US); Lanna Knapp, legal representative, Atlanta, GA (US); Gary Ostroff, Worcester, MA (US)

(73) Assignee: Eden Research PLC (GB)

( * ) Notice: Subject to any disclaimer, the term of this patent is extended or adjusted under 35 U.S.C. 154(b) by 1021 days.

(21) Appl. No.: 12/095,580

(22) PCT Filed: Aug. 3, 2006

(86) PCT No.: PCT/GB2006/002881
§ 371 (c)(1),
(2), (4) Date: Jul. 23, 2009

(87) PCT Pub. No.: WO2007/063268
PCT Pub. Date: Jun. 7, 2007

(65) Prior Publication Data
US 2010/0272818 A1    Oct. 28, 2010

Related U.S. Application Data

(60) Provisional application No. 60/741,167, filed on Nov. 30, 2005.

(51) Int. Cl.
| | | |
|---|---|---|
| A61K 9/50 | (2006.01) |
| A61K 31/11 | (2006.01) |
| A01N 35/02 | (2006.01) |
| A61K 31/085 | (2006.01) |
| A01N 31/16 | (2006.01) |
| A01N 25/08 | (2006.01) |
| A01N 31/02 | (2006.01) |
| A01N 31/08 | (2006.01) |
| A01N 35/06 | (2006.01) |
| A01N 31/14 | (2006.01) |
| A01N 35/04 | (2006.01) |

(52) U.S. Cl.
CPC ............... *A01N 25/08* (2013.01); *A01N 31/02* (2013.01); *A01N 31/08* (2013.01); *A01N 31/14* (2013.01); *A01N 31/16* (2013.01); *A01N 35/02* (2013.01); *A01N 35/04* (2013.01); *A01N 35/06* (2013.01)

(58) Field of Classification Search
USPC ......... 424/493, 405, 490; 514/703, 720, 731
See application file for complete search history.

(56) References Cited

U.S. PATENT DOCUMENTS

| | | | |
|---|---|---|---|
| 3,499,765 A | 3/1970 | Lendvay | |
| 3,767,421 A | 10/1973 | Gulstad et al. | |
| 3,956,485 A | 5/1976 | Willett et al. | |
| 4,001,480 A | 1/1977 | Shank | |
| 4,032,551 A | 6/1977 | Willett et al. | |
| 4,049,828 A | 9/1977 | Cole et al. | |
| 4,310,554 A | 1/1982 | Olson et al. | |
| 4,534,983 A | 8/1985 | Koene et al. | |
| 4,611,608 A | 9/1986 | Vos et al. | |
| 4,617,945 A | 10/1986 | Vos et al. | |
| 4,696,863 A | 9/1987 | Matsushita | 428/402.2 |
| 4,743,620 A | 5/1988 | Hodgin et al. | |
| 4,810,646 A | 3/1989 | Jamas et al. | |
| 4,826,693 A | 5/1989 | Smith et al. | |
| 4,944,693 A | 7/1990 | Puerner et al. | |
| 4,963,583 A | 10/1990 | Kunz et al. | |
| 4,985,261 A | 1/1991 | Kang et al. | |
| 4,992,540 A | 2/1991 | Jamas et al. | |
| 5,001,155 A | 3/1991 | Kuc et al. | |
| 5,028,703 A * | 7/1991 | Jamas et al. | 536/114 |
| 5,068,453 A | 11/1991 | Kuwahara et al. | |
| 5,078,904 A | 1/1992 | Behan et al. | |
| 5,082,936 A | 1/1992 | Jamas et al. | |
| 5,091,200 A | 2/1992 | Kang et al. | |
| 5,288,632 A | 2/1994 | Pannell | |
| 5,401,727 A | 3/1995 | Rorstad et al. | |
| 5,547,677 A | 8/1996 | Wright et al. | |
| 5,549,901 A | 8/1996 | Wright et al. | |

(Continued)

FOREIGN PATENT DOCUMENTS

| | | |
|---|---|---|
| AP | P/2006/003724 | 1/2005 |
| AP | P/2008/004524 | 8/2006 |

(Continued)

OTHER PUBLICATIONS

Abegaz, B. M. Polyacetylenic thiophenes and terpenoids from the roots of Echinops pappii. Phytochemistry. 30(3):879-881. Abstract.
Abid, M., Sultan, V., Zaki, M. J., Maqbool, M. A. 1997. Nematicidal properties of Stoechospermum marginatum, a seaweed. Pakistan Journal of Phytopathology:9(2):143-147. Abstract.
Aikawa, T., Togashi, K. 1999. An effect of pine volatiles on departure of Bursaphelenchus xylophilus (Nematoda: aphelenchoididae) from Monochamus alternatus (Coleoptera: Cerambycidae). pp. 127-131 in Sustainability of pine forests in relation to pine wilt and decline. Proceedings of International Symposium, Tokyo, Japan, Oct. 27-28, 1998 Abstract.

(Continued)

*Primary Examiner* — Anna Falkowitz
(74) *Attorney, Agent, or Firm* — Akerman LLP

(57) ABSTRACT

The present invention relates to compositions comprising terpenes which are particularly suitable for treating plant infections, to methods of making such compositions, and to methods of using them. The present invention also relates to compositions comprising terpenes and hollow glucan particles or cell wall particles and methods for preparing such compositions; such compositions increase terpene stability and activity and provide a suitable carrier for the terpenes. The invention also relates to methods of using such compositions in the medical, veterinary and agricultural fields. In particular, the terpenes disclosed are thymol, eugenol, geraniol, citral and L-carvone.

22 Claims, 9 Drawing Sheets

(56) References Cited

U.S. PATENT DOCUMENTS

| | | |
|---|---|---|
| 5,607,677 A | 3/1997 | Jamas et al. |
| 5,618,840 A | 4/1997 | Wright et al. |
| 5,622,548 A | 4/1997 | Zou et al. |
| 5,629,021 A | 5/1997 | Wright et al. |
| 5,662,915 A | 9/1997 | Okioga et al. |
| 5,662,957 A | 9/1997 | Wright et al. |
| 5,673,468 A | 10/1997 | Pumpe et al. |
| 5,700,679 A | 12/1997 | Wright et al. |
| 5,730,989 A | 3/1998 | Wright |
| 5,756,136 A | 5/1998 | Black et al. |
| 5,798,252 A | 8/1998 | Hobson et al. |
| 5,849,956 A | 12/1998 | Koga et al. |
| 5,919,838 A | 7/1999 | Mizobuchi |
| 5,922,121 A | 7/1999 | Kwan |
| 5,939,050 A | 8/1999 | Iyer et al. |
| 5,977,186 A | 11/1999 | Franklin et al. |
| 5,981,625 A | 11/1999 | Zou et al. |
| 6,130,253 A | 10/2000 | Franklin et al. |
| 6,187,439 B1 | 2/2001 | Elwakil |
| 6,232,528 B1 | 5/2001 | Scorza et al. |
| 6,242,594 B1 | 6/2001 | Kelly et al. |
| 6,261,540 B1 | 7/2001 | Nelson |
| 6,306,450 B1 | 10/2001 | Bank et al. |
| 6,444,448 B1 | 9/2002 | Wheatcroft .................. 435/101 |
| 6,465,640 B1 | 10/2002 | Hood |
| 6,506,803 B1 | 1/2003 | Baker, Jr. et al. |
| 6,524,998 B1 | 2/2003 | Kloepper et al. |
| 6,534,078 B1 | 3/2003 | Strzemiemski et al. |
| 6,723,358 B1 | 4/2004 | van Lengerich et al. |
| 6,746,684 B2 | 6/2004 | Kitagaki .................. 424/419 |
| 6,849,276 B1 | 2/2005 | Dufau et al. |
| 6,887,493 B2 | 5/2005 | Shefer et al. |
| 7,018,641 B1 | 3/2006 | Momol et al. |
| 2003/0180349 A1* | 9/2003 | Franklin .................. 424/450 |
| 2003/0185956 A1 | 10/2003 | Gradley |
| 2003/0191046 A1 | 10/2003 | Krzysztof |
| 2003/0194454 A1 | 10/2003 | Bessette et al. |
| 2003/0216488 A1 | 11/2003 | Uchiyama et al. |
| 2003/0228402 A1 | 12/2003 | Franklin et al. |
| 2003/0231978 A1* | 12/2003 | Franklin et al. ................ 422/4 |
| 2004/0022990 A1 | 2/2004 | Sitabkhan |
| 2004/0054166 A1 | 3/2004 | Sauter et al. ........... 536/123.12 |
| 2004/0096821 A1 | 5/2004 | Keenan et al. |
| 2004/0248764 A1 | 12/2004 | Franklin .......................... 514/1 |
| 2005/0126908 A1 | 6/2005 | Keenan et al |
| 2006/0120974 A1 | 6/2006 | Mcneight et al. |
| 2006/0127489 A1 | 6/2006 | Crothers et al. |
| 2006/0165614 A1 | 7/2006 | Nelson et al. |
| 2008/0220038 A1 | 9/2008 | Franklin .................. 422/417 |
| 2010/0040656 A1* | 2/2010 | Franklin et al. ............. 424/405 |
| 2010/0136102 A1 | 6/2010 | Franklin .................. 424/451 |
| 2014/0170198 A1 | 6/2014 | Franklin .................. 424/493 |

FOREIGN PATENT DOCUMENTS

| | | |
|---|---|---|
| AU | 2002323473 | 8/2002 |
| AU | 2005207622 | 1/2005 |
| AU | 2005245190 | 5/2005 |
| AU | 2006321415 | 8/2006 |
| AU | 2006321416 | 8/2006 |
| CA | 2141761 A | 2/1996 |
| CA | 2 382 740 A1 | 8/2000 |
| CA | 2567333 | 5/2005 |
| CN | 20058002451.X | 5/2005 |
| DE | 197 20 604 A1 | 5/1997 |
| EP | 0085805 * | 8/1983 ............ C12N 1/00 |
| EP | 0242135 * | 10/1987 ............ B01J 13/02 |
| EP | 0414282 | 2/1991 |
| EP | 0414283 | 2/1991 |
| EP | 0460945 | 12/1991 |
| EP | 0528466 | 2/1993 |
| EP | 0 819 759 A1 | 1/1998 |
| EP | 0844909 | 6/1998 |
| EP | 0913407 | 5/1999 |
| EP | 1085812 | 3/2001 |
| EP | 1106070 | 6/2001 |
| EP | 1159882 A2 | 12/2001 |
| EP | 1161878 | 12/2001 |
| EP | 1161883 | 12/2001 |
| EP | 2002757456 | 8/2002 |
| EP | 1240380 | 9/2002 |
| EP | 1413202 | 4/2004 |
| EP | 2005708211 | 1/2005 |
| EP | 2005744354 | 5/2005 |
| EP | 1538197 A1 | 6/2005 |
| EP | 2006765189 | 8/2006 |
| EP | 2006765192 | 8/2006 |
| GB | 1285244 | 8/1972 |
| GB | 1362007 | 7/1974 |
| GB | 1457098 | 12/1976 |
| GB | 1513777 | 6/1978 |
| GB | 2162147 | 1/1986 |
| GB | 2394416 | 4/2004 |
| GB | 2395124 | 5/2004 |
| GB | 2396107 | 6/2004 |
| GB | 2406053 | 3/2005 |
| IN | 7201/DELNP/2006 | 5/2005 |
| IN | 5081/DELNP/2008 | 8/2006 |
| JP | 55064736 | 5/1980 |
| JP | 591 268 75 | 6/1984 |
| JP | 62294079 | 12/1987 |
| JP | 632 994 49 | 11/1988 |
| JP | 02067208 | 3/1990 |
| JP | 0219 1961 | 7/1990 |
| JP | 03212497 | 9/1991 |
| JP | 06-116111 | 4/1994 |
| JP | 8-243378 | 9/1996 |
| JP | 9-67205 | 3/1997 |
| JP | 200044878 | 2/2000 |
| JP | 2000 139 051 | 5/2000 |
| JP | 02027903 | 1/2002 |
| JP | 04024042 | 1/2004 |
| JP | 2007517431 | 5/2005 |
| JP | 2008542816 | 8/2006 |
| JP | 2008542817 | 8/2006 |
| MX | PA/a/2004/001906 | 8/2002 |
| MX | PA/a/2006/013420 | 5/2005 |
| MX | MX/a/2008/0006927 | 8/2006 |
| NZ | 531492 | 8/2002 |
| NZ | 551644 | 5/2005 |
| PH | 12006502324 | 5/2005 |
| WO | WO 92/10946 | 9/1990 |
| WO | WO 91/10772 | 7/1991 |
| WO | WO 91/17741 | 11/1991 |
| WO | WO 94/09653 | 5/1994 |
| WO | WO 96/36433 | 11/1996 |
| WO | WO 96/38055 | 12/1996 |
| WO | WO 98/56340 | 12/1998 |
| WO | WO 99/30691 | 6/1999 |
| WO | WO 00/21364 | 4/2000 |
| WO | WO 00/24259 | 5/2000 |
| WO | WO 00/49865 | 8/2000 |
| WO | WO 00/51435 | 9/2000 |
| WO | WO 00/53020 | 9/2000 |
| WO | WO 01/11006 | 2/2001 |
| WO | WO 01/13727 A1 | 3/2001 |
| WO | WO 02/02213 | 1/2002 |
| WO | WO 02/012348 | 2/2002 |
| WO | WO 02/056879 | 7/2002 |
| WO | WO 02/085314 | 10/2002 |
| WO | WO-03/020024 | 3/2003 |
| WO | WO 03/020024 | 3/2003 |
| WO | WO 03/028451 | 4/2003 |
| WO | WO 03/069993 | 8/2003 |
| WO | WO 03/070286 | 8/2003 |
| WO | WO 03/089561 | 10/2003 |
| WO | W02004034791 | 4/2004 |
| WO | WO 2004/037004 | 5/2004 |
| WO | WO 2004/037232 | 5/2004 |
| WO | WO 2004/045588 | 6/2004 |
| WO | WO 2004/084947 | 10/2004 |
| WO | WO-2005/070213 | 8/2005 |
| WO | WO 2005/070213 | 8/2005 |
| WO | WO 2005/102045 | 11/2005 |

(56) References Cited

FOREIGN PATENT DOCUMENTS

| WO | WO 2005/102508 | 11/2005 |
|---|---|---|
| WO | WO 2005/104842 | 11/2005 |
| WO | WO 2005/113128 | 12/2005 |
| WO | WO-2005/113128 | 12/2005 |
| WO | WO 2006/100308 | 9/2006 |
| WO | WO-2007/063267 | 6/2007 |
| WO | WO 2007/063267 | 6/2007 |
| WO | WO-2007/063268 | 6/2007 |
| ZA | 200402367 | 8/2002 |
| ZA | 200610427 | 5/2005 |

OTHER PUBLICATIONS

Akao N, Goto Y, Kondo K, Tsuda Y. Changing chemosusceptibility in the second-stage larvae of Toxocara canis by long-term incubation. J Helminthol. Jun. 1993;67(2):145-50. Abstract.

Asakawa, Y. 1999. Phytochemistry of bryophytes. Biologically active terpenoids and aromatic compounds from liverworts. Ed. Romeo, J. T. pp. 319-342 in Phytochemicals in human health protection, nutrition, and plant defense. Kluwer Academic/Plenum Publishe.

Bae et al. 1998. Anti-Helicobacter pylori activity of herbal medicines. Biol. Pharm. Bull., 21(9) 990-992.

Bard et al. 1988. Geraniol interferes with membrane functions in strains of Candida and Saccharomyces. Lipids 23(6):534-538.

Bauske EM; Rodriguezkabana R; Estaun V; Kloepper JW; Robertson DG; Weaver CF; King PS. 1995. Management of Meloidogyne-Incognita on Cotton by use of Botanical Aromatic-Compounds. Nematropica 24: 143-150. Abstract.

Bauske, E. M., Backman, P. A., Harper, K. M., Brannen, P. M., Rodriguez-Kabana, R., Kloepper, J. W. 1997. Effect of botanical aromatic compounds and seed-surface pH on growth and colonization of cotton plant growth-promoting rhizobacteria. Biocontrol Science and Technology Abstract.

Bertaccini et al., "Lee and Chiykowski, 1963 Infectivity of Aster Yellows Virus Preparations After Differential Centrifugations of Extract From Viruliferous Leafhoppers," Virol. 21: 667-669, 1992.

Blagburn, B. L. 2002. Changing trends in ectoparasite control. Eds. Thoday, K. L., Foil, C. S., Bond, R. pp. 59-68. Abstract.

Borris, R. P., Schaeffer, J. M. Antiparasitic agents from plants. 1992. pp. 117-158 in Phytochemical resources for medicine and agriculture. Eds. Nigg, H.N.; Seigler, D. Plenum Press, New York. Abstract.

Chaumont J. P. and D. Leger, "Campaign Against Allergic Moulds in Dwellings, Inhibitor Properties of Essential Oil Geranium Bourbon,Citronellol, Geraniol and Citral," Ann. Pharm. Fr. 50 (3): 156-166, 1992.

Chavarria-Carvajal, Jose A. 1997. Use of Organic Amendments and Naturally Occurring Aromatic Compounds for Control of Plant-Parasitic Nematodes: Effects on Microbial Activity and Soil Enzymes (Meloidogyne Incognita, Phytonematodes, Benzaldehyde, Biologic Control, 58-07B:3397 Abstract.

Chitwood DJ. Phytochemical based strategies for nematode control. Annu Rev Phytopathol. 2002;40:221-49. Abstract.

Chitwood, D. J. 1993. Naturally occurring nematicides. Eds. Duke, S. O., Menn, J. J., Plimmer, J. R. pp. 300-315 in Pest control with enhanced environmental safety. American Chemical Society (ACS), Washington. Abstract.

Crowell et al., "Antitumorigenic Effects of Limonen and Perillyl Alcohol Against Pancreatic and Breast Cancer," Adv. Exp. Med. Biol. 401:131-136, 1996.

Crowell, P. L. and Gould, M. N., "Chemoprevention and Therapy of Cancer by D-Limonene," Crit. Rev. Oncog. 5 (1):1-22, 1994.

Database WPI/Derwent, AN 1981-56184D [25], XP-002297964 (Abstract).

Database WPI/Derwent, AN 1981-56187D [31], XP-002297963 (Abstract).

Database WPI/Derwent, AN 198156193D [31], XP-002297962 (Abstract).

Database WPI/Derwent, AN 1985-047717 [08] and JP 19830113680 19830624 XP-002297961 (Abstract).

Database WPI/Derwent, AN 1986-052832 [08] and JP 19840126875 19840620 XP-002297960 (Abstract).

Database WPI/Derwent, AN 1986-207139 [25] and JP 19840259347 19841210 XP-002297959 (Abstract).

Database WPI/Derwent, AN 1990-214404 [28] and JP 19880299449 19881129 XP-002297958 (Abstract).

Database WPI/Derwent, AN 1992-045981 [06] and JP 19900191961 19900720, XP-002297957 (Abstract).

Database WPI/Derwent, AN 1999-114787 [10] and JP 19970148744 19970606, XP-002297956 (Abstract).

Database WPI/Derwent, AN 2002-262398 [31] and JP 20000139051 20000511, XP-002297955 (Abstract).

Database WPI/Derwent, AN 93-216621 and JP 910335687 911125, XP-002056937 (Abstract).

Deeley et al., "Use of Dienes' Stain to Detect Plant Diseases Induced by MIOs," Phytopathology. 69: 1169-1171, 1979.

Duke, S. O. 1991. Plant terpenoids as pesticides. pp. 269-296 in Handbook of natural toxins. vol. 6. Toxicology of plant and fungal compounds. Eds. Keeler, R.F.; Tu, A.T. Marcel Dekker, Inc., New York. Abstract.

Eden-Green "Culture of Other Microorganisms From Yellows-Diseased Plants,"pp. 201-239. In M. J. D. A. P. G. Markham (Ed.), "Plant and Insect Mycoplasma Techniques." Croom and Helm, London. 1982.

Elegbede et al., Regression of rat primary mammary tumors following dietary d-limonene. J Natl Cancer Inst 76(2):323-325, 1986.

Elgebede et al., "Inhibition of DMBA-Induced Mammary Cancer by Monoterpene D- Limonene," Carcinogensis 5 (5): 661-664, 1984.

Elson C. E. and Yu, S. G., "The Chemoprevention of Cancer by Mevalonate-Derived Constituents of Fruits and Vegetables," J. Nutr. 124: 607-614, 1994.

Enwerem, N. M., Okogun, J. I., Wambebe, C. O., Okorie, D. A., Akah, P. A.. 2001. Anthelmintic activity of the stem bark extracts of Berlinia grandiflora and one of its active principles, betulinic acid. Phytomedicine 8(2):112-114. Abstract.

Estaun, V., Camprubi, A., Calvet, C., Pinochet, J., Rodriguez-Kabana, R. 2001. Evaluation of natural chemical compounds against root-lesion and root-knot nematodes and side-effects on the infectivity of arbuscular mycorrhizal fungi. European Journal of P.

Firman, K., Kinoshita, T., Itai, A., Sankawa, U. 1988. Terpenoids from Curcuma heyneana. Phytochemistry. 27(12):3887-3891. Abstract.

Gunderson and Lee, "Ultrasensitive Detection of Phytoplasmas by Nested-PCR Assays Using Two Universal Primer Pairs," Phytopath. Medit. 35:144-151, 1996.

Gunderson et al., "Genomic Diversity and Differentiation Among Phytoplasma Strains in 16S rRNA Groups I (Aster Yellows and Related Phytoplasmas) and III (X-Disease and Related Phytoplasmas)," International J. of Syst. Bact. 46 (1):64-75, 1996.

Hooser et al., "Effects of an Insecticidal Dip Containing D-Limonene in the Cat," J. Am. Vet. Med. Assoc. 189 (8): 905-908, 1986.

Ishii, "Antibacterial Activity of Serprenone, a Non Water-Soluble Antiulcer Agent, Against Helicobacter Pylori," Int. J. Med. Microbiol. Virol. Parasitol. Infect Dis. 280 (1-2): 239-243, 1993.

JinNian, Z., Ping, J., CangSong, W., ShengLi, S., LiYuan, J., ChangChun, L.. 2000. Studies on Monochamus alternatus attractants and the attractability. Forest Research, Beijing 13(3):262-267. Abstract.

Kadota et al., "Antibacterial Activity of Trichorabdal A From Rabdosia Trichocarpa Against Helicobacter Pylori," Zentralbl. Bakteriol 287 (1):63-67, 1997.

Karlson et al., 1996. Inhibition of tumor cell growth by monoterpenes in vitro: evidence of a Ras-independent mechanism of action. Anticancer Drugs 7(4):422-429.

Khoshkhoo, N., Hedin, P. A., McCarty, J. C., Jr. 1994. Terpenoid aldehydes in root-knot nematode susceptible and resistant cotton-seeds as determined by HPLC and aniline methods. Journal of Agricultural and Food Chemistry. 42(3):804-806. Abstract.

Khoshkhoo, N., Hedin, P.A., McCarty, J.C. Terpenoid aldehydes in root-knot nematode susceptible and resistant cotton plants. J. Agric. Food Chem.; 1994; 42(1) pp. 204-208. Abstract.

(56) References Cited

OTHER PUBLICATIONS

Khoshkhoo, N., Hedin, P. A., McCarty, J. C.. Effects of bioregulators on the terpenoid aldehydes in root-knot nematode infected cotton plants. J. Agric. Food Chem.; 1993; 41(12) pp. 2442-2446. Abstract.

Kim et al., "Antibacterial Activity of Some Essential Oil Components Against Five Foodborne Pathogens," J. Agric. Food Chem. 43: 2839-2845, 1995.

Kirkpatrick B.C. & C.D. Smart—Phytoplasmas: can phylogeny provide the means to understand pathogenicity? Adv. Bot. Res., 21, 187-212 (1995).

Kirkpatrick, BC. Strategies for Characterizing Plant Pathogenic MIO and Their Effects on Plants, in T. Kosuge and E. W. Nester (Eds. ), Plant-Microbe Interactions: Molecular and Genetic Perspectives, vol. 3, Mcgraw-Hill, NY pp. 241-293, 1989.

Kokalis-Burelle, N., N. Martinez-Ochoa, R. Rodriguez-Kábana, and J. W. Kloepper. 2002. Development of multi-component transplant mixes for suppression of Meloidogyne incognita on tomato (*Lycopersicon esculentum*). Journal of Nematology 34: 362-369. Abstract.

Kokalis-Burelle, N, Kloepper, J.W., Rodriquez-Kabana, R., "Organic amendments and natural chemicals as components of transplant mixes control of root-knot nematode," *Phytopathology* 89:(6):S41 1999. Abstract.

Kunkel, "Heat Cure of Aster Yellows in Periwinkles," Am. J. Botany 28: 761-769, 1941.

Lee et al., Revised Classification Scheme of Phytoplasmas Based on RFPL Analyses of 16s RNA and Ribosomal Protein Gene Sequence [Review]. International Journal of Systematic Bacteriology. 48 : 1153-1169, 1998.

Lee et al., Universal Amplification and Analysis of Pathogen 16s Rdna for Classification and Identification of Mycoplasmalike Organisms. Phytopathology. 83: 834-842, 1993.

Lee et al.,"Genetic Interrelatedness Among Clover Proliferation Mycoplasmalike Organisms (MIOs) and Other MIOs Investigated by Nucleic Acid Hybridization and Restriction Fragment Length Polymorphism Analyses," Appl. Environ. Micro. 57 (12): 3565-3569, 199.

Mahajan, R., Singh, P., Bajaj, K. L., Kalsi, P. S. 1986. Nematicidal activity of some sesquiterpenoids against rootknot nematode (Meloidogyne incognita). Nematologica. 32(1):119-123. Abstract.

Mangel, M. S., Sangwan, N. K., Dhindsa, K. S., Verma, K. K., Bhatti, D. S. 1987. Nematicidal efficacy of some monoterpenes and related derivatives. Pesticides. 11(5):30-32. Abstract.

Markham, "The 'Yellows' Plant Diseases: Plant Hosts and Their Interaction With the Pathogens," pp. 82-100 in M. J. Daniels and P. G. Markham (Eds.), 1982.

McCoy and Williams, "Chemical Treatment for Control of Plant Mycoplasma Diseases," pp. 152-173, in M. J. Daniels and D. S. Williams (Eds.), Plant Insect Mycoplasma Techniques. London, Croom Helm, 1982.

McCoy, R.E., et al. Plant diseases associated with mycoplasma-like organisms. The Mycoplasmas: Spiroplasmas, Acholeplasmas, and Mycoplasmas of Plants and Arthropods, R.F. Whitcomb and J.G. Tully, eds. Academic Press Inc., San Diego, Ca. vol. 5: 545-640, 1.

Mikhlin et al. 1983. "Antifungal and antimicrobial activity of some derivatives of beta-ionone and vitamin A," Prikl Biokhim Mikrobiol. 19:795-803 Abstract.

Milman, I. A. Alanto- and isoalantolactones. 1990. Chemistry of Natural Compounds. 26(3):251-262. Abstract.

Moleyar and Narasimham, 1992. Antibacterial activity of essential oil components. Int J Food Microbiol 16(4).337-342.

Momin, R. A., Ramsewak, R. S., Nair, M. G. 2000. Bioactive compounds and 1,3-diỸ(cis)-9-octadecenoyl"-2-Ỹ(cis,cis)-9,12-octadecadienoyl" glycerol from Apium graveolens L. seeds. Journal of Agricultural and Food Chemistry. 48(9):3785-3788. Abstract.

Nandi, Effect of some volatile aldehydes, ketones, esters and terpenoids on growth and development of fungi associated with wheat grains in the field and in storage, Journal of Plant Diseases and Protection, 84(2):114-128 (1977), XP-001062894.

Owawunmi, "Evaluation of the Antimicrobial Activity of Citral," Letters in Applied Microbiology 9 (3): 105-108, 1989.

Pattnaik, et al. 1997. Antibacterial and antifungal activity of aromatic constituents of essential oils. Microbios 89(358):39-46.

Razin et al., 1998, Molecular Biology and Pathogenicity of Mycoplasmas, Micro. Mol. Bio. Rev. 62: 1094-1156, 1998.

Reuveni, "Activity of trifloxystrobin against powdery and downey mildew diseases of grapevines," Can. J. Plant Pathol. 23:52-59 2001 Abstract.

Rodriguez-Kabana, R. 2002. Soil fumigation: New uses for old chemicals and new compounds. Nematology 4(2):156. Abstract.

Salt et al., "Effects of b-Ionone and Abscisic Acid on the Growth of Tobacco and Resistance to Blue Mold, Mimicry the Effects of Stem Infection by Peronospora Tabaciraa," Adam Physiol. Molec. Plant Path 28: 287-297, 1986.

Sangwan, N. K., Verma, K. K., Verma, B. S., Mali, M. S., Dhindsa, K. S. 1985. 1985. Nematicidal activity of essential oils of Cymbopogon grasses. Nematologica. 31(1):93-99. Abstract.

Schafft et al., "Sensitive Detection and Identification of Mycoplasma-Like Organisms in Plants by Polymerase Chain Reactions," Biochem Biophys. Res. Comm. 186: 1503-1509, 1992.

Siddique et al., "Histopathology and Within—Plant Distribution of the Phytoplasma Associated With Australian Papaya Dieback," Plant Dis. 82 (10): 1112-1120, 1998.

Sinclair et al., Sampling and Histological Procedures for Diagnosis of Ash Yellows. Plant Disease. 73: 432-435, 1989.

Soler-Serratosa, A., Kokalis-Burelle, N., Rodriguez-Kabana, R., Weaver, C. F., King, P. S. 1996. Allelochemicals for control of plant-parasitic nematodes 1. In vivo nematicidal efficacy of thymol and thymol/benzaldehyde combinations. Nematropica. 26(1).

Stamps, William Terrell. Factors Regulating Exit of Bursaphelenchus Xylophilus (Nematoda : Aphelenchoididae) Fourth Stage Dispersal Juveniles From Their Beetle Vector Monochamus Carolinensis (Coleoptera: Cerambycidae) (Pine Wilt). University of Missouri.

Tominaga, Y., Yamamoto, M., Kuwahara, Y., and Sugawara, R. 1984. Behavioral responses. of the pine wood nematode to terpenes. Agric. Biol. Chem. 48:519-520.

Toner, M., "Report: Farms Raising Germs Resistance,"Atlanta Journal Constitution, p. A-7, Apr. 23, 2002.

Vasudevan, P., Kashyap, S., Sharma, S. 1997. Tagetes: a multipurpose plant. Bioresource Technology. 62(1/2):29-35. Abstract.

Veech JA • Histochemical localization and nematoxicity of terpenoid aldehydes in cotton • J.Nematol.;(1979);v. 11(3) p. 240-246.

Vera, R. 1993. Chemical composition of the essential oil of Ageratum conyzoides L. (Asteraceae) from Reunion. Flavour and Fragrance Journal. 8(5):257-260. Abstract.

Wang, Z. M., Cheng, P. Y., Min, Z. D., Zheng, Q. T., Wu, C. Y., Xu, M. J., Gue, Y. W., Mizuno, M., Iinuma, M., Tanaka, T. 1991. Ent-kaurene diterpenoids, isodopharicins A, B and C in Isodon pharicus. Phytochemistry. 30(11):3699-3702. Abstract.

Watanabe, I., Koike, K., Satou, T., Nikaido, T. 1999. Nerriatocidal activity of picrodendrins against a species of Diplogastridae. Biological & Pharmaceutical Bulletin. 22(12):1310-1313. Abstract.

Willett,. J. D. (1980). Control mechanisms in nematodes. In Nematodes as Biological Models,. vol. 1 (ed. B. M. Zuckerman), pp. 197-225. Abstract.

Wuyts N., Elsen A., De Waele D., Swennen R. and Sági L., 2002. Potential of plant secondary metabolites to increase resistance against plant-parasitic nematodes. 8th Ph.D. Symposium on Applied Biological Sciences. Universiteit Gent, Belgium, Oct. 9, 200.

Xu, G., Su, Z. 1994. Study on the terpenoids in Pinus thunbergii Parl. infected with Bursaphelenchus xylophilus. Chemistry and Industry of Forest Products. 14(3):49-54. Abstract.

Xu, Y. L., Wang, D., Li, X. J., Fu, J. 1989. Abietane quinones from Rabdosia Iophanthoides. Phytochemistry. 28(1):189-191. Abstract.

Yu et al., "The Efficacy of B-Ionone in the Chemoprevention of Rat Mammary Carcinogenesis," J. Angri. Food Chem. 43: 2144-2147, 1995.

Zhao, Z., Li, D., Hu, X., Xu, F., Sun, Z., Hu, G., Liu, X. 1999. Study on variations of neutral terpenoids of resistant provenances of P. massoniana after inoculating Bursaphelenchus xylophilus. pp. 217-

(56) References Cited

OTHER PUBLICATIONS

221 Sustainability of pine forests in relation to pine wilt and decline. Proceedings of International Symposium, Tokyo, Japan, Oct. 27-28, 1998 Abstract.

ZhenDong, Z., DongMei, L., XiE, H., FuYuan, X., Zhen, S., GuiXian, H., XianZhang, L. 2001. Study on chemical components and resistance mechanism to pine wood nematode of Masson pine provenance (II):—study on the components of neutral terpenoids and their differences amoung different resistant provenances of Pinu massoniana. Chemistry and Industry of Forest Products. 21(1):56-60.

ZhenDong, Z., XiE, H., DongMei, L., FuYuan, X., GuiXian, H., Zhen, S., XianZhang, L. 2001. Study on chemical components and resistance mechanism to pine wood nematode of masson pine provenance (III). Chemistry and Industry of Forest Products. 21(3):52-58.

Zinovieva, S. V., Vasyukova, N. I., Ozeretskovskaya, I. L. 1990. Involvement of plant sterols in the system tomatoes—nematode Meloidogyne incognita. Helminthologia 27(3):211-216. Abstract.

Ladd TL. (1980) Japanese beetle: enhancement of lures by eugenol and caproic acid. J Economic Entomology. 73(5): 718-720. (Abstract Only).

Schmidt JO. (1994) Attraction of reproductive honey bee swarms to artificial nests by Nasonov pheromone. J Chemical Ecology. 20(5): 1053-1056. (Abstract Only).

International Preliminary Report on Patentability issued Jun. 3, 2008 for Application PCT/GB2006/002878 filed Aug. 3, 2006 and published as WO 2007/063267 on Jun. 7, 2007 (Inventor—Gary Ostroff // Applicant—Eden Research PLC) (7 pages).

Response filed May 19, 2014 for U.S. Appl. No. 10/586,597, filed Jan. 24, 2005 (Inventor—Lanny Franklin // Applicant—Eden Research PLC) (17 pages).

Final Rejection issued Dec. 17, 2013 for U.S. Appl. No. 10/586,597, filed Jan. 24, 2005 (Inventor—Lanny Franklin // Applicant—Eden Research PLC) (10 pages).

Response filed Dec. 2, 2013 for U.S. Appl. No. 10/586,597, filed Jan. 24, 2005 (Inventor—Lanny Franklin // Applicant—Eden Research PLC) (27 pages).

Non-Final Rejection issued May 30, 2013 for U.S. Appl. No. 10/586,597, filed Jan. 24, 2005 (Inventor—Lanny Franklin // Applicant—Eden Research PLC) (13 pages).

Final Rejection issued Apr. 18, 2011 for U.S. Appl. No. 10/586,597, filed Jan. 24, 2005 (Inventor—Lanny Franklin // Applicant—Eden Research PLC) (12 pages).

Response filed Feb. 15, 2011 for U.S. Appl. No. 10/586,597, filed Jan. 24, 2005 (Inventor—Lanny Franklin // Applicant—Eden Research PLC) (20 pages).

Non-Final Rejection issued Oct. 15, 2010 for U.S. Appl. No. 10/586,597, filed Jan. 24, 2005 (Inventor—Lanny Franklin // Applicant—Eden Research PLC) (12 pages).

Examiner Interview Summary Record issued Jul. 26, 2010 for U.S. Appl. No. 10/586,597, filed Jan. 24, 2005 (Inventor—Lanny Franklin // Applicant—Eden Research PLC) (3 pages).

Response to Restriction Requirement filed Jul. 19, 2010 for U.S. Appl. No. 10/586,597, filed Jan. 24, 2005 (Inventor—Lanny Franklin // Applicant—Eden Research PLC) (13 pages).

Requirement for Restriction issued Jun. 18, 2010 for U.S. Appl. No. 10/586,597, filed Jan. 24, 2005 (Inventor—Lanny Franklin // Applicant—Eden Research PLC) (8 pages).

Response filed Jun. 19, 2014 for U.S. Appl. No. 11/597,116, filed Jan. 24, 2005 (Inventor—Lanny Franklin // Applicant—Eden Research PLC) (16 pages).

Final Rejection issued Dec. 19, 2013 for U.S. Appl. No. 11/597,116, filed Jan. 24, 2005 (Inventor—Lanny Franklin // Applicant—Eden Research PLC) (24 pages).

Response filed Nov. 18, 2013 for U.S. Appl. No. 11/597,116, filed Jan. 24, 2005 (Inventor—Lanny Franklin // Applicant—Eden Research PLC) (19 pages).

Non-Final Rejection issued Jun. 18, 2013 for U.S. Appl. No. 11/597,116, filed Jan. 24, 2005 (Inventor—Lanny Franklin // Applicant—Eden Research PLC) (22 pages).

Response filed Oct. 12, 2012 for U.S. Appl. No. 11/597,116, filed Jan. 24, 2005 (Inventor—Lanny Franklin // Applicant—Eden Research PLC) (19 pages).

Non-Final Rejection issued Jul. 12, 2012 for U.S. Appl. No. 11/597,116, filed Jan. 24, 2005 (Inventor—Lanny Franklin // Applicant—Eden Research PLC) (18 pages).

Response filed Apr. 13, 2012 for U.S. Appl. No. 11/597,116, filed Jan. 24, 2005 (Inventor—Lanny Franklin // Applicant—Eden Research PLC) (18 pages).

Non-Final Rejection issued Dec. 13, 2011 for U.S. Appl. No. 11/597,116, filed Jan. 24, 2005 (Inventor—Lanny Franklin // Applicant—Eden Research PLC) (15 pages).

Response filed Jun. 27, 2011 for U.S. Appl. No. 11/597,116, filed Jan. 24, 2005 (Inventor—Lanny Franklin // Applicant—Eden Research PLC) (14 pages).

Requirement for Restriction issued Apr. 26, 2011 for U.S. Appl. No. 11/597,116, filed Jan. 24, 2005 (Inventor—Lanny Franklin // Applicant—Eden Research PLC) (8 pages).

Response filed May 4, 2014 for U.S. Appl. No. 12/095,584 filed Aug. 28, 2009 (Invento—Lanny Franklin // Applicant—Eden Research PLC) (27 pages).

Final Rejection issued Nov. 5, 2013 for U.S. Appl. No. 12/095,584, filed Aug. 28, 2009 (Inventor—Lanny Franklin // Applicant—Eden Research PLC) (22 pages).

Final Rejection issued Apr. 17, 2012 for U.S. Appl. No. 12/095,584, filed Aug. 28, 2009 and published as 2010/0136102 on Jun. 3, 2010 (Inventor—Lanny Franklin // Applicant—Eden Research PLC) (19 pages).

Response filed Mar. 5, 2012 for U.S. Appl. No. 12/095,584, filed Aug. 28, 2009 (Inventor—Lanny Franklin // Applicant—Eden Research PLC) (21 pages).

Non-Final Rejection issued Oct. 7, 2011 for U.S. Appl. No. 12/095,584, filed Aug. 28, 2009 (Inventor—Lanny Franklin // Applicant—Eden Research PL) (15 pages).

Andes et al. (2000) Report of Successful prolonged antifungal therapy for refractory allergic fungal sinusitis. Clinical Infectious Diseases, 31(1): 202-204.

Author Unknown (1998) "Yeast—better a friend than foe!" Food Processing, 67(9): 15-18.

Calvet et al. (2001) Evaluation of natural compounds against Root-lesion and root-knot nematodes and side effects on the ineffectivity of arbuscular mycorrhizal fungi. European J. Plant Pathology. 107(6): 601-605.

Fleet CH, et al (1991). "Cell walls." The Yeasts, 4(2): 199-277.

Ladd TL, et al. (1974) Attraction of bumble bees and honey bees to traps baited with lures for the Japanese beetle. J Economic Entomology. 67(2): 307-308. (Abstract only).

Ladd TL. (1980) Japanese beetle: enhancement of lures by eugenol and caproic acid. J. Economic Entomology. 73(5): 718-720. (Abstract only).

Oka et al (2000) Nematodicidal activity of essential oils and their components against Root-knot nematode. Phytopathology. 90(7): 710-715.

Rattray et al. (1975). Lipids of yeasts. Bacteriological Reviews, 39(3): 197-231.

Sances et al. (1992) Minimization of pesticide residues on head lettuce: Within-head residue distribution of selected insecticides. J. Econ. Etymol. 85: 202.

Schmidt JO. (1994) Attraction of reproductive honey bee swarms to artificial nests by Nasonov pheromone. J Chemical Ecology. 20(5) 1053-1056.

Yokota M, et al. (1994) Antimicrobial effect of aromatic natural compound, chiefly against Staphylococcus aureus. Igaku to Seibutsugaku. 128(3): 105-110. (Abstract only).

Non-Final Office Action issued on Oct. 6, 2014 for U.S. Appl. No. 10/586,597, filed Apr. 4, 2008 (Inventor—Lanny Franklin//Applicant—Eden Research PLC) (15 pages).

Response to Office Action filed Apr. 6, 2015 for U.S. Appl. No. 10/586,597 filed Apr. 4, 2008 (Inventor—Lanny Franklin//Applicant—Eden Research PLC) (16 pages).

(56) References Cited

OTHER PUBLICATIONS

Notice of Non-Compliant Amendment issued on Apr. 21, 2015 for U.S. Appl. No. 10/586,597, filed Apr. 4, 2008 (Inventor—Lanny Franklin//Applicant—Eden Research PLC) (3 pages).
Response to Notice of Non-Compliant Amendment filed Jun. 10, 2015 for U.S. Appl. No. 10/586,597, filed Apr. 4, 2008 (Inventor—Lanny Franklin//Applicant—Eden Research PLC) (7 pages).
Final Office Action issued on Sep. 2, 2015 for U.S. Appl. No. 10/586,597, filed Apr. 4, 2008 (Inventor—Lanny Franklin//Applicant—Eden Research PLC) (17 pages).
Response to Office Action filed Mar. 2, 2016 for U.S. Appl. No. 10/586,597, filed Apr. 4, 2008 (Inventor—Lanny Franklin//Applicant—Eden Research PLC) (19 pages).
Non-Final Office Action issued on Mar. 24, 2016 for U.S. Appl. No. 10/586,597, filed Apr. 4, 2008 (Inventor—Lanny Franklin//Applicant—Eden Research PLC) (17 pages).
Final Office Action issued Dec. 17, 2014 for U.S. Appl. No. 11/597,116, filed Oct. 27, 2008 (Inventor—Lanny Franklin//Applicant—Eden Research PLC) (18 pages).
Response to Office Action filed Jun. 17, 2015 for U.S. Appl. No. 11/597,116, filed Oct. 27, 2008 (Inventor—Lanny Franklin//Applicant—Eden Research PLC) (17 pages).
Final Office Action issued Sep. 11, 2015 for U.S. Appl. No. 11/597,116, filed Oct. 27, 2008 (Inventor—Lanny Franklin//Applicant—Eden Research PLC) (19 pages).
Response to Office Action filed Mar. 10, 2016 for U.S. Appl. No. 11/597,116, filed Oct. 27, 2008 (Inventor—Lanny Franklin//Applicant—Eden Research PLC) (18 pages).
Response to Office Action filed Sep. 17, 2012 for U.S. Appl. No. 12/095,584, filed Aug. 28, 2009 (Inventor—Lanny Franklin//Applicant—Eden Research PLC) (23 pages).
Final Office Action issued Jul. 8, 2014 for U.S. Appl. No. 12/095,584, filed Aug. 28, 2009 (Inventor—Lanny Franklin//Applicant—Eden Research PLC) (20 pages).
Response to Office Action filed Jan. 8, 2015 for U.S. Appl. No. 12/095,584, filed Aug. 28, 2009 (Inventor—Lanny Franklin//Applicant—Eden Research PLC) (22 pages).
Final Office Action issued Feb. 13, 2015 for U.S. Appl. No. 12/095,584, filed Aug. 28, 2009 (Inventor—Lanny Franklin//Applicant—Eden Research PLC) (19 pages).
Response to Office Action filed Aug. 13, 2015 for U.S. Appl. No. 12/095,584, filed Aug. 28, 2009 (Inventor—Lanny Franklin//Applicant—Eden Research PLC) (17 pages).
Supplemental Response to Office Action filed Sep. 4, 2015 for U.S. Appl. No. 12/05,584, filed Aug. 28, 2009 (Inventor—Lanny Franklin//Applicant—Eden Research PLC) (14 pages).
Non-Final Office Action issued Sep. 9, 2015 for U.S. Appl. No. 12/095,584, filed Aug. 8, 2009 (Inventor—Lanny Franklin//Applicant—Eden Research PLC) (23 pages).
Response to Office Action filed Mar. 25, 2016 for U.S. Appl. No. 12/095,584, filed Aug. 28, 2009 (Inventor—Lanny Franklin//Applicant—Eden Research PLC) (25 pages).
Final Office Action issued Apr. 26, 2016 for U.S. Appl. No. 12/095,584, filed Aug. 28, 2009 (Inventor—Lanny Franklin//Applicant—Eden Research PLC) (27 pages).
Preliminary Amendment filed Feb. 25, 2014 for U.S. Appl. No. 14/188,790, filed Feb. 25, 2014 (Inventor—Lanny Franklin//Applicant—Eden Research PLC) (6 pages).
Non-Final Office Action issued Jul. 14, 2015 for U.S. Appl. No. 14/188,790, filed Feb. 25, 2014 (Inventor—Lanny Franklin//Applicant—Eden Research PLC) (15 pages).
Response to Office Action filed Jan. 13, 2016 for U.S. Appl. No. 14/188,790, filed Feb. 25, 2014 (Inventor—Lanny Franklin//Applicant—Eden Research PLC) (17 pages).
Final Office Action issued Mar. 16, 2016 for U.S. Appl. No. 14/188,790, filed Feb. 25, 2014 (Inventor—Lanny Franklin//Applicant—Eden Research PLC) (24 pages).
U.S. Pat. No. 5,013,566 issued May 7, 1991 to M.J. Sampson.
U.S. Pat. No. 5,032,401 issued Jul. 16, 1991 to Jamas et al.
U.S. Pat. No. 6,685,954 issued Feb. 3, 2004 to P. Jeannin.
U.S. Patent App. Pub. No. 2002/0028256 published Mar. 7, 2002 to S.M. Bessette.
U.S. Patent App. Pub. No. 2005/0281781 published Dec. 22, 2005 to G.R. Ostroff.
Bishop Jr, et al. (1998) Microencapsulation in yeast cells. J Microencapsul. 15(6):761-773 (Abstract Only).

\* cited by examiner

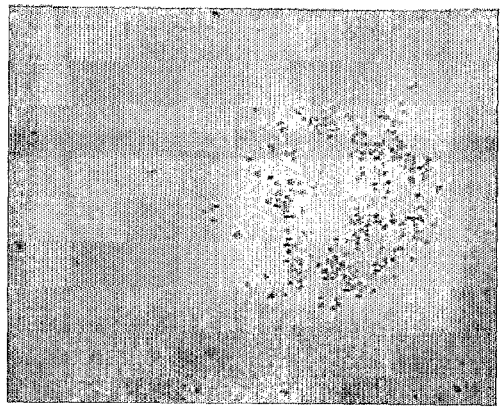
Fig 19                                  Fig 20
| Site 18 | | Site 20 |
|---|---|---|
| Conventional treatment | | Conventional treatment |
| YGP-GET liquid formulation 1 g/L | | YGP-GET powder formulation 0.5 g/L |
| No treatment | | No treatment |
| YGP-GET liquid formulation 4 g/L | | YGP-GET powder formulation 2 g/L |
Fig 21

Site 18

| Conventional treatment |
| No treatment |
| YGP-GET liquid formulation 2 mL/L |

Site 20

| No treatment |
| YGP-GET liquid formulation 2 mL/L |
| No treatment |

Fig 22

| YGP-GET liquid formulation 4 mL/L |
| No treatment |

Fig 23

COMPOSITIONS AND METHODS COMPRISING TERPENES OR TERPENE MIXTURES SELECTED FROM THYMOL, EUGENOL, GERANIOL, CITRAL, AND L-CARVONE

CROSS REFERENCE TO RELATED APPLICATIONS

The present application is a National Phase Application of International Application No. PCT/GB2006/002881, filed Aug. 3, 2006, which claims priority to U.S. Patent Application No. 60/741,167, filed Nov. 30, 2005, which applications are incorporated herein fully by this reference.

The present invention relates to compositions comprising terpenes which are particularly suitable for treating plant infections, to methods of making such compositions, and to methods of using them. The present invention also relates to compositions comprising terpenes and hollow glucan particles or cell wall particles and methods for preparing such compositions; such compositions increase terpene stability and activity and provide a suitable carrier for the terpenes. The invention also relates to methods of using such compositions in the medical, veterinary and agricultural fields.

Terpenes are chemical compounds that are widespread in nature, mainly in plants as constituents of essential oils. Their building block is the hydrocarbon isoprene $(C_5H_8)_n$. Examples of terpenes include citral, pinene, nerol, b-ionone, geraniol, carvacrol, eugenol, carvone, terpeniol, anethole, camphor, menthol, limonene, nerolidol, farnesol, phytol, carotene (vitamin $A_1$), squalene, thymol, tocotrienol, perillyl alcohol, borneol, myrcene, simene, carene, terpenene, and linalool.

Terpenes are classified as Generally Recognized as Safe (GRAS) and have been used for many years in the flavouring and aroma industries. The $LD_{50}$ in rats of citral is approximately 5 g/kg, which is a further indication of the relative safety of these compounds. Furthermore, terpenes have a relatively short life span of approximately 28 days once exposed to oxygen (e.g. air). Terpenes will decompose to $CO_2$ and water. This decomposition or break down of terpenes demonstrates the safety and environmental friendliness of the compositions and methods of the invention.

Terpenes have been found to inhibit the growth of cancerous cells, decrease tumour size, decrease cholesterol levels, and have a biocidal effect on micro-organisms in vitro. Owawunmi, (Letters in Applied Microbiology, 1993, 9(3): 105-108), showed that growth media with more than 0.01% citral reduced the concentration of *E. coli*, and at 0.08% there was a bactericidal effect. U.S. Pat. No. 5,673,468 describes a terpene formulation, based on pine oil, used as a disinfectant or antiseptic cleaner. U.S. Pat. No. 5,849,956 teaches that a terpene found in rice has antifungal activity. U.S. Pat. No. 5,939,050 describes an oral hygiene antimicrobial product with a combination of 2 or 3 terpenes that showed a synergistic effect. Several U.S. patents (U.S. Pat. Nos. 5,547,677, 5,549,901, 5,618,840, 5,629,021, 5,662,957, 5,700,679, 5,730,989) teach that certain types of oil-in-water emulsions have antimicrobial, adjuvant, and delivery properties.

Terpenes have been found to be effective and nontoxic dietary anti-tumor agents, which act through a variety of mechanisms of action (Crowell et al. Crit. Rev. Oncog., 1994, 5(1): 1-22; Crowell et al. Adv. Exp. Med. Biol., 1996, 401: 131-136). The terpenes geraniol, tocotrienol, perillyl alcohol, b-ionone, and d-limonene, suppress hepatic HMG-CoA reductase activity, a rate limiting step in cholesterol synthesis, and modestly lower cholesterol levels in animals (Elson et al, J. Nutr., 1994, 124: 607-614). D-limonene and geraniol reduced mammary tumors (Elegbede et al. Carcinogenesis, 1984, 5(5): 661-664; Elegbede et al., J. Natl. Cancer Inst., 1986, 76(2): 323-325; Karlson et al. Anticancer Drugs, 1996, 7(4): 422-429) and suppressed the growth of transplanted tumors (Yu et al., J. Agri. Food Chem., 1995, 43: 2144-2147).

Terpenes have also been found to inhibit the in vitro growth of bacteria and fungi (Chaumont et al.), Ann. Pharm. Fr., 1992, 50(3): 156-166; Moleyar et al., Int. J. Food Microbiol, 1992, 16(4): 337-342; and Pattnaik et al. Microbios, 1997, 89(358): 39-46) and some internal and external parasites (Hooser et al., J. Am. Vet. Med. Assoc., 1986, 189(8): 905-908). Geraniol was found to inhibit growth of *Candida albicans* and *Saccharomyces cerevisiae* strains by enhancing the rate of potassium leakage and disrupting membrane fluidity (Bard et al., Lipids, 1998, 23(6): 534-538). B-ionone has antifungal activity which was determined by inhibition of spore germination, and growth inhibition in agar (Mikhlin et al., A. Prikl. Biokhim. Mikrobiol, 1983, 19: 795-803; Salt et al., Adam. Physiol. Molec. Plant Path, 1986, 28: 287-297). Teprenone geranylgeranylacetone has an antibacterial effect on *H. pylori* (Ishii, Int. J. Med. Microbiol. Virol. Parasitol. Infect. Dis., 1993, 280(1-2): 239-243). Rosanol, a commercial product with 1% rose oil, has been shown to inhibit the growth of several bacteria (*Pseudomonas, Staphylococcus, E. coli*, and *H. pylori*). Geraniol is the active component (75%) of rose oil. Rose oil and geraniol at a concentration of 2 mg/L inhibited the growth of *H. pylori* in vitro. Some extracts from herbal medicines have been shown to have an inhibitory effect in *H. pylori*, the most effective being decursinol angelate, decursin, magnolol, berberine, cinnamic acid, decursinol, and gallic acid (Bae et al., Biol. Pharm. Bull., 1998, 21(9) 990-992). Extracts from cashew apple, anacardic acid, and (E)-2-hexenal have shown bactericidal effect against *H. pylori*.

Diterpenes, i.e., trichorabdal A (from *R. Trichocarpa*), have shown a very strong antibacterial effect against *H. pylori* (Kadota et al., Zentralbl. Bakteriol, 1997, 287(1): 63-67).

Solutions of 11 different terpenes were effective in inhibiting the growth of pathogenic bacteria in in vitro tests; levels ranging between 100 ppm and 1000 ppm were effective. The terpenes were diluted in water with 1% polysorbate 20 (Kim et al., J. Agric. Food Chem., 1995, 43: 2839-2845).

There may be different modes of action of terpenes against microorganisms; they could (1) interfere with the phospholipid bilayer of the cell membrane, (2) impair a variety of enzyme systems (HMG-reductase), and (3) destroy or inactivate genetic material. It is believed that due to the modes of action of terpenes being so basic, e.g., blocking of cholesterol, that infective agents will not be able to build a resistance to terpenes.

There are, however, a number of drawbacks to the use of terpenes. These include:

Terpenes are liquids which can make them difficult to handle and unsuitable for certain purposes.

Terpenes are not very miscible with water, and it generally requires the use of detergents, surfactants or other emulsifiers to prepare aqueous emulsions. A stable solution can, however, be obtained by mixing the terpenes under high shear.

Dry powder terpene formulations generally only contain a low percentage w/w of terpenes.

Terpenes are prone to oxidation in aqueous emulsion systems, which make long term storage a problem.

There are limitations to the current techniques of spray coating, extrusion, coacervation, molecular encapsulation, and spray drying/cooling to provide ingredient delivery systems.

Baker's yeast cell walls are derived from baker's yeast cells and are composed of the insoluble biopolymers β-1,3-glucan, β-1,6-glucan, mannan and chitin. They are typically 2-4 micron in diameter microspheres with a shell wall that is only 0.2-0.3 micron thick surrounding an open cavity. This material has considerable liquid holding capacity, typically absorbing 5-25 times its weight in liquid. The shell is sufficiently porous that payloads up to 150,000 Daltons in size can pass through the outer shell and be absorbed into the hollow cavity of the spherical particle. Baker's yeast cell walls have several unique properties, including heat stability (e.g. to 121° C.), shear stability, pH stability (e.g. pH 2-12), and at high concentrations they do not build significant viscosity. In addition to its physical properties this composition contains natural and healthy dietary fibres that deliver cardiovascular and immunopotentiation health benefits.

Yeast cell walls are prepared from yeast cells by the extraction and purification of the insoluble particulate fraction from the soluble components of the yeast cell. The fungal cell walls can be produced from the insoluble byproduct of yeast extract manufacture. Further, the yeast cells can be treated with an aqueous hydroxide solution, without disrupting the yeast cell walls, which digests the protein and intracellular portion of the cell, leaving the yeast cell wall component devoid of significant protein contamination, and having substantially the unaltered cell wall structure of β(1-6) and β(1-3) linked glucans. A more detailed description of whole glucan particles and the process of preparing them is described by Jamas et al. in U.S. Pat. No. 4,810,646 and in co-pending patent applications U.S. Ser. No. 166,929, U.S. Ser. No. 297,752 and U.S. Ser. No. 297,982. U.S. Pat. No. 6,242,594, assigned to Novogen Research Pty Ltd., describes a method of preparing yeast glucan particles by alkali extraction, acid extraction and then extraction with an organic solvent and finally drying. U.S. Pat. No. 5,401,727, assigned to AS Biotech-Mackzymal, discloses the methods of obtaining yeast glucan particles and methods of using them to promote resistance in aquatic animals and as an adjuvant for vaccinations. U.S. Pat. No. 5,607,677, assigned to Alpha-Beta Technology Inc., discloses the use of hollow whole glucan particles as a delivery package and adjuvant for the delivery of a variety of pharmaceutical agents. The teachings of the abovementioned patents and applications are incorporated herein by reference.

Other types of yeast and fungi cells have cell walls that do not contain glucan. The cell walls of such yeast and fungi can be isolated by similar techniques to those mentioned above to obtain cell wall particles.

Additionally, the cells of many plants, algae, bacteria and other micro-organisms also comprise a cell wall. The structure and composition of the cell wall varies between micro-organism, but in general it is a robust and relatively inert structure. It is possible to obtain cell wall particles derived from such cells through conventional techniques, such as those mentioned above in relation to yeast.

Terpenes can be taken up and stably encapsulated within hollow glucan particles or cell wall particles. Encapsulation of terpenes into such particles can be achieved by incubation of the particles with the terpene.

It has been found that certain mixtures of more than one terpene exhibit higher efficacy than others. In particular, formulations have been identified which have high efficacy in controlling micro organisms, especially plant pathogens.

According to the present invention there is provided a composition comprising a terpene component, the terpene component comprising a mixture of more than one terpene selected from the group consisting of thymol, eugenol, geraniol and citral. Such formulations have been shown to be particularly potent in killing micro-organisms. In particular these formulations have been shown to be generally effective in treating and preventing plant infections.

In an embodiment of the present invention the composition comprises a terpene component comprising a combination of thymol and one or more of eugenol, geraniol, citral. Such compositions have been found to be especially effective in treating and preventing plant infections. The presence of thymol in such compositions typically results in high levels of efficacy. However, thymol on its own is typically not as effective as when it is combined with one or more of geranol, eugenol and citral. This suggests there is a synergistic effect occurring between the various terpenes in the combinations of the present invention.

When obtaining regulatory approval for a new product for medical or agricultural use, it is generally simpler to register a composition having fewer active ingredients. Accordingly it is generally preferable that the composition of the present invention comprises a terpene component comprising four or fewer terpenes; preferably three or fewer terpenes.

In one embodiment the composition comprises a terpene component comprising thymol and geraniol. Optionally the terpene component comprises between about 10% and 90% of thymol and between about 10% and 90% geraniol; suitably the terpene component comprises between about 40% and 60% of thymol and between about 40% and 60% geraniol. The terpene component can optionally comprise less than 10% of any other terpene, suitably less than 5%. In one embodiment the terpene component consists exclusively of thymol and geraniol. Such a composition has been shown to be highly effective across a broad range of plant pathogens, particularly against fungi/oomycetes.

In another embodiment the composition comprises a terpene component comprising thymol and citral. Optionally the terpene component comprises between about 10% and 90% of thymol and between about 10% and 90% citral; suitably the terpene component comprises between about 40% and 60% of thymol and between about 40% and 60% citral. The terpene component can optionally comprise less than 10% of any other terpene, suitably less than 5%. In one embodiment the terpene component consists exclusively of thymol and citral. Such a composition has been shown to be highly effective across a broad range of plant pathogens, particularly against bacteria.

In another embodiment the composition comprises a terpene component comprising thymol and eugenol. Optionally the terpene component comprises between about 10% and 90% of thymol and between about 10% and 90% eugenol; suitably the terpene component comprises between about 40% and 60% of thymol and between about 40% and 60% eugenol. The terpene component can optionally comprise less than 10% of any other terpene, suitably less than 5%. In one embodiment the terpene component consists exclusively of thymol and eugenol. Such a composition has been shown to be highly effective across a broad range of plant pathogens.

In another embodiment the composition comprises a terpene component comprising thymol, geraniol and citral. Optionally the terpene component comprises between about 10% and 90% of thymol, between about 10% and 90% geraniol, and between about 10% and 90% of citral; suitably the terpene component comprises between about 25% and 50% of thymol and between about 25% and 50% geraniol, and between about 25% and 50% of citral. The terpene component can optionally comprise less than 10% of any other terpene, suitably less than 5%. In one embodiment the terpene component consists exclusively of thymol, geraniol and citral. Such a composition has been shown to be highly effective across a broad range of plant pathogens.

In another embodiment the composition comprises a terpene component comprising thymol, eugenol and citral. Optionally the terpene component comprises between about 10% and 90% of thymol, between about 10% and 90% eugenol, and between about 10% and 90% of citral; suitably the terpene component comprises between about 25% and 50% of thymol and between about 25% and 50% eugenol, and between about 25% and 50% of citral. The terpene component can optionally comprise less than 10% of any other terpene, suitably less than 5%. In one embodiment the terpene component consists exclusively of thymol, eugenol and citral. Such a composition has been shown to be highly effective across a broad range of plant pathogens.

In another embodiment the composition comprises a terpene component comprising thymol, geraniol and eugenol. Optionally the terpene component comprises between about 10% and 90% of thymol, between about 10% and 90% geraniol, and between about 10% and 90% of eugenol; suitably the terpene component comprises between about 25% and 50% of thymol and between about 25% and 50% geraniol, and between about 25% and 50% of eugenol. The terpene component can optionally comprise less than 10% of any other terpene, suitably less than 5%. In one embodiment the terpene component consists exclusively of thymol, geraniol and eugenol. Such a composition has been shown to be highly effective across a broad range of plant pathogens.

In another embodiment the composition comprises a terpene component comprising thymol, eugenol and geraniol. Optionally the terpene component comprises between about 10% and 90% of thymol, between about 10% and 90% eugenol, and between about 10% and 90% of geraniol, suitably between about 25% and 50% of thymol and between about 25% and 50% eugenol, and between about 25% and 60% of geraniol. The terpene component can optionally comprise less than 10% of any other terpene, suitably less than 5%. In one embodiment the terpene component consists exclusively of thymol, eugenol and geraniol. Such a composition has been shown to be highly effective across a broad range of plant pathogens.

In another embodiment the composition comprises a terpene component comprising thymol, geraniol, eugenol and citral. Optionally the terpene component comprises between about 10% and 90% of thymol, between about 10% and 90% geraniol, between about 10% and 90% of eugenol, and between about 10 and 90% citral; suitably the terpene component comprises between about 15% and 50% of thymol and between about 15% and 50% geraniol, between about 15% and 50% of eugenol, and between about 15% and 50% of citral. The terpene component can optionally comprise less than 10% of any other terpene, suitably less than 5%. In one embodiment the terpene component consists exclusively of thymol, geraniol, eugenol and citral. Such a composition has been shown to be highly effective across a broad range of plant pathogens.

It has been found that terpene compositions comprising L-carvone are typically less effective in treating bacterial and fungal/oomycete plant infections. Accordingly, where the above compositions are intended for the treatment of such infections, it is generally preferable that they do not contain L-carvone.

The formulations mentioned alone have been demonstrated to be particularly effective in killing plant bacteria and fungi/oomycetes. However, it is reasonable to assume that these high levels of efficacy would be observed in respect of pathogens which cause infections in other organisms. For example, bacteria and fungi which affect animals, including humans. Accordingly, the compositions of the present invention are suitable for killing pathogens of animals and humans in general.

Additionally, terpenes have been shown to be effective in killing insects and arachmids, and it may be reasonably expected that the compositions according to the present invention would have high efficacy in killing such organisms.

It should be noted that terpenes are also known by the names of the extract or essential oil which contain them, e.g. lemongrass oil (contains citral).

In one aspect of the present invention the composition comprises a terpene component as defined above in suspension or solution in a solvent. Suitably the solvent is water.

Solutions of terpene in water can be achieved by mixing terpenes and water at high shear (see for example WO03/020024).

Suspensions (or emulsions) of terpenes in water, in association with a surfactant, are well known in the art (see for example WO03/020024 and WO2005/070213). The surfactant can be non-ionic, cationic, or anionic.

Examples of suitable surfactants include sodium lauryl sulphate, polysorbate 20, polysorbate 80, polysorbate 40, polysorbate 60, polyglyceryl ester, polyglyceryl monooleate, decaglyceryl monocaprylate, propylene glycol dicaprilate, triglycerol monostearate, polyoxyethylenesorbitan, monooleate, Tween®, Span® 20, Span® 40, Span® 60, Span® 80, Brig 30 or mixtures thereof.

According to a further aspect of the present invention there is provided a composition comprising a hollow glucan particle or a cell wall particle encapsulating a terpene component as set out above.

The term "hollow glucan particle" as used herein includes any hollow particle comprising glucan as a structural component. Thus, in particular, the term includes yeast cell walls (in purified or crude forms) or hollow whole glucan particles. The term "cell wall particle" refers to a particle comprising the wall of a cell (in a purified or crude form), wherein glucan is not a structural component. Suitable particles include the cell walls of plant, algal, fungal or bacterial cells. Cell wall particles generally retain the shape of the cell from which they are derived, and thus, like a hollow glucan particle, provide a hollow central cavity suitable for encapsulating the terpene component.

It is necessary that the hollow glucan particle or cell wall particle of the present invention is able to stably encapsulate the terpene component. In general this means the hollow glucan particle or cell wall particle must be able to maintain its structure during incubation with the terpene component (generally the terpene component is at a relatively high concentration), and that terpene component must be able to migrate into the particle. Hollow glucan particles and cell wall particles are generally formed from relatively inert materials and are porous, and thus it can be assumed that, in general, hollow glucan particles and cell wall particles will be able to encapsulate a terpene component.

Compositions according to the present invention are effective against various infective agents including bacteria, viruses, mycoplasmas, fungi and/or nematodes.

Encapsulation of the terpene component within a hollow glucan particle or a cell wall particle can provide the following advantages:
- maximise terpene payload;
- minimise unencapsulated payload;
- control payload stability;
- control payload release kinetics;
- creation of a solid form of a liquid terpene to increase the mass and uniformity;
- simplify handling and application of terpenes; and
- mask the smell and taste of the terpene.

Particularly suitable hollow glucan particles or cell wall particles are fungal cell walls, preferably yeast cell walls. Yeast cell walls are preparations of yeast cells that retain the three-dimensional structure of the yeast cell from which they are derived. Thus they have a hollow structure which allows the terpene component to be encapsulated within the yeast cell walls. The yeast walls may suitably be derived from Baker's yeast cells (available from Sigma Chemical Corp., St. Louis, Mo.). Yeast cell wall particles with desirable properties can also be obtained from Biorigin (Sao Paolo, Brazil) under the trade name Nutricell MOS 55. These particles are a spray dried extract of *S. cerevisiae*.

Alternative particles are those known by the trade names SAF-Mannan (SAF Agri, Minneapolis, Minn.) and Nutrex (Sensient Technologies, Milwaukee, Wis.). These are hollow glucan particles that are the insoluble waste stream from the yeast extract manufacturing process. During the production of yeast extracts the soluble components of partially autolyzed yeast cells are removed and the insoluble residue is a suitable material for terpene loading. These hollow glucan particles comprise approximately 25-35% beta 1,3-glucan w/w. A key attribute of these materials are that they contain more than 10% lipid w/w and are very effective at absorbing terpenes. In addition, as a waste stream product they are a relatively cheap source of hollow glucan particles.

Alternative hollow glucan particles which have higher purity are those produced by Nutricepts (Nutricepts Inc., Burnsville, Minn.) and ASA Biotech. These particles have been alkali extracted, which removes additional intracellular components as well as removes the outer mannoprotein layer of the cell wall yielding a particle of 50-65% glucan w/w.

Higher purity hollow glucan particles are the WGP particles from Biopolymer Engineering. These particles are acid extracted removing additional yeast components yielding a product 75-85% glucan w/w.

Very high purity hollow glucan particles are Adjuvax™ from Alpha-beta Technology, Inc. (Worcester, Mass.) and microparticulate glucan from Novogen (Stamford, Conn.). These particles are organic solvent extracted which removes residual lipids and so the particles comprise more than 90% glucan w/w.

In some embodiments a high purity glucan particle or cell wall particle may be required, for example where strict control over possible contaminants is required. In these instances the higher purity particles would be preferred over other less pure products. For other embodiments, the less pure particles would be preferred for economic reasons; those particles have also been found to be more effective at absorbing terpenes.

Preferably the hollow glucan particle or cell wall particle has a slight lipid content, such as 1 or 2% w/w lipid. A slight lipid content can increase the ability of the particle to encapsulate the terpene component. Preferably the lipid content of the hollow glucan particle or cell wall particle is 5% w/w or greater, more preferably 10% w/w or greater.

Optionally the terpene component to be encapsulated can be associated with a surfactant. The surfactant can be non-ionic, cationic, or anionic. Examples of suitable surfactants are listed above. The surfactant acts to hold the terpene component in an emulsion and also assists encapsulation of the terpene component into the hollow glucan particle or cell wall particle. The surfactant can also act to modify or control the release characteristics of the terpene from the hollow glycan particle or cell wall particle.

The term "terpene" as used herein refers not only to terpenes of formula $(C_5H_8)_n$, but also encompasses terpene derivatives, such as terpene aldehydes or terpene polymers. Natural and synthetic terpenes are included, for example monoterpenes, sesquiterpenes, diterpenes, triterpenes, and tetraterpenes. In addition, reference to a single name of a compound will encompass the various isomers of that compound. For example, the term citral includes the cis-isomer citral-a (or geranial) and the trans-isomer citral-b (or neral).

In one embodiment the terpene component includes one or more terpenes which contain oxygen. Citral, for example citral 95, is an oxygenated $C_{10}H_{16}$ terpene, $C_{10}H_{16}O$ CAS No. 5392-40-5 (3,7-dimethyl-2,6-octadien-1-al). A stable suspension of citral can be formed up to about 2500 ppm. Citral can be made into a solution at up to about 500 ppm. A stable suspension of hollow glucan particles incorporating citral of 25 ppt citral can be made.

The encapsulated composition according to one aspect of the present invention can comprise 1 to 99% by volume terpenes, 0 to 99% by volume surfactant and 1 to 99% hollow glucan particles or cell wall particles. More specifically the composition can comprise about 10% to about 67% w/w terpenes, about 0.1-10% surfactant and about 40-90% hollow glucan particles or cell wall particles.

Suitably a composition of the present invention comprises from about 500 to about 10,000 ppm hollow glucan particles or cell wall particles, where the particles contain from about 1 to about 67% terpene component. Preferably the composition comprises from about 1000 to about 2000 ppm hollow glucan particles or cell wall particles, where the particles contain from about 10 to about 50% terpene component.

Concentrations of hollow glucan particles or cell wall particles encapsulating terpenes of 1, 5, 10, 20, 30, 40, 50, 60, 70, 80, 90, 100, 110, 125, 130, 140, 150, 160, 175, 190, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1250, 1375, 1425, 1500, 1600, 1750, or 2000 ppm can be used as effective concentrations in the compositions and methods of the current invention. Even higher concentrations (up to 25 ppt, i.e. parts per thousand) can be made and may be useful in the current invention.

The composition of the present invention can comprise between about 1 ppm and about 25 ppt (25000 ppm) of the terpene component, preferably 100 to 2000 ppm of the terpene component, for example, 250, 500, 1000, 2000 ppm thereof.

The terpenes, surfactants, and other components of the invention may be readily purchased or synthesised using techniques generally known to synthetic chemists.

It is highly preferred that terpenes used in the present invention, for safety and regulatory reasons, are at least food grade terpenes (as defined by the United States FDA or equivalent national regulatory body outside the USA).

Optionally the composition can comprise other food-grade active compounds in addition to the terpene component, for example other antimicrobial agents, enzymes, or the like.

Optionally the composition can comprise a further active agent in addition to the terpene component, for example an antimicrobial agent, an anti-fungal agent, an insecticidal agent, an anti-inflammatory agent, an anaesthetic or the like. Suitable agents include:

Anti-fungal: Cell wall hydrolyases (assuming they do not degrade the hollow glucan particle or cell wall particle), cell wall synthesis inhibitors, standard antifungals.

Anti-bacterial: Antiseptics, cell wall hydrolases, synthesis inhibitors, antibiotics.

Insecticidal: Natural insecticides, chitinase.

The composition can comprise an antioxidant to reduce oxidation of the terpene. An example of such an anti-oxidant might be rosemary oil, vitamin C or vitamin E.

The encapsulated composition of the present invention can be in the form of a dry powder. The composition can be provided in combination with an agriculturally, food or pharmaceutically acceptable carrier or excipient in a liquid, solid or gel-like form.

For solid compositions, suitable carriers include pharmaceutical grades of mannitol, lactose, starch, magnesium stearate, sodium saccharin, talc, cellulose, glucose, sucrose, magnesium carbonate, and the like. Suitably the formulation is in tablet or pellet form. As suitable carrier could also be a human or animal food material. Additionally, conventional agricultural carriers could also be used.

A pellet, tablet or other solid form of the composition can preferably also contain a dispersal agent which promotes dispersal of the composition when placed into a liquid, e.g. water. Suitable dispersal agents include xanthan gum, maltodextrin, alginates, or the like.

Liquid compositions can, for example, be prepared by dispersing the composition in water, saline, aqueous dextrose, glycerol, ethanol, or the like, to form a solution or suspension. If desired, these compositions can contain minor amounts of non-toxic auxiliary substances such as wetting or emulsifying agents, pH buffering agents (for example, sodium acetate, sorbitan monolaurate, triethanolamine sodium acetate or triethanolamine oleate). The methods of preparing such liquid compositions are known, or will be apparent, to those skilled in this art; for example see Remington: The Science and Practice of Pharmacy; Lippincott, Williams & Wilkins; (Dec. 15, 2000)—which is incorporated herein by reference. Again a liquid composition could be prepared by dispersing the composition in a liquid human or animal food or drink material. Additionally a suitable liquid agricultural excipient could be used.

For oral administration tablets and granules are generally preferred. Tablets may contain binders and lubricants. Fine powders or granules may contain diluting, dispersing and/or surface active agents and can be presented in water or in a syrup. Capsules or sachets can conveniently contain the composition in a dry state. Non-aqueous solutions or suspensions of the composition are also suitable and may contain suspending agents. Where desirable or necessary, flavouring, preserving, suspending, thickening, or emulsifying agents can be included. Of course, it would be suitable to use a food or drink material as an oral delivery method.

Parenteral administration is generally characterised by injection. For injectables it will be appreciated that, in general, all materials used in the composition and any excipient used must be of pharmaceutical grade. Injectables can be prepared in conventional forms, either as liquid solutions, emulsions or suspensions, solid forms suitable for dissolution, suspension in liquid prior to injection, or as emulsions. An alternative approach for parental administration involves use of a slow release or sustained release system, such that a constant level of dosage is maintained. See, for example, U.S. Pat. No. 3,710,795, which is incorporated by reference herein. Preparations for parenteral administration can also contain buffers, diluents and other suitable additives. Examples of non-aqueous solvents are propylene glycol, polyethylene glycol, vegetable oils (such as olive oil), and injectable organic esters (such as ethyl oleate). Aqueous carriers include water, alcoholic/aqueous solutions, emulsions, or suspensions, including saline and buffered media. Other parenteral vehicles include sodium chloride solution, Ringer's dextrose, dextrose and sodium chloride, lactated Ringer's, or fixed oils. Vehicles for intravenous use include fluid and nutrient replenishers, electrolyte replenishers (such as those based on Ringer's dextrose) and the like.

Preservatives and other additives can also be present such as, for example, antimicrobials, anti-oxidants, chelating agents, inert gases, and the like.

For topical administration liquids, suspension, lotions, creams, gels, ointments, drops, suppositories, sprays and powders may be used. Conventional pharmaceutical carriers, aqueous, powder or oily bases, thickeners, and the like can be used as necessary or desirable.

The present invention further provides a method of preparing a hollow glucan particle or cell wall particle encapsulating a terpene component, said method comprising the steps of;

a) providing a terpene component;
    b) providing a hollow glucan particle or cell wall particle;
    c) incubating the terpene component with the glucan particle or cell wall particle under suitable conditions for terpene encapsulation; and
    d) recovering the hollow glucan particle or cell wall particle encapsulating the terpene component.

Optionally the above method can further comprise the step of drying the particles encapsulating the terpene component. Drying may be achieved in a number of ways and mention may be made of freeze drying, fluidised bed drying, drum drying or spray drying, all of which are well known processes.

In step a) of the above method, the terpene component is suitably provided as a suspension in an aqueous solvent, and optionally in the presence of a surfactant. Suitably the solvent is water. A suitable surfactant is Tween-80 (polyoxyethylenesorbitan monooleate), and preferably the surfactant is present at a concentration of about 0.1 to 10% by volume of the total reaction mixture, more preferably about 1%. Alternatively the terpene component may be provided as a true solution in a solvent, e.g. water. A true solution of terpene in water can be obtained by mixing the terpene in water at high shear until a true solution is obtained. Publication No WO 03/020024 provides further details of forming true solutions of terpenes in water.

In step b) of the above method, the hollow glucan particle or cell wall particle is suitably provided as a suspension in water or other suitable liquid. Suitably the suspension comprises approximately 1 to 1000 mg particles per ml, preferably 200 to 400 mg/ml. Alternatively the particles may be provided as a dry powder and added to the terpene-surfactant suspension.

Alternatively the particles are provided in sufficient liquid to minimally hydrate the particles, but not in significant excess. The term "hydrodynamic volume" (HV) is used to describe the volume of liquid required to minimally hydrate the particles. Thus suitably the particles are provided with a volume ranging from the HV and a volume of 1.5 times the HV (1.5HV). This makes the subsequent drying step more efficient. Also, where a low volume of liquid is used (ie. around HV to 1.5HV), it is also possible to extrude the finished product into pellet or noodle form, which is convenient for fluidised bed drying.

It has been found that the terpene component can become encapsulated by the hollow glucan particle or cell wall particle at room temperature. The rate of encapsulation is, however, increased at 37° C. or above but the temperature should be kept below the boiling point or denaturing temperature of any component of the composition. Suitable conditions for step c) of the above method are therefore atmospheric pressure at a temperature of 20 to 37° C. (however, a higher temperature may be used). Optimisation of the conditions for a particular encapsulation reaction will be a matter of routine experimentation.

The present invention further provides a method of killing a microorganism, said method comprising the step of;
a) contacting said microorganism with a composition comprising a terpene component, the terpene component comprising a mixture of more than one terpene selected from the group consisting of thymol, eugenol, geraniol and citral.

Suitable compositions for use in this method are set out above.

In one aspect the present invention provides a method of treating or preventing infection of a plant, said method comprising the step of;
a) administering in a therapeutically effective dose a composition comprising a terpene component, the terpene component comprising a mixture of more than one terpene selected from the group consisting of thymol, eugenol, geraniol and citral to the plant or to soil in proximity to the plant.

In one embodiment the present invention provides a method of treating or preventing a bacterial plant infection. Bacterial plant infections include *Erwinia amylovora* (fire blight of apple), *Pseudomonas syringae* pv. *phaseolicola* (halo blight of bean) and *Xanthomonas campestris* pv. *phaseoli* (common blight of bean). The present invention accordingly represents a significant advance as currently no compositions or methods are available which can satisfactorily treat or prevent such bacterial plant infections.

In another embodiment the present invention provides a method of treating or preventing a fungal/oomycete plant infection, especially those affecting the surface of a plant. Such infections include downy mildew (*Plasmopara viticola*), powdery mildew (*Unicinula necator*) or botrytis bunch rot (*Botrytis cinerea*); these infections particularly affect grape vines.

Compositions comprising a terpene component comprising a mixture of more than one terpene selected from the group consisting of thymol, eugenol, geraniol and citral have been shown to be effective in treating plant infections. In particular, compositions comprising a terpene component comprising a combination of thymol and one or more of eugenol, geraniol, citral have been shown to be particularly effective in treating a broad spectrum of plant infections.

Compositions comprising the following terpene components have been shown to be particularly effective in treating or preventing bacterial plant infections:
thymol and citral;
thymol and geraniol; or
thymol and eugenol.

Compositions comprising the following terpene components have been shown to be particularly effective in treating or preventing fungal/oomycete plant infections:
thymol and geraniol;
thymol and eugenol; or
thymol, eugenol and citral.

Other compositions which have been shown to be highly effective in treating and preventing plant infections in general include the following terpene components:
Thymol, geraniol and citral;
Thymol, geraniol and eugenol; or
Geraniol, thymol, eugenol and citral.

Of particular interest in the control of plant diseases are compositions which can prevent or treat a broad range of plant diseases. In this regard the following compositions have been shown to be particularly effective:
thymol and citral;
thymol and geraniol; or
thymol and eugenol.

The present invention further provides the use of any of the above compositions in the treatment or prevention of a plant infection.

Other plant infection that may be treated or prevented in accordance with the present invention may be caused by one or more of the following: *Aspergillius fumigatus, Sclerotinia homeocarpa, Rhizoctonia solani, Colletotrichum graminicola Phytophtora infestans* or *Penicillium* sp. Terpenes alone in suspension or solution, however, are somewhat unstable and can degrade rapidly in the soil environment, thus losing efficacy. Incorporation of a terpene component in a hollow glucan particle or cell wall particle can reduce the rate of terpene release and degradation, thus increasing the duration of action of the terpene in the soil or on the plant. Accordingly it is preferred that the terpene component is encapsulated as detailed above.

An advantage of a terpene based treatment of plants is that it can be applied shortly before harvest.

Many conventional treatments require an extended period before re-entry to the treated area (generally 3 weeks). This means that an outbreak of a plant disease shortly before harvest cannot be treated with conventional treatments as it would then not be possible to harvest the crop at the desired time. The compositions of the present invention can suitably be applied at any time up until harvest, for example 21 days prior to harvest, 14 days prior to harvest, 7 days prior to harvest, or even 3 days or less before harvest.

Prevention of plant infections can be achieved by treating plants which the compositions of the present invention regularly as a prophylactic measure.

Suitably the composition of the present invention is applied by spraying. This is particularly suitable for treating a plant disease which affects the surface of a plant. For spraying, a preparation comprising 2 g/l of the composition in water may be used. Concentrations of from 2 to 4 g/l are particularly effective, and concentrations of greater than 4 g/l can be used as required. Obviously it is important that the concentration of the composition used is sufficient to kill or inhibit the disease causing agent, but not so high as to harm the plant being treated.

When spraying plants a rate of 100 L/Ha or higher may generally be suitable to cover the plant. Typically a rate of 100 to 500 L/Ha may be sufficient for crops of small plants which do not have extensive foliage; though higher rates may of course also be used as required. For larger plants with extensive foliage (e.g. perennial crop plants such as vines or other fruit plants) rates of 500 L/Ha or greater are generally suitable to cover the plants. Preferably a rate of 900 L/Ha or greater, more preferably 1200 L/Ha or greater is used to ensure good coverage. Where grape vines are being treated, a rate of 1200 L/Ha has proven suitably effective.

The composition of the present invention may alternatively be applied via irrigation. This is particularly suitable for treating nematodes or other soil borne pathogens or parasites.

The present invention further provides a method of preventing or treating an infection in a patient, said method comprising the step of;
  a) administering to said patient in a therapeutically effective dose, a composition comprising a terpene component, the terpene component comprising a mixture of more than one terpene selected from the group consisting of thymol, eugenol, geraniol and citral to the plant or to soil in proximity to the plant.

Suitable compositions are those defined in more detail above.

The infection of the patient may be caused by any infectious agent. Examples of these infectious agents include, but are not restricted to *Staphylococcus aureus, Aspergillius fumigatus, Mycoplasma iowae, Penicillium* sp., and *Mycoplasma pneumoniae*.

For internal administration the composition may be administered orally, vaginally, rectally, by inhalation, or by parenteral routes, e.g. by intradermal, subcutaneous, intramuscular, intraperitoneal, intrarectal, intraarterial, intralymphatic, intravenous, intrathecal and intratracheal routes. Suitable formulations of the composition for these routes are discussed above.

For external treatment, the composition may be applied topically, for example as a cream or ointment or as a dry powder for treatment of a wound.

The amount of terpene administered in the above method should clearly be sufficient to achieve the desired result, i.e. prevention and/or treatment of the infection, but should not be at a level which will induce serious toxic effects in the patient.

The amount of composition administered will, of course, be dependent on the manner of administration, on the patient being treated, i.e. their weight, their age, condition, sex and extent of the disease in the subject and on the judgement of the prescribing physician. The dose, schedule of doses, and route of administration can be varied. One of skill in the art would readily be able to determine an anti-infective amount for a given application based on the general knowledge in the art and the procedures in the Examples given below. It should be noted that the term "patient" as used herein refers to any individual, either human or animal, to which the treatment is applied. Thus, the patient can be a domesticated animal (e.g., cat, dog, etc.), livestock (e.g., cattle, horse, pig, sheep, goat, etc.), laboratory animal (e.g., mouse, rabbit, rat, guinea pig, etc.), birds and fish. Suitably the subject is a mammal and especially a primate, for example a human.

In another embodiment the present invention provides a method of killing insects or arachnids, said method comprising the step of;
  a) administering to said insect or arachnid in an effective dose a composition comprising terpene component, the terpene component comprising a mixture of more than 1 terpene selected from the group consisting of thimol, eugenol, geraniol and citral.

Insects which may be killed accordingly to the present invention include, for example, ants, termites, lice, aphids, fleas, locusts, grasshoppers and thrips. Arachnids which may be killed according to the present invention include, for example, mites, spiders and ticks.

In a further embodiment the present invention also provides a composition comprising a terpene component as set out above in the prevention or treatment of an infection in a patient or a plant. Suitable compositions are those defined in more detail above.

In a further embodiment the present invention provides the use of a composition comprising a terpene component as set out above in the manufacture of a medicament for the treatment of infection caused by a micro-organism. Suitable compositions are those defined in more detail above.

The present invention will now by further described with reference to the following, non-limiting, examples and figures in which:

FIG. 19 represents a light micrograph as in FIG. 13 where 2.2 g of 1% xanthan gum is included.

FIG. 20 represents a light micrograph as in FIG. 13 where 4.4 g of 1% xanthan gum is included.

FIG. 21 shows a schematic representation of treatment areas on sites 18 and 20.

FIG. 22 shows a schematic representation of treatment areas on sites 18 and 20.

FIG. 23 shows a schematic representation of the treatment areas on site 7.

FIG. 26a-d shows a graph representing mite disease ratings in 4 replicates of tomato plants.

Figure 27:
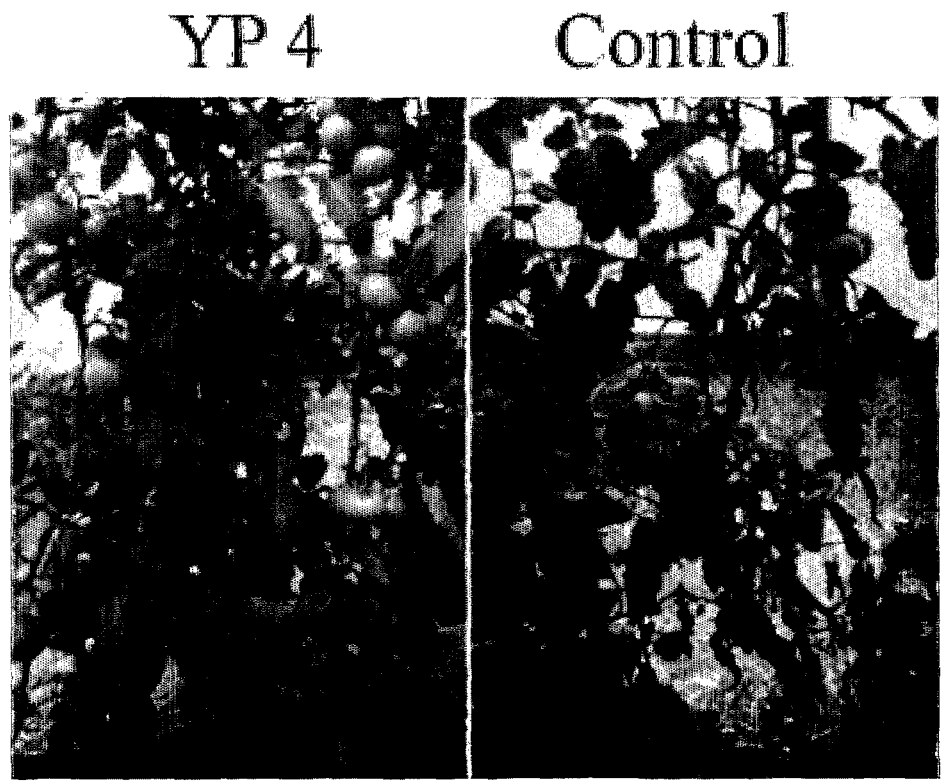

FIG. 27 is a photograph showing a comparison between a plant treated with YP-4 and a control.

The following examples are provided to further enable those of ordinary skill in the art to make or perform the present invention. They are purely exemplary and are not intended to limit the scope of the invention. Unless indicated otherwise, parts are parts by volume or parts by weight, as indicated, temperature is in degrees Celsius (° C.) or is at ambient temperature, and pressure is at or near atmospheric. There are numerous variations and combinations of the compositions and conditions for making or using them, e.g., component concentrations, desired solvents, solvent mixtures, temperatures, pressures, and other ranges and conditions that can be used to optimise the results obtained from the described compositions and methods. Only reasonable and routine experimentation will be required to optimise these.

EXAMPLE 1

Demonstration of Terpene Loading into Baker's Yeast Particles and Purified Yeast Glucan Particles The following protocol was performed to demonstrate that terpenes would load into yeast cell walls and other hollow glucan particles.

Emulsions of citral and L-carvone were prepared by mixing 150 µl of the terpene with 100 µl of 10% Tween 80 in water and 250 µl of water.

Baker's yeast particles (YP) or Levacan™ yeast glucan particles (YGP), available from Savory Systems International, Inc., Branchburg, N.J., were mixed with water to form a 250 mg/ml suspension.

500 µl of the YP or YGP suspension and 250 µl of the terpene emulsion were mixed together and incubated overnight under constant agitation. 500 µl YP or YGP suspension and 500 µl of water were used as a control. The particles were then washed with water until free from external emulsion. The particle preparations were then frozen and lyophilised until dry.

The particles were then rehydrated and examined under light microscope. The results are shown in FIGS. 1 to 4.

Figure 1:
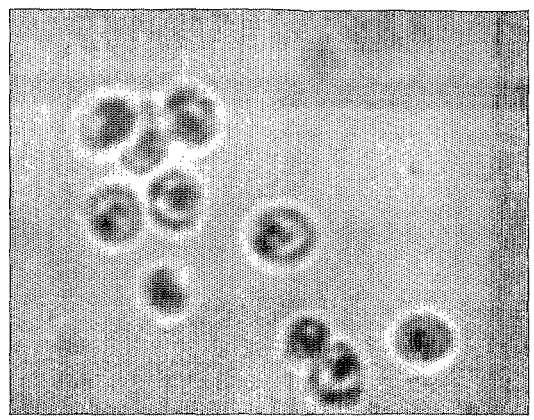
FIG. 1 represents a light micrograph of empty yeast cell walls.
Figure 2:
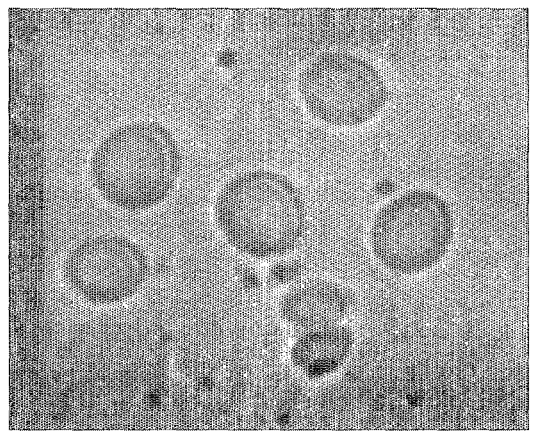
FIG. 2 represents a light micrograph of yeast cell walls encapsulating L-carvone.
Figure 3:
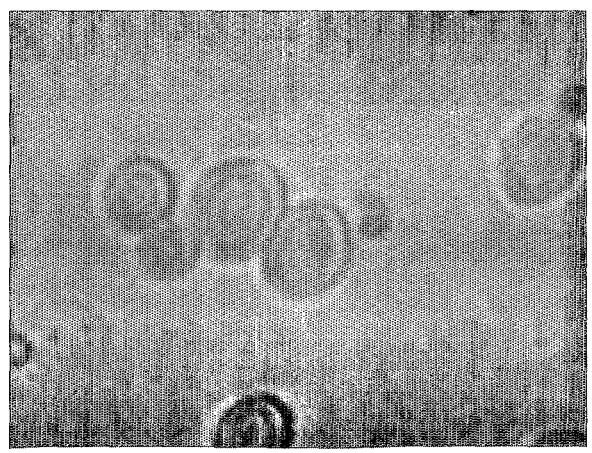
FIG. 3 represents a light micrograph of yeast cell walls encapsulating citral.
Figure 4:
FIG. 4 represents a light micrograph of terpene emulsion.
Figure 5:
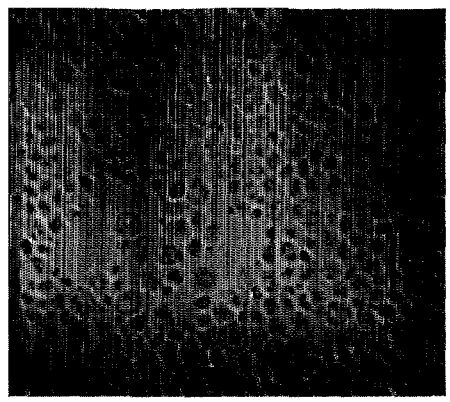
FIG. 5 represents a light micrograph of yeast cell walls in hydrodynamic volume (HV) water.
Figure 6:
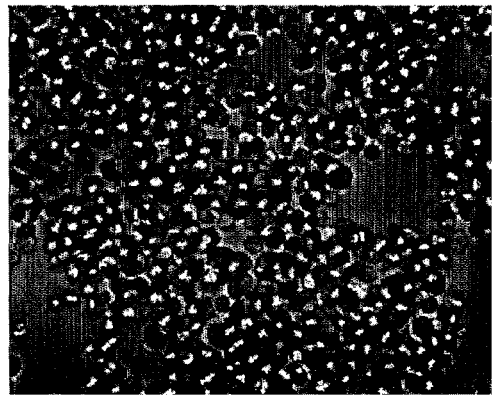
FIG. 6 represents a light micrograph of yeast cell walls encapsulating terpene in 5 times hydrodynamic volume (HV) of water.

FIG. 1 shows spherical structures with a dark area at their centre, these are empty hollow glucan particles. FIGS. 2 and 3 shows spherical structures with a swollen appearance with a light coloured interior, these are particles with terpene encapsulated in the central cavity—citral in FIG. 2 and L-carvone in FIG. 3. In FIGS. 2 and 3 small blobs of free terpene can also be seen, e.g. at the top of FIG. 2, just left of centre. FIG. 4 shows the terpene emulsion as small blebs of terpene suspended in water.

EXAMPLE 2

Determination of Maximal Citral and L-Carvone Loading Levels in Baker's Yeast Cell Wall Particles (YP)

The following protocol was performed to determine the maximal amounts of terpenes that would load into YP.

L-carvone and citral emulsions were prepared by sonicating 4.5 g of the terpene with 0.3 ml water.

10% Tween-80 solution was prepared by sonicating 4.5 g Tween-80 in 40.5 mls water.

YP suspension was prepared by mixing YP with water to form 20 mg/ml suspension.

Encapsulation reactions were set up as described in Table 1.

Citral or L-carvone-water emulsion was mixed with YP and Tween 80 surfactant overnight at room temperature. Samples were centrifuged at 14,000×g for 10 minutes and the appearance of free terpene floating on the aqueous layer was scored. The results are shown in the right hand column labelled free terpene of Table 1.

The expression "free terpene" refers to the visible presence of terpene in the centrifuged reaction mixture. The absence of free terpene indicates complete absorption of the terpene by the particles. The highest volume of terpene absorbed by the particles, as evidenced by the absence of free terpene, was recorded as the maximal volume of absorbed terpene emulsion.

TABLE 1

| Tube | 20 mg/ml YP µl | Terpene Emulsion | Vol µl | 10% Tween-80 µl | Free Terpene |
|---|---|---|---|---|---|
| 1 | 500 | — | — | 500 | − |
| 2 | 500 | L-carvone | 0.5 | 500 | − |
| 3 | 500 | L-carvone | 1.65 | 500 | − |
| 4 | 500 | L-carvone | 5 | 495 | − |
| 5 | 500 | L-carvone | 16.5 | 483.5 | − |
| 6 | 500 | L-carvone | 50 | 450 | + |
| 7 | 500 | L-carvone | 165 | 335 | + |
| 8 | 500 | L-carvone | 500 | — | + |
| 9 | 500 | Citral | 0.5 | 500 | − |
| 10 | 500 | Citral | 1.65 | 500 | − |
| 11 | 500 | Citral | 5 | 495 | − |
| 12 | 500 | Citral | 16.5 | 483.5 | +/− |
| 13 | 500 | Citral | 50 | 450 | + |
| 14 | 500 | Citral | 165 | 335 | + |
| 15 | 500 | Citral | 500 | — | + |

As can be seen from the results, YP is capable of absorbing and encapsulating at least 16.5 µl of L-carvone terpene emulsion or at least 5 µl of citral emulsion per 10 mg of YP.

EXAMPLE 3

Demonstration of Improved Terpene Loading with Surfactant and Determination of Optimal Tween-80:Terpene Ratio The following protocol was performed to demonstrate that the presence of surfactant improves terpene loading and to determine the minimum level of Tween-80 surfactant required for the YP terpene loading reaction.

L-carvone and citral emulsions were prepared by sonicating 4.5 g of the terpene with 0.3 ml water.

10% Tween-80 solution was prepared by sonicating 4.5 g Tween-80 in 40.5 ml water.

Baker's YP suspension was prepared by mixing YP with water to form 250 mg/ml suspension.

Loading reactions were set up as shown in Table 2 below.

Citral or L-carvone-water emulsion was mixed with YP with 0-10% v/v Tween 80 surfactant overnight at room temperature. Samples were centrifuged at 14,000×g for 10 minutes and the appearance of free terpene floating on the aqueous layer was scored. The results are shown in the right hand column labelled free terpene of Table 2.

The expression "free terpene" refers to the visible presence of terpene in the centrifuged reaction mixture. The absence of free terpene indicates complete absorption and encapsulation of the terpene by the YP. The highest volume of terpene absorbed by the YP, as evidenced by the absence of free terpene, was recorded as the maximal volume of absorbed terpene emulsion.

TABLE 2

| Tube | 250 mg/ml YP Ml | Terpene Emulsion | Vol μl | 10% Tween-80 μl | Water μl | Free Terpene |
|---|---|---|---|---|---|---|
| 1 | 500 | — | — | — | 500 | – |
| 2 | 500 | L-carvone | 150 | 0 | 350 | Sl |
| 3 | 500 | L-carvone | 150 | 5 | 345 | Sl |
| 4 | 500 | L-carvone | 150 | 10 | 340 | Sl |
| 5 | 500 | L-carvone | 150 | 33 | 317 | Sl |
| 6 | 500 | L-carvone | 150 | 100 | 250 | – |
| 7 | 500 | L-carvone | 150 | 200 | 150 | – |
| 8 | 500 | L-carvone | 150 | 350 | — | – |
| 9 | 500 | L-carvone | 400 | 0 | 100 | ++ |
| 10 | 500 | L-carvone | 400 | 5 | 95 | ++ |
| 11 | 500 | L-carvone | 400 | 10 | 90 | ++ |
| 12 | 500 | L-carvone | 400 | 33 | 77 | ++ |
| 13 | 500 | L-carvone | 400 | 100 | — | + |
| 14 | 500 | L-carvone | 400 | 20 μl 100% | 30 | + |
| 15 | 500 | Citral | 113 | 0 | 387 | + |
| 16 | 500 | Citral | 113 | 5 | 382 | + |
| 17 | 500 | Citral | 113 | 10 | 377 | + |
| 18 | 500 | Citral | 113 | 33 | 354 | Sl |
| 19 | 500 | Citral | 113 | 100 | 287 | Sl |
| 20 | 500 | Citral | 113 | 200 | 187 | – |
| 21 | 500 | Citral | 113 | 350 | 37 | – |
| 22 | 500 | Citral | 250 | 0 | 250 | ++ |
| 23 | 500 | Citral | 250 | 5 | 245 | ++ |
| 24 | 500 | Citral | 250 | 10 | 240 | ++ |
| 25 | 500 | Citral | 250 | 33 | 217 | + |
| 26 | 500 | Citral | 250 | 100 | 150 | + |
| 27 | 500 | Citral | 250 | 20 μl 100% | 230 | + |

Sl = slight

As can be seen from the results a Tween-80 concentration of 1% (i.e. 100 μl of 10% Tween-80 in 1000 μl of reaction mixture) is sufficient to allow complete uptake of the terpene in the above reaction. A 2% Tween-80 causes no improvement in results, whereas with a 0.33% concentration free terpene was observed. This indicates that:

Terpenes are absorbed into YP particles in the absence of a surfactant, but the presence of surfactant significantly increases terpene absorption.

A Tween-80 concentration of around 1% is optimum for YP loading as it ensures proper loading whilst maximising the terpene payload of the YP particles.

EXAMPLE 4

Determination of Maximal Terpene Loading and Encapsulation at High Baker's Yeast Cell Wall Particles (YP) Levels The following protocol was performed to determine the maximal amounts of terpenes that would load into YP at high YP levels.

L-carvone and citral emulsions were prepared by sonicating 4.5 g of the terpene with 3 ml 1% Tween.

5% Tween-80 solution was prepared by sonicating 0.5 g Tween-80 in 9.5 ml water.

YP suspension was prepared by mixing YP with water to form 250 mg/ml suspension.

Encapsulation reactions were set up as shown in Table 3.

Citral or L-carvone-water emulsion was mixed with YP and Tween 80 surfactant overnight at room temperature. Samples were centrifuged at 14,000×g for 10 minutes and the appearance of free terpene floating on the aqueous layer was scored. The results are shown in the right hand column labelled free terpene of Table 3.

The expression "free terpene" refers to the visible presence of terpene in the centrifuged reaction mixture. The absence of free terpene indicates complete absorption of the terpene by the YP. The highest volume of terpene absorbed by the YP, as evidenced by the absence of free terpene, was recorded as the maximal volume of absorbed terpene emulsion.

TABLE 3

| Tube | 250 mg/ml YP μl | Terpene Emulsion | Vol μl | 1% Tween-80 μl | Free Terpene |
|---|---|---|---|---|---|
| 1 | 500 | — | — | 500 | – |
| 2 | 500 | L-carvone | 15 | 485 | – |
| 3 | 500 | L-carvone | 37.5 | 462.5 | – |
| 4 | 500 | L-carvone | 75 | 425 | – |
| 5 | 500 | L-carvone | 112.5 | 387.5 | – |
| 6 | 500 | L-carvone | 150 | 350 | Sl+ |
| 7 | 500 | L-carvone | 225 | 275 | + |
| 8 | 500 | L-carvone | 450 | 50 | + |
| 9 | 500 | Citral | 15 | 485 | – |
| 10 | 500 | Citral | 37.5 | 462.5 | – |
| 11 | 500 | Citral | 75 | 425 | – |
| 12 | 500 | Citral | 112.5 | 387.5 | Sl+ |
| 13 | 500 | Citral | 150 | 350 | + |
| 14 | 500 | Citral | 225 | 275 | + |
| 15 | 500 | Citral | 450 | 50 | + |

As can be seen from the results in Table 3, YP is capable of absorbing and encapsulating terpenes at high YP concentration. YP absorbed and encapsulated at least 112.5 μl of L-carvone terpene emulsion or at least 75 μl of citral emulsion per 125 mg of YP. This demonstrates that the terpene encapsulation reaction is independent of YP concentration within the ranges tested.

EXAMPLE 5

Screen Commercially Available Particles for Terpene Absorption

The following protocol was performed to analyse the loading properties of different types of particles. The particles studied were Baker's Yeast Cell Wall Particles (Sigma Chemical Corp., St. Louis, Mo.), Nutrex™ Walls (Sensient Technologies, Milwaukee, Wis.), SAF-Mannan™ (SAF Agri, Minneapolis, Minn.), Nutricept Walls™ (Nutricepts Inc., Burnsville, Minn.), Levacan™ (Savory Systems International, Inc., Branchburg, N.J.) and WGP™ (Alpha-beta Technology, Inc. Worcester, Mass.).

L-carvone and citral emulsions were prepared by sonicating 7 g terpene+3 ml 3.3% Tween-80.

Table 4 below compares the purity with the number of yeast particles per mg and the packed solids weight/volume ratio.

TABLE 4

| Yeast Particle | Purity % Beta 1,3-glucan | No. particles/mg | Mg particles/ml |
|---|---|---|---|
| Bakers | 11.2 | $4 \times 10^7$ | 250 |
| Nutrex | 24.5 | $1.7 \times 10^8$ | 58.8 |
| SAF Mannan | 33.4 | $2.4 \times 10^8$ | 41.7 |
| Nutricepts | 55.7 | $5.2 \times 10^8$ | 37 |
| Levacan | 74.6 | $1 \times 10^8$ | 19.2 |
| WGP | 82.1 | $3.5 \times 10^8$ | 10 |

From Table 4 it can be concluded that the number of particles per mg is inversely proportional to purity. Thus the number of particles per mg of WGP is almost 10-fold higher than Baker's YP.

The YP Suspensions were Prepared as Follows:
- Baker's yeast cell wall particle suspension (YP) was prepared by mixing 250 mg YP/ml 1% Tween 80.
- Nutrex suspension was prepared by mixing 163 mg Nutrex YGP/ml 1% Tween 80.
- SAF Mannan suspension was prepared by mixing 234 mg Biospringer YGP/ml 1% Tween 80.
- Nutricepts suspension was prepared by mixing 99 mg Nutricepts YGP/ml 1% Tween 80.
- Levacan suspension was prepared by mixing 217 mg Lev YGP/ml 1% Tween 80.
- WGP suspension was prepared by mixing 121 mg WGP YGP/ml 1% Tween 80.

The packed volume of the above particles is identical which means that equal numbers of particles were assayed.

Loading reactions were set up as shown in Table 5 and left to incubate overnight. Samples were centrifuged at 14,000×g for 10 minutes and the appearance of free terpene floating on the aqueous layer and the color of the encapsulated terpenes in the pellet was scored. The results are shown in the two right hand columns of Table 5. The highest volume of terpene absorbed by particles as evidenced by the absence of free terpene was recorded as the volume of absorbed terpene emulsion.

TABLE 5

| Tube | Particle | conc mg/ml | μl | Terpene Emulsion | Vol μl | 1% Tween 80 μl | Free Terpene | Colour |
|---|---|---|---|---|---|---|---|---|
| 1 | Baker's | 250 | 500 | L-carvone | 125 | 375 | – | W |
| 2 | Nutrex | 163 | 500 | L-carvone | 125 | 375 | – | W |
| 3 | SAF Mannan | 234 | 500 | L-carvone | 125 | 375 | – | W |
| 4 | Nutricepts | 99 | 500 | L-carvone | 125 | 375 | + | W |
| 5 | Levacan | 217 | 500 | L-carvone | 125 | 375 | + | W |
| 6 | WGP | 121 | 500 | L-carvone | 125 | 375 | + | W |
| 7 | Baker's | 250 | 500 | Citral | 100 | 375 | – | Y |
| 8 | Nutrex | 163 | 500 | Citral | 100 | 375 | – | Y |
| 9 | SAF Mannan | 234 | 500 | Citral | 100 | 375 | – | W |
| 10 | Nutricepts | 99 | 500 | Citral | 100 | 375 | + | Y |
| 11 | Levacan | 217 | 500 | Citral | 100 | 375 | + | int |
| 12 | WGP | 121 | 500 | Citral | 100 | 375 | + | int |
| 13 | — | — | — | L-carvone | 125 | 875 | + | — |
| 14 | — | — | — | Citral | 100 | 900 | + | Y |

W = white;
Y = yellow;
sl = slight;
int = intermediate

From the results the following conclusions were reached:
1. Purified particles with a low lipid content were less effective at absorbing terpenes.
2. Less pure particles were more effective at absorbing terpenes
3. Yellow degradation product of citral was not formed when encapsulated in SAF-Mannan™.
4. Based on qualitative loading at the single terpene level tested, SAF Mannan™ appears to be best, Nutrex™ second and Baker's third.

EXAMPLE 6

Kinetics of Terpene Loading into Various Types of Particles and Different Incubation Temperatures The following protocol was adopted to compare the loading kinetics of various types of yeast particles.

L-carvone and citral emulsions were prepared by sonicating 7 g terpene with 3 ml 3.3% Tween-80.

1% Tween-80 solution was prepared by sonicating 1 ml 10% Tween-80 in 10 ml water.

Baker's YP was prepared by mixing 5 g of bakers YP in 20 ml 1% Tween-80.

Nutrex™ YGP suspension was prepared by mixing 2 g Nutrex™ YGP in 20 ml 1% Tween-80.

SAF Mannan™ suspension was prepared by mixing 2 g SAF Mannan™ in 20 ml 1% Tween-80.

Loading reactions were set up as shown in Table 6.

The reactions were incubated for 1, 3, 6, 9 and 24 hours at room temperature or 37° C. After incubation samples were centrifuged at 14,000×g for 10 minutes and the appearance of free terpene floating on the aqueous layer was scored. The results are shown in the two right hand columns of Table 6. The highest volume of terpene absorbed by the particles as evidenced by the absence of free terpene was recorded as the volume of absorbed terpene emulsion. Colour of the encapsulated pellet was scored at 24 hours.

TABLE 6

| Tube | T °C. | Particle | conc mg/ml | μl | Terpene Emulsion | Vol μl | 1% Tween-80 | Free Terpene (hr) 1 | 3 | 6 | 9 | 24 | Color |
|---|---|---|---|---|---|---|---|---|---|---|---|---|---|
| 1 | Rt | Bakers | 250 | 3500 | L-carvone | 788 | 2712 | + | − | − | − | − | W |
| 2 | 37 | Bakers | 250 | 3500 | L-carvone | 788 | 2712 | + | − | − | − | − | W |
| 3 | Rt | Nutrex | 100 | 3500 | L-carvone | 1050 | 2450 | + | − | − | − | − | W |
| 4 | 37 | Nutrex | 100 | 3500 | L-carvone | 1050 | 2450 | + | − | − | − | − | W |
| 5 | Rt | SAF | 100 | 3500 | L-carvone | 1050 | 2450 | <+ | − | − | − | − | W |
| 6 | 37 | SAF | 100 | 3500 | L-carvone | 1050 | 2450 | <+ | − | − | − | − | W |
| 7 | Rt | Bakers | 250 | 3500 | Citral | 525 | 2975 | + | − | − | − | − | Y |
| 8 | 37 | Bakers | 250 | 3500 | Citral | 525 | 2975 | + | − | − | − | − | VY |
| 9 | Rt | Nutrex | 100 | 3500 | Citral | 788 | 2712 | + | − | − | − | − | Y |
| 10 | 37 | Nutrex | 100 | 3500 | Citral | 788 | 2712 | + | − | − | − | − | VY |
| 11 | Rt | SAF | 100 | 3500 | Citral | 788 | 2712 | + | − | − | − | − | W |
| 12 | 37 | SAF | 100 | 3500 | Citral | 788 | 2712 | + | − | − | − | − | W |

White, W;
Yellow, Y;
Very Yellow, VY;
Room Temperature, Rt

From the results shown in Table 6 and other observations the following conclusions can be made:

Terpene loading occurs faster at 37° C. than at room temperature.

SAF Mannan™ Terpene loading reaction takes between 1 and 3 hours.

appears to be preferable particles for two reasons:

Faster and more complete uptake of both terpenes.

Citral remains stable when loaded as evidenced by the absence of yellow colour, characteristic of citral degradation, after 24 hours at 37° C.

EXAMPLE 7

Screen a Range of Single Terpenes and Terpene Combinations for Particle Loading The following protocol was adopted to compare the loading efficiency of Baker's YP versus SAF Mannan™.

Terpene emulsions were prepared as follows:

L-carvone—4.5 g L-carvone in 1.5 ml 3.3% Tween-80.

Citral—4.5 g citral in 1.5 ml 3.3% Tween-80.

Thymol/L-carvone mixture (T/L)—2.25 g thymol and 2.25 g L-carvone in 1.5 ml 3.3% Tween-80.

Eugenol—4.5 g eugenol in 1.5 ml 3.3% Tween-80.

Geraniol—4.5 g geraniol in 1.5 ml 3.3% Tween-80.

Citral/L-carvone/Eugenol mixture (C/L/E)—1.5 g citral, 1.5 g L-carvone, 1.5 g eugenol in 1.5 ml 3.3% Tween-80.

Emulsions composed of terpene:water:surfactant ratio of 0.75:0.3:0.05 were used for these experiments.

Increasing volumes of terpene emulsion were mixed with 250 mg/ml Baker's YP or 250 mg/ml SAF Mannan™ overnight at room temperature as shown in Tables 7 and 8. Samples were centrifuged at 14,000×g for 10 minutes and the appearance of free terpene floating on the aqueous layer was scored. The highest volume of terpene emulsion absorbed by Baker's YP or SAF Mannan™ as evidenced by the absence of free terpene was recorded as the volume of absorbed terpene emulsion. Colour of encapsulated terpenes in the pellet was recorded. The results in Tables 7 and 8 show that all single and terpene combinations were efficiently loaded into both Baker's YP or SAF Mannan particles.

TABLE 7

Evaluation of Baker's YP Loading of Different Terpenes and Terpene Mixtures.

| Tube | Baker (μl) | Terpene Emulsion | Vol (μl) | 1% Tween-80 (μl) | Free Terpene | Colour |
|---|---|---|---|---|---|---|
| 1 | 500 | — | — | 500 | − | W |
| 2 | 500 | L-carvone | 15 | 485 | − | W |
| 3 | 500 | L-carvone | 37.5 | 462.5 | − | W |
| 4 | 500 | L-carvone | 7 | 425 | +/− | W |
| 5 | 500 | L-carvone | 112.5 | 387.5 | +/− | W |
| 6 | 500 | L-carvone | 150 | 350 | + | W |
| 7 | 500 | L-carvone | 225 | 275 | + | W |
| 8 | 500 | L-carvone | 450 | 50 | ++ | W |
| 9 | 500 | Citral | 15 | 485 | − | Y |
| 10 | 500 | Citral | 37.5 | 462.5 | − | Y |
| 11 | 500 | Citral | 75 | 425 | − | Y |
| 12 | 500 | Citral | 112.5 | 387.5 | +/− | Y |
| 13 | 500 | Citral | 150 | 350 | + | Y |
| 14 | 500 | Citral | 225 | 275 | + | Y |
| 15 | 500 | Citral | 450 | 50 | + | Y |
| 16 | 500 | T/L | 15 | 485 | − | W |
| 17 | 500 | T/L | 37.5 | 462.5 | − | W |
| 18 | 500 | T/L | 75 | 425 | − | W |
| 19 | 500 | T/L | 112.5 | 387.5 | +/− | W |
| 20 | 500 | T/L | 150 | 350 | + | W |
| 21 | 500 | T/L | 225 | 275 | + | W |
| 22 | 500 | T/L | 450 | 50 | + | W |
| 23 | 500 | Eugenol | 15 | 485 | − | W |
| 24 | 500 | Eugenol | 37.5 | 462.5 | − | W |
| 25 | 500 | Eugenol | 75 | 425 | − | W |
| 26 | 500 | Eugenol | 112.5 | 387.5 | +/− | W |
| 27 | 500 | Eugenol | 150 | 350 | + | W |
| 28 | 500 | Eugenol | 225 | 275 | + | W |
| 29 | 500 | Eugenol | 450 | 50 | + | W |
| 30 | 500 | Geraniol | 15 | 485 | − | W |
| 31 | 500 | Geraniol | 37.5 | 462.5 | − | W |
| 32 | 500 | Geraniol | 75 | 425 | − | W |
| 33 | 500 | Geraniol | 112.5 | 387.5 | + | W |
| 34 | 500 | Geraniol | 150 | 350 | + | W |
| 35 | 500 | Geraniol | 225 | 275 | + | W |
| 36 | 500 | Geraniol | 450 | 50 | + | W |
| 37 | 500 | C/L/E | 15 | 485 | − | Y |
| 38 | 500 | C/L/E | 37.5 | 462.5 | − | Y |
| 39 | 500 | C/L/E | 75 | 425 | − | Y |
| 40 | 500 | C/L/E | 112.5 | 387.5 | +/− | Y |
| 41 | 500 | C/L/E | 150 | 350 | + | Y |
| 42 | 500 | C/L/E | 225 | 275 | + | Y |
| 43 | 500 | C/L/E | 450 | 50 | + | Y |

TABLE 8

Evaluation of SAF Mannan Loading of Different Terpenes and Terpene Mixtures.

| Tube | SAF (µl) | Terpene Emulsion | Vol | 1% Tween-80 (µl) | Free Terpene | Colour |
|---|---|---|---|---|---|---|
| 1 | 500 | — | — | 500 | − | W |
| 2 | 500 | L-carvone | 15 | 485 | − | W |
| 3 | 500 | L-carvone | 37.5 | 462.5 | − | W |
| 4 | 500 | L-carvone | 75 | 425 | − | W |
| 5 | 500 | L-carvone | 112.5 | 387.5 | − | W |
| 6 | 500 | L-carvone | 150 | 350 | +/− | W |
| 7 | 500 | L-carvone | 225 | 275 | +/− | W |
| 8 | 500 | L-carvone | 450 | 50 | + | W |
| 9 | 500 | Citral | 15 | 485 | − | W |
| 10 | 500 | Citral | 37.5 | 462.5 | − | W |
| 11 | 500 | Citral | 75 ul | 425 | − | W |
| 12 | 500 | Citral | 112.5 | 387.5 | − | W |
| 13 | 500 | Citral | 150 | 350 | +/−Inverted | W |
| 14 | 500 | Citral | 225 | 275 | +Inverted | W |
| 15 | 500 | Citral | 450 | 50 | +Inverted | W |
| 16 | 500 | T/L | 15 | 485 | − | W |
| 17 | 500 | T/L | 37.5 | 462.5 | − | W |
| 18 | 500 | T/L | 75 | 425 | − | W |
| 19 | 500 | T/L | 112.5 | 387.5 | − | W |
| 20 | 500 | T/L | 150 | 350 | +/− | W |
| 21 | 500 | T/L | 225 | 275 | + | W |
| 22 | 500 | T/L | 450 | 50 | + | W |
| 23 | 500 | Eugenol | 15 | 485 | − | W |
| 24 | 500 | Eugenol | 37.5 | 462.5 | − | W |
| 25 | 500 | Eugenol | 75 | 425 | − | W |
| 26 | 500 | Eugenol | 112.5 | 387.5 | +/− | W |
| 27 | 500 | Eugenol | 150 | 350 | + | W |
| 28 | 500 | Eugenol | 225 | 275 | + | W |
| 29 | 500 | Eugenol | 450 | 50 | + | W |
| 30 | 500 | Geraniol | 15 | 485 | − | W |
| 31 | 500 | Geraniol | 37.5 | 462.5 | − | W |
| 32 | 500 | Geraniol | 75 | 425 | − | W |
| 33 | 500 | Geraniol | 112.5 | 387.5 | − | W |
| 34 | 500 | Geraniol | 150 | 350 | − | W |
| 35 | 500 | Geraniol | 225 | 275 | −Inverted | W |
| 36 | 500 | Geraniol | 450 | 50 | +Inverted | W |
| 37 | 500 | C/L/E | 15 | 485 | − | W |
| 38 | 500 | C/L/E | 37.5 | 462.5 | − | W |
| 39 | 500 | C/L/E | 75 | 425 | − | W |
| 40 | 500 | C/L/E | 112.5 | 387.5 | − | W |
| 41 | 500 | C/L/E | 150 | 350 | − | W |
| 42 | 500 | C/L/E | 225 | 275 | +/− | W |
| 43 | 500 | C/L/E | 450 | 50 | + | W |

Inverted = Phase Inverted – solids floating on top
− no free oil;
W = white;
Y = yellow.

From the results the following observations were made:
All terpenes appeared to load into Baker's YP and SAF Mannan.
SAF Mannan has a higher terpene loading capacity than bakers YP.
The two and three way mixtures of terpenes also appear to efficiently load.
The terpene Eugenol appears to have a higher density than the particles and water as it was found associated with the pellet.
For the SAF Mannan, the higher load levels and lighter particles resulted in loaded particles floating on the surface of the aqueous layer for citral and geraniol.
Citral was protected from oxidation by the SAF Mannan but not by the Baker's YP.

The approximate maximal loading for each particle type was determined and is shown in Tables 9 and 10 below. Percentage loaded represents a ratio of the amount of terpene loaded to the amount of particle present (weight for weight).

TABLE 9

Maximal terpene loading in Baker's YP.

| Terpene | Vol. Loaded µl | % Loaded w/w |
|---|---|---|
| L-carvone | 37.5 | 33.3 |
| Citral | 75 | 67% |
| Thymol/L-carvone 1:1 | 75 | 67% |
| Eugenol | 75 | 67% |
| Geraniol | 75 | 67% |
| Citral/L-carvone/Eugenol (1:1:1) | 75 | 67% |

TABLE 10

Maximal terpene loading in SAF Mannan.

| Terpene | Vol. loaded µl | % Loaded w/w |
|---|---|---|
| L-carvone | 112.5 | 100% |
| Citral | 150 | 133% |
| Thymol/L-carvone 1:1 | 112.5 | 100% |
| Eugenol | 112.5 | 100% |
| Geraniol | 150 | 133% |
| Citral/L-carvone/Eugenol (1:1:1) | 150 | 133% |

EXAMPLE 8

Evaluation of Terpene Stability in Aqueous Emulsions and Encapsulated Terpene Formulations Terpene stability was assessed by the observation of citral formulations for the formation of a yellow colored oxidation product. As noted in the right hand column in Tables 5-8 citral emulsions and citral encapsulated Bakers YP turned a progressively increasing yellow color over time. However, citral encapsulation in SAF Mannan™ increased citral stability as evidenced by a reduction or absence of yellow color over time.

EXAMPLE 9

Loading of Terpenes in Minimal Water

The following protocol was carried out to evaluate the possibility that terpene loading and encapsulation into YP could be carried out at a very high Yeast Particles (YP) solids level to allow for direct extrusion of the loaded formulation into a fluidised bed drier. The minimal amount of water to completely hydrate the SAF Mannan™ particles was determined to be 3.53 g water per g solids. This defines the hydrodynamic volume (HV) or water absorptive capacity of the particles. At this level of water the hydrated particles have a consistency of a stiff dough which is thixotropic, i.e. shear thinning like mayonnaise. Addition of water up to 40% above the HV results in a thick flowable paste. The standard reaction that has been used in the above examples was carried out at 3×HV water.

Figure 7:
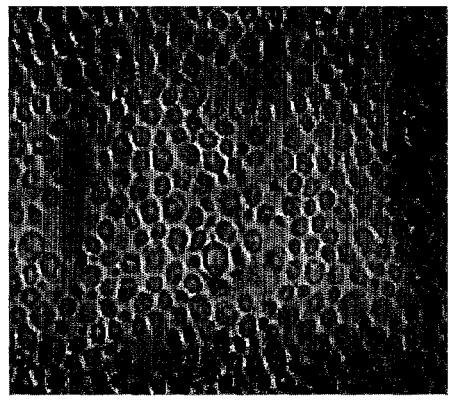
FIG. 7 represents a light micrograph of yeast cell walls encapsulating terpene in HV of water.
Figure 8:
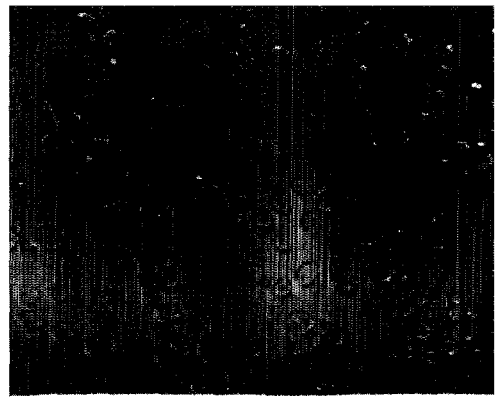
FIG. 8 represents a light micrograph of yeast cell walls encapsulating terpene in HV plus 5% of water.
Figure 9:
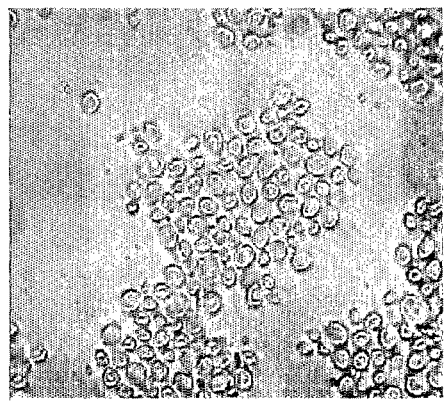
FIG. 9 represents a light micrograph of yeast cell walls encapsulating terpene in HV plus 10% of water.
Figure 10:
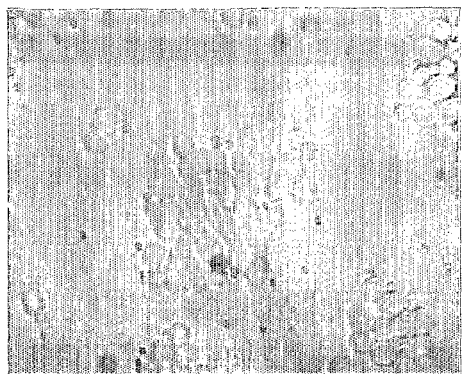
FIG. 10 represents a light micrograph of yeast cell walls encapsulating terpene in HV plus 20% of water.
Figure 11:
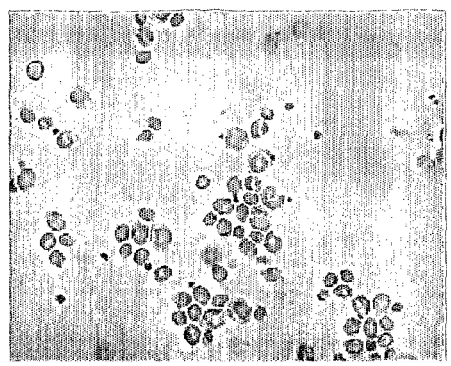
FIG. 11 represents a light micrograph of yeast cell walls encapsulating terpene in HV plus 30% of water.
Figure 12:
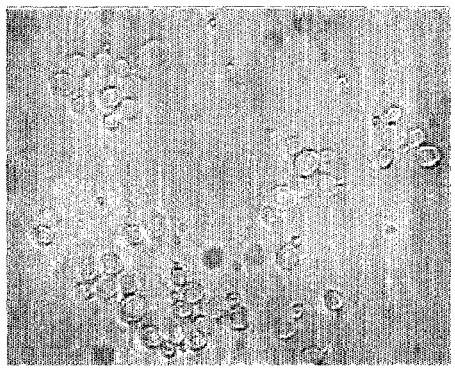
FIG. 12 represents a light micrograph of yeast cell walls encapsulating terpene in HV plus 40% of water.
Figure 13:
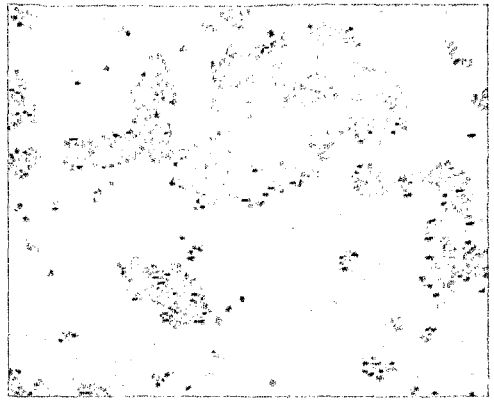
FIG. 13 represents a light micrograph showing the dispersal of dried hollow glucan particles encapsulating a terpene component and no xanthan gum.
Figure 14:
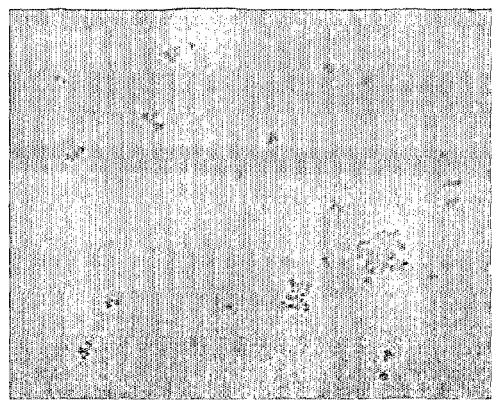
FIG. 14 represents a light micrograph as in FIG. 13 where 0.07 g of 1% xanthan gum is included.
Figure 15:
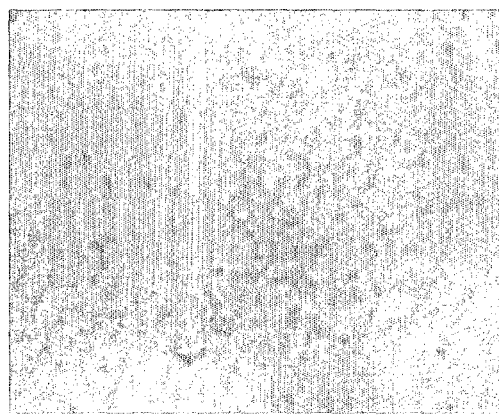
FIG. 15 represents a light micrograph as in FIG. 13 where 0.14 g of 1% xanthan gum is included.
Figure 16:
FIG. 16 represents a light micrograph as in FIG. 13 where 0.28 g of 1% xanthan gum is included.
Figure 17:
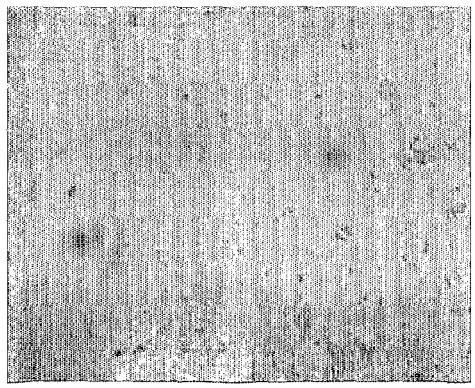
FIG. 17 represents a light micrograph as in FIG. 13 where 0.55 g of 1% xanthan gum is included.
Figure 18:
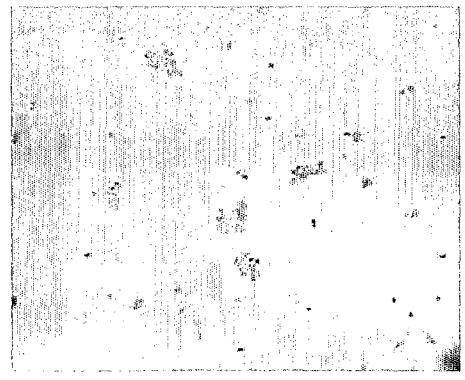
FIG. 18 represents a light micrograph as in FIG. 13 where 1.1 g of 1% xanthan gum is included.
Figure 24:
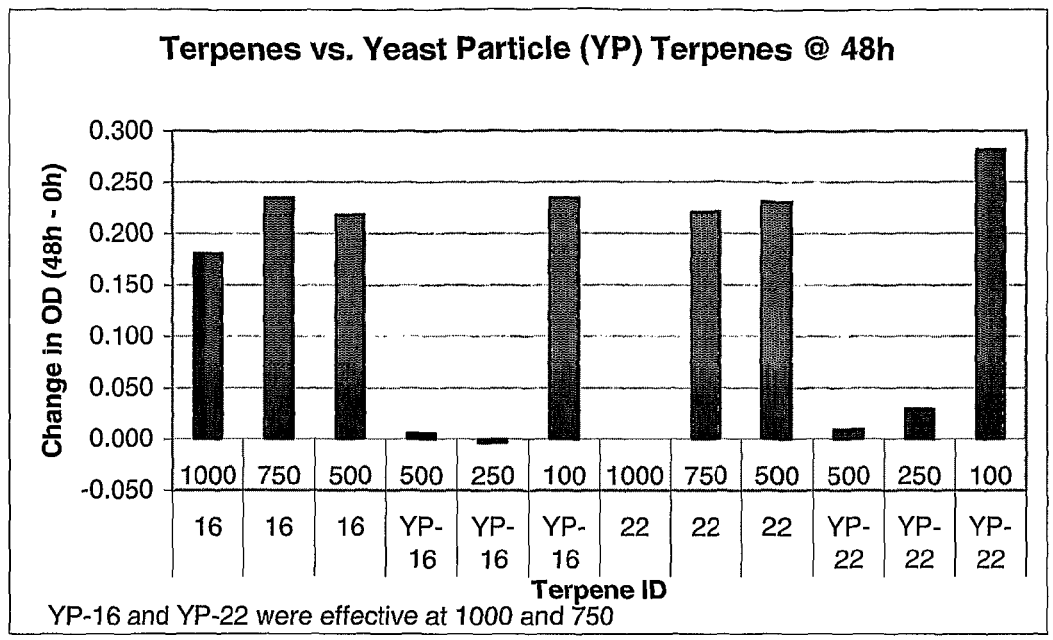
FIG. 24 shows a graph showing a comparison of encapsulated vs. non-encapsulated terpene formulations.

A series of terpene (L-carvone) loading reactions were carried out keeping the ratio of particle:terpene:Tween (1:0.44:0.04) constant and varying the amount of water in the system from the HV (3.53 g) to HV+40% water (4.92 g). Controls were the standard loading system which uses 3×HV water, particles only and terpene only reactions. Following overnight incubation samples of the mixtures were evaluated microscopically for free terpene and evidence of terpene uptake into the particles and for material flow characteristics by assessing flow in inverted tubes over 15 minutes. In addition, the presence of free oil was assessed by hydrating the reaction mixture with 5×HV, vortexing to obtain a complete dispersion of particles and centrifugation to sediment the particle encapsulated terpene. The results are shown in Table 11 and FIGS. 7 to 12. FIGS. 7 to 12 show the loading results of the following tubes:

FIG. 7—Tube 3
FIG. 8—Tube 5
FIG. 9—Tube 6
FIG. 10—Tube 8
FIG. 11—Tube 10
FIG. 12—Tube 11

TABLE 11

| Tube | SAF g | Terpene Emulsion | Weight (g) | Water (g) | Free Terpene | Flow |
|---|---|---|---|---|---|---|
| 1 | — | L-carvone | 4.64 | 4.5 | + | + |
| 2 | 1 | — | — | 8.0 | − | + |
| 3 | 1 | L-carvone | 4.64 | 4.5 | − | + |
| 4 | 1 | L-carvone | 4.64 | — | − | − |
| 5 | 1 | L-carvone | 4.64 | 0.17 | − | − |
| 6 | 1 | L-carvone | 4.64 | 0.35 | − | − |
| 7 | 1 | L-carvone | 4.64 | 0.52 | − | Sl |
| 8 | 1 | L-carvone | 4.64 | 0.7 | − | Mod |
| 9 | 1 | L-carvone | 4.64 | 0.87 | − | High |
| 10 | 1 | L-carvone | 4.64 | 1.05 | − | High |
| 11 | 1 | L-carvone | 4.64 | 1.39 | − | High |

The results shown in Table 11 and FIGS. 7 to 12 demonstrate that terpene loading and encapsulation into the particles occurred at all water ratios evaluated. Surprisingly, equivalent loading occurred even when the loading reaction was taking place in a reaction with the consistency of a stiff dough using the minimal amount of water to hydrate the particles. The absence of free terpene was observed microscopically (FIGS. 7 to 12) and in the low level of terpene in the supernatants, as evidenced by a marked reduction in the turbidity of the supernatant compared to the terpene only control.

These results extend our understanding of the conditions to load terpenes into hollow glucan particles. The flexibility to use a minimal volume of water to hydrate the particles during the loading process will allow loading of the terpenes under conditions where the reaction mixture is a malleable dough-like consistency using standard food-grade swept surface dough mixers. The consistency of the final high solids terpene loaded mixture is suitable for direct extrusion to form noodles and pellets for fluidised bed drying.

Suitable facilities to scale up production in this manner would require:
Gaulin homogeniser, or equivalent to produce stable terpene emulsion.
Swept surface dough mixing tank.
Extruder.
Fluidised bed drier.

EXAMPLE 10

Evaluation of an Interstitial Hydrocolloid Agent to Aid Dispersion in Dried Hollow Glucan Particles Encapsulating a Terpene Component Dispersion when Re-Hydrated The following protocol was adopted to evaluate the effect of an interstitial hydrocolloid to increase dried hollow glucan particle encapsulated terpene formulations to disperse when hydrated.

SAF Mannan™ particles
0.1% Tween 80
L-carvone
Xanthan Gum—1% w/v in 0.1% Tween 80

The effect of increasing xanthan gum levels on dry hollow glucan particle encapsulated L-carvone dispersion in water was assessed by loading L-carvone into SAF Mannan by incubating 1.1 g of an L-carvone emulsion (L-carvone: water:surfactant ratio of 0.75:0.3:0.05) with 1 g SAF Mannan and 4.4 g 0.1% Tween 80 containing 0-1% xanthan gum as shown in Table 12.

TABLE 12

| Tube | SAF g | L-carvone Emulsion (g) | 0.1% Tween-80 (g) | 1% Xanthan (g) | Visual Observations |
|---|---|---|---|---|---|
| 1 | 1 | 1.1 | 4.4 | 0 | Large non-uniform clumps |
| 2 | 1 | 1.1 | 4.33 | 0.07 | Uniform suspension |
| 3 | 1 | 1.1 | 4.26 | 0.14 | Uniform suspension |
| 4 | 1 | 1.1 | 4.12 | 0.28 | Uniform suspension |
| 5 | 1 | 1.1 | 3.85 | 0.55 | Uniform suspension |
| 6 | 1 | 1.1 | 3.3 | 1.1 | Finer Uniform suspension |
| 7 | 1 | 1.1 | 2.2 | 2.2 | Finer Uniform suspension |
| 8 | 1 | 1.1 | 0 | 4.4 | Finer Uniform suspension |

The results in Table 12 and FIGS. 13 to 20 demonstrate that the inclusion of a high molecular weight hydrocolloid during the drying of the particle encapsulated terpene aids in the hydration and dispersion of the microparticles into a uniform suspension. Other examples of such hydrocolloid agents are maltodextrin, alginates, or the like.

It may also be worthwhile to include a pellet coating to increase the stability of the loaded terpenes, and to provide a sustained release of terpene.

EXAMPLE 11

Evaluation of Minimum Inhibitory Concentration (MIC) of Terpene Emulsions, Fresh Baker's YP and SAF Mannan Encapsulated Terpenes and Freeze-Dried Baker's YP and SAF Mannan Encapsulated Terpenes Against *S. aureus*

The results of a protocol performed to compare the MIC of fresh versus freeze dried hollow glucan particle encapsulated terpene formulations are shown below in Table 13. A simple terpene emulsion was also tested and the results are shown for comparison.

TABLE 13

| | MIC µg/ml terpene | | | | |
|---|---|---|---|---|---|
| | | Bakers | | SAF Mannan | |
| Terpene | Emulsion | Fresh | Freeze Dried | Fresh | Freeze Dried |
| L-carvone | 3.75 | 0.1 | >0.04 | 0.01 | >0.02 |
| Citral | 0.94 | 0.01 | 0.05 | 0.01 | >0.03 |
| L-carvone/Thymol | 0.23 | 0.01 | 0.03 | 0.01 | 0.05 |
| Eugenol | 0.12 | 0.03 | 0.05 | 0.01 | 0.05 |
| Geraniol | 0.47 | 0.03 | 0.06 | 0.02 | >0.03 |
| L-carvone/ Citral/Eugenol | 0.23 | 0.03 | 0.06 | 0.02 | 0.05 |

The conclusions taken from the above results were:
1. Terpene loading into hollow glucan particles appears to enhance terpene MIC. Generally the fresh terpene emulsions are ~4-375 fold less potent than the encapsulated formulations
2. Terpenes loaded in SAF Mannan™ perform slightly better than Baker's YP.
3. Freshly loaded terpene compositions perform slightly better than freeze dried compositions (there may be some volatilisation of terpenes from dry compositions during freeze drying).
4. Terpenes in aqueous emulsions are stable for at least 3 weeks.

EXAMPLE 12

Efficacy of Encapsulated Terpenes at Pilot Plant Scale Against S. aureus

Anti-microbial assays were carried out with encapsulated terpenes and mixtures produced at the pilot plant scales against S. aureus. Both the fresh and freeze dried encapsulated terpene samples containing materials demonstrated strong anti-microbial activities. The results are summarised in Table 14 below.

Terpenes were encapsulated in SAF-Mannan™ at a 2.5 Kg scale. A mixture of three terpenes (Geraniol, 275 g; Eugenol, 385 g; and thymol, 440 gram was dissolved and homogenized with 100 g Tween-80 and 8 L of water. SAF-Mannan™ (2.5 Kg) was added to form a homogenous suspension. The suspension was passed through a Gaulin homogenizer to reduce particle size and the homogenate was incubated overnight at room temperature. A sample of the encapsulated terpene was removed and stored at room temperature. The remaining encapsulated terpene was then frozen in trays and freeze dried. The freeze dried encapsulated terpene powder was ground and stored at room temperature.

TABLE 14

| Material | MIC (ppm) |
| --- | --- |
| Staphylococcus aureus assays | |
| YGP empty shell control | >2500 |
| Pilot Plant - Fresh | 100 |
| Pilot Plant - Freeze dried | 100 |

At the pilot plant scale both the fresh and freeze dried samples were equally potent on a w/w terpene basis.

Based on the large scale preparation results, the predicted effective dose of the freeze dried formulation against S. aureus is 200 ppm (the formulation contains ~50% terpene w/w) or 0.2 g/L water.

EXAMPLE 13

Efficacy of Encapsulated Terpenes Against Mycobacterium

Terpene emulsions were prepared as follows:
1. Citral—4.5 g citral in 1.5 ml 3.3% Tween-80.
2. L-carvone/eugenol—2.25 g L-carvone and 2.25 g Eugenol in 1.5 ml 3.3% Tween-80.
3. Eugenol—4.5 g eugenol in 1.5 ml 3.3% Tween-80.
4. Geraniol—4.5 g geraniol in 1.5 ml 3.3% Tween-80.
5. Geraniol/thymol mixture—2.25 g geraniol and 2.25 g thymol in 1.5 ml 3.3% Tween-80.
6. Control emulsion—6 ml 1% Tween-80.

SAF-Mannan™ (2.5 g) was mixed with 3 ml of each emulsion and 7 ml of 1% Tween 80 and incubated overnight to encapsulate the terpenes and terpene mixtures. The encapsulated terpene formulations were frozen and freeze dried and the powders ground to a fine powder. Suspensions of encapsulated terpenes (25 mg/ml) and unencapsulated terpene emulsions were assayed for antibacterial activity against Mycobacterium. The results are set out in Table 15

TABLE 15

| Material | MIC (ppm) |
| --- | --- |
| Mycobacterial assays | |
| YGP Citral FD | 250 |
| YGP L-Carvone/Eugenol FD | 500 |
| YGP Eugenol FD | 500 |
| YGP Geraniol FD | 125 |
| YGP Geraniol/Thymol FD | 62.5 |
| Control Emulsion | >1000 |
| Citral Emulsion | 35 |
| L-carvone/Eugenol Emulsion | 53 |
| Eugenol Emulsion | 105 |
| Gernaniol Emulsion | 70 |
| Geraniol/Thymol Emulsion | 53 |

FD = (Freeze Dried)

EXAMPLE 14

Nematocidal Activity of Encapsulated Terpenes

Preparations of yeast cell walls encapsulating citral were prepared according to the procedures described above. The hollow glucan particles contained 17.5% citral, and the particles were present at in the test preparations at a concentration of 1000 ppm. This means that terpenes were effectively present at a concentration of 175 ppm.

1.0 ml of the test preparations was added to 0.1 to 0.15 ml of water containing root-knot nematodes. 1.0 water was added to the nematodes as the control.

Observations were made as previously described and the kill rate assessed (i.e. percentage dead) after 24 and 48 hrs. The results shown below in Table 16 are an average of 2 sets of results.

TABLE 16

Nematicidal activity of encapsulated terpene solution (17.5% citral @ 1000 ppm)

| | Kill Rate | |
| --- | --- | --- |
| Time | Test | Control |
| 24 h | 45 | 17 |
| 48 h | 56 | 21 |

The results demonstrate that hollow glucan particles encapsulating terpenes are effective at killing root-knot nematodes at a particle concentration of 1000 ppm, which corresponds to a citral concentration of only 175 ppm.

Thus hollow glucan particles encapsulating terpenes appear to be as effective as terpenes in solution or with surfactant as nematicides. The nematicidal activity is retained despite the terpene being encapsulated within the particle. It can be expected that higher concentrations of terpenes within the hollow glucan particles, or higher concentrations of the particles would result in an even higher kill rate, as is the case for terpenes in solution or with surfactant.

EXAMPLE 15

Fugicidal Properties of Encapsulated and Non-Encapsulated Terpenes

The following protocols were carried out to assess the fungicidal properties of various terpene combinations, and to compare the efficacy of encapsulated and non-encapsulated compositions.

Assessment of Anti-Fungal Properties of Different Terpene Formulation

A microtitre plate assay was used to assess the minimum inhibitory concentration (MIC) of a range of terpene compounds against different pathogenic organisms. The assay used for each organism is described in detail later but important general features are as follows.

The assay uses two incubation periods to distinguish between static (growth inhibition) and cidal (killing) activities. The first incubation period allows assessment of growth inhibition, but cannot distinguish between merely prevention of growth and killing of the cells. The purpose of the second incubation period is to allow sufficient time and nutrients for any dormant or inhibited cells that survive terpene exposure to proliferate. Any cells that were inhibited by fungistatic effects should respond and grow during the second incubation period, whereas cells that were killed by exposure to terpenes will not grow in the fresh medium.

Initial screening experiments were carried out using a total of 31 different terpene formulations (Table 17). These experiments were repeated using a subset of strongly active terpene formulations (Table 18).

A combination of the terpenes geraniol, eugenol and thymol in a ratio of 2:1:2 encapsulated within glucan particles was also tested; this sample is referred to as YP-GET. A non-encapsulated geraniol, eugenol and thymol combination in the same ratio was also tested for comparison with the encapsulated form.

MIC Assay Using *Saccharomyces cerevisiae*

*S. cerevisiae* ($5 \times 10^5$ cells/mL in YPD growth medium) were added to each well of a 96-well microtitre plate in 100 µL aliquots. At least one column per plate was designated as a cell-only control and no terpene was added to these wells. Aliquots (100 µL) of different terpene formulations were added to the first row of the remaining columns, and serial 2-fold dilutions were performed by transferring 100 µL from one row to the next a total of 7 times. Finally, 100 µL was discarded from the last row in order to ensure that all wells contained the same volume. Microtitre plates were incubated statically overnight at 30° C.

Following incubation, plates were scored for inhibition of growth (evidenced by a lack of turbidity). Growth inhibition (≥75%) was visually confirmed by microscopy.

Once the MIC had been determined for each formulation, the microtitre plates were centrifuged and the spent medium was removed from non-turbid wells. The cells were resuspended in fresh medium (100 µL) and the plates were re-incubated overnight at 30° C. Assessment of growth inhibition was performed as before.

MIC Assay Using a Mixed Inoculum

The different terpene formulations were serially diluted in the 96-well microtitre plate as described for *S. cerevisiae*. Molten YPD agar was then added to the wells, together with 5 µL mixed inoculum (prepared from mouldy grape leaves to a concentration of $5 \times 10^4$ cells/mL). The plates were incubated statically for 24 hours at room temperature and spore growth was visually assessed by microscopy.

Due to the use of solid medium, the second incubation period in fresh media could not be performed.

MIC Assay Using *Colletotrichum graminicola*

The different terpene formulations were serially diluted in the 96-well microtitre plate as described for *S. cerevisiae*. *C. graminicola* (300 spores/well) were added to the diluted terpenes and the plates were incubated statically for 48 hours at room temperature. Spore germination and growth were visually assessed by microscopy.

Once the MIC had been determined for each formulation, the microtitre plates were centrifuged and the spent medium was removed from growth-inhibited wells. The spores were resuspended in fresh medium (100 µL) and the plates were re-incubated overnight at room temperature. Assessment of growth inhibition was performed as before.

TABLE 17

MIC and fungicidal MIC values obtained from initial screening of 31 terpene formulations

| Terpene formulation[a] | *Saccharomyces cerevisiae* MIC | Cidal MIC | Mixed microbes MIC | Cidal MIC | *Colletotrichum graminicola* MIC | Cidal MIC |
|---|---|---|---|---|---|---|
| 1  Geraniol (G) | 500 | 500 | 250 | NT | 63 | 63 |
| 2  Eugenol (E) | 500 | 500 | 125 | NT | 125 | 125 |
| 3  Thymol (T) | 250 | 250 | 63 | NT | 63 | 500 |
| 4  Citral (C) | 250 | 250 | 63 | NT | 125 | 63 |
| 5  L-carvone (L) | 250 | 500 | 63 | NT | 125 | 125 |
| 6  GE | 1000 | 2000 | 125 | NT | 63 | 250 |
| 7  GT | 500 | 500 | 250 | NT | 125 | 63 |
| 8  GC | 500 | 500 | 125 | NT | 125 | 250 |
| 9  GL | 500 | 500 | 125 | NT | 125 | 125 |
| 10 ET | 500 | 500 | 125 | NT | 125 | 125 |
| 11 EC | 250 | 1000 | 31 | NT | 125 | 125 |
| 12 EL | 500 | 1000 | 125 | NT | 125 | 125 |
| 13 TC | 500 | 500 | 16 | NT | 63 | 63 |
| 14 TL | 500 | 1000 | 63 | NT | 63 | 63 |
| 15 CL | 500 | 500 | ≤8 | NT | 63 | 63 |
| 16 GET | 500 | 500 | 23 | NT | 94 | 94 |
| 17 GEC | 250 | 500 | 94 | NT | 94 | 94 |
| 18 GEL | 500 | 1000 | 188 | NT | 188 | 188 |
| 19 GTC | 500 | 500 | 47 | NT | 188 | 188 |
| 20 GTL | 500 | 1000 | 94 | NT | 94 | 94 |
| 21 GCL | 250 | 500 | 94 | NT | 47 | 47 |
| 22 ETC | 125 | 250 | 188 | NT | 94 | 94 |
| 23 ETL | 500 | 1000 | ≤12 | NT | 94 | 94 |
| 24 ECL | 500 | 1000 | ≤12 | NT | 188 | 188 |
| 25 TCL | 500 | 1000 | 23 | NT | 94 | 375 |
| 26 GETC | 500 | 1000 | 125 | NT | 250 | 500 |
| 27 ETCL | 500 | 1000 | 63 | NT | 125 | 125 |
| 28 GTCL | 500 | 1000 | 125 | NT | 250 | 250 |
| 29 GECL | 500 | 1000 | ≤16 | NT | 500 | 500 |
| 30 GETL | 1000 | 1000 | 125 | NT | 500 | 250 |
| 31 GECTL | 1000 | 1000 | 78 | NT | 625 | 625 |
| GET (2:1:2 ratio, w/w/w) | NT | NT | 98 | NT | 78 | 156 |
| YP-GET (G:E:T ratio of 2:1:2, w/w)[b] | 98 | 391 | 98 | NT | 20 | 20 |

NT, not tested;
YP-GET, yeast-encapsulated GET formulation.
[a]Terpene combinations were mixed in a 1:1 (w/w) ratio unless otherwise indicated.
[b]MICs calculated by terpene content.

TABLE 18

Repeat assay to determine MIC and fungicidal MIC values

| Terpene formulation[a] (by No.) | Saccharomyces cerevisiae | | Mixed microbes isolated from mouldy grape leaves[b] | | Colletotrichum graminicola | |
|---|---|---|---|---|---|---|
| | MIC | Cidal MIC | MIC | Cidal MIC | MIC | Cidal MIC |
| T (3) | NT | NT | 63 | NT | NT | NT |
| L (5) | NT | NT | 250 | NT | NT | NT |
| GE (6) | NT | NT | NT | NT | 125 | 500 |
| EC (11) | 125 | 250 | NT | NT | NT | NT |
| TC (13) | NT | NT | 250 | NT | 63 | 250 |
| TL (14) | NT | NT | 500 | NT | 250 | 500 |
| CL (15) | NT | NT | 500 | NT | 125 | 500 |
| GET (16) | NT | NT | 375 | NT | 188 | 375 |
| GEC (17) | 250 | 500 | NT | NT | NT | NT |
| GCL (21) | 250 | 500 | NT | NT | 375 | 750 |
| ETC (22) | 125 | 250 | NT | NT | 94 | 188 |
| ETL (23) | NT | NT | 375 | NT | 188 | 750 |
| ECL (24) | NT | NT | 750 | NT | NT | NT |
| TCL (25) | NT | NT | 750 | NT | 94 | 375 |
| ETCL (27) | NT | NT | 500 | NT | 63 | 500 |
| GECL (29) | NT | NT | 1000 | NT | NT | NT |
| YP-GET (G:E:T ratio of 2:1:2, w/w)[c] | 98 | 195 | NT | NT | 39 | 156 |

NT, not tested;
YP-GET, yeast-encapsulated GET formulation.
NOTE:
Samples were assayed in duplicate. If different values were obtained between duplicate samples, the higher value has been presented. No duplicate samples differed by more than one 2-fold dilution.
[a]Terpene combinations were mixed in a 1:1 (w/w) ratio unless otherwise indicated.
[b]1 × 10$^4$ cells/mL stock suspension.
[c]MICs calculated by terpene content.

Mixed Inoculum

Using a mixed inoculum presents a number of problems. The variability in spore content between preparations results in poor interassay reproducibility, and growth of contaminating organisms impedes the scoring of spore germination. Unicellular yeast species are particularly problematic in masking spore growth. Although precise data could not be obtained from this assay, an inhibitory effect of terpenes was observed.

Identification of spores was easier during scoring of the repeat assay than during the initial screening assay as a larger number of spores were used (approximately 50/well versus approximately 10/well). Therefore, data obtained during the repeat assay may provide a more reliable estimate of MIC.

*Colletotrichum graminicola*

The generally higher MIC values obtained from the repeat assay compared to the initial screening assay may be due to:
 use of 1-week-old terpene solutions
 use of freshly prepared spores, which had a higher viability than those used in the initial screening assay and may therefore be more difficult to kill.

Comparison of terpene formulations as free emulsions with the same terpene formulations when encapsulated in hollow glucan particles: *Saccharomyces cerevisiae* MIC assays YPD growth medium (100 μL) was added to each well of a 96-well microtitre plate and aliquots of different terpene formulations were added to the first row, giving a total volume of 200 μL in this row. One column was designated as a cell-only control and no terpene was added to these wells. Serial 2-fold dilutions were performed by transferring 100 μL from one row to the next a total of 7 times. Finally, 100 μL was discarded from the last row in order to ensure that all wells contained the same volume. *S. cerevisiae* (5×10$^5$ cells/mL in YPD growth medium) were then added to each well in 100 μL aliquots, and the absorbance at 620 nm ($A_{620}$) was measured for each well using a microtitre plate reader. Microtitre plates were incubated statically overnight at 30° C.

Following incubation, the $A_{620}$ was measured again and plates were scored for inhibition of growth (≥75%). Growth inhibition was visually confirmed by microscopy.

For the free terpene emulsions, once the MIC had been determined for each formulation, the microtitre plates were centrifuged and the spent medium was removed from the growth-inhibited wells. The cells were resuspended in fresh medium (100 μL) and the plates were re-incubated overnight at 30° C. Assessment of growth inhibition was performed as before.

MIC and fungicidal MIC results are summarised in Table 19.

Results

TABLE 19

MIC and fungicidal MIC values obtained from screening of 31 terpene formulations against *Saccharomyces cerevisiae*

| Terpene formulation[a] (Reference No) | Yeast-encapsulated formulations[b,c] | | Free terpene emulsions | |
|---|---|---|---|---|
| | MIC | Cidal MIC | MIC | Cidal MIC |
| G (1) | 111 | NT | 250 | 250 |
| E (2) | 131 | NT | 125 | 250 |
| T (3) | 115 | NT | 125 | 250 |
| C (4) | 118 | NT | 125 | 250 |
| L (5) | 254 | NT | 250 | 500 |
| GE (6) | 118 | NT | 250 | 500 |
| GT (7) | 108 | NT | 125 | 250 |
| GC (8) | 113 | NT | 125 | 250 |
| GL (9) | 117 | NT | 250 | 500 |
| ET (10) | 131 | NT | 125 | 250 |
| EC (11) | 126 | NT | 125 | 250 |
| EL (12) | 129 | NT | 125 | 250 |
| TC (13) | 59 | NT | 63 | 63 |
| TL (14) | 124 | NT | 63 | 125 |
| CL (15) | 124 | NT | 125 | 125 |
| GET (16) | 119 | NT | 63 | 125 |
| GEC (17) | 119 | NT | 125 | 250 |
| GEL (18) | 121 | NT | 125 | 125 |
| GTC (19) | 115 | NT | 125 | 125 |
| GTL (20) | 119 | NT | 125 | 125 |
| GCL (21) | 234 | NT | 125 | 125 |
| ETC (22) | 124 | NT | 125 | 125 |
| ETL (23) | 123 | NT | 125 | 125 |
| ECL (24) | 63 | NT | 63 | 125 |
| TCL (25) | 61 | NT | 125 | 500 |
| GETC (26) | 61 | NT | 63 | 250 |
| ETCL (27) | 120 | NT | 63 | 125 |
| GTCL (28) | 124 | NT | 125 | 125 |
| GECL (29) | 125 | NT | 125 | 125 |
| GETL (30) | 122 | NT | 125 | 250 |
| GECTL (31) | 120 | NT | 125 | 250 |
| GET (2:1:2 ratio, w/w/w) | 125[d] | NT | 125 | 250 |
| YP-GET (G:E:T ratio of 2:1:2, w/w) | 125 | NT | 125[c] | 250[c] |
| YP-ETC (E:T:C ratio of 1:1:1, w/w) | 125 | NT | 125[c] | 250[c] |

NT, not tested;
YP-GET, yeast-encapsulated GET formulation;
YP-ETC, yeast-encapsulated ETC formulation.
[a]Terpene combinations were mixed in a 1:1 (w/w) ratio unless otherwise indicated.
[b]Yeast-encapsulated formulations unless otherwise indicated.
[c]MIC calculated by terpene content.
[d]Non-encapsulated emulsion formulation.

For both the terpene emulsions and yeast-encapsulated terpenes, MICs were typically ≤125 ppm, with the most active formulations inhibiting growth at ~60 ppm. MIC values obtained for the terpene emulsions were similar to those obtained for their respective yeast-encapsulated formulations. When different values were obtained, they only differed by approximately one 2-fold dilution.

Many of the free terpene emulsions were fungicidal at the growth inhibitory MIC, with the majority showing fungicidal activity at a 2-fold higher concentration.

These results demonstrate that terpenes encapsulated in glucan particles are at least as effective at killing fungus as non-encapsulated forms. Additionally the encapsulated compositions used may have had reduced potency due to having been stored for 45 days at 4° C. and having a sub-optimal terpene content of ~4% w/w.

The assay to determine fungicidal activity involves a centrifugation step, which attempts to separate the microbial cells from any residual terpene in the growth medium by producing a pellet of cells at the bottom of the well. This pellet is then resuspended in fresh media and incubated for a second time in the absence of terpene. However, the centrifugation step cannot discriminate between microbial cells and yeast particles, therefore when yeast-encapsulated terpenes are used, the cell pellet will also contain terpene-loaded yeast particles. As a result, both the yeast particles and the microbial cells are then resuspended in the fresh medium.

This methodology issue is not considered to affect the results obtained in the experiments described above for the following reasons.

1. In previous experiments, terpene emulsions have been used instead of terpene-loaded yeast particles and fungicidal activity has been clearly shown.
2. Encapsulated terpenes are released by diffusion, and an equilibrium between the concentration of encapsulated terpenes and the concentration of released terpenes in the surrounding medium is quickly reached. Thus, following centrifugation and resuspension in fresh medium, the concentration of released terpene in the growth medium is likely to be well below that required for growth inhibitory activity.
3. There was no growth when the contents of the fungicidal MIC well were plated onto solid agar growth medium. When plated onto solid growth medium, diffusion of any residual terpene throughout the large volume of the agar plate results in a local terpene concentration that is too low to cause growth inhibition. The lack of growth from the contents of the fungicidal MIC well must therefore be due to initial fungicidal activity. In contrast, when an MIC was obtained that was lower than the fungicidal MIC and the contents of the MIC well were plated onto solid agar growth medium, growth was observed, indicating a fungistatic effect.

EXAMPLE 16

Preparation of Encapsulated Terpene Compositions for Field Trials

The purpose of the following protocol was to encapsulate a terpene composition into hollow glucan particles for subsequent field trials.

Materials:
Thymol (supplied by Alpha-Gamma Corporation)
Eugenol (supplied by Alpha-Gamma Corporation)
Geraniol (supplied by Alpha-Gamma Corporation)
1% Tween-80 (supplied by Alpha-Gamma Corporation)
Yeast Cell Wall Particles
Xanthan gum.

The yeast cell wall particles were obtained from Biorigin (Sao Paolo, Brazil) under the trade name Nutricell MOS 55, and were manufactured by Açucareira Quatá S.A, Usina Quatá, Quatá—Sao Paolo—Brazil—Zip Code 19780 000. The particles are a spray dried cell wall extract of *S. cerevisiae* and are a free flowing powder of light beige to tan colour.

Protocol: The following protocol was suitable for a 1 Kg of particles, but can simply be scaled up for larger production.

1. Prepare terpene mixture—mix 375 grams of Geraniol+525 grams Eugenol+600 grams of Thymol and stir in a glass flask.
2. Prepare 6.2 L of 1% Tween 80 by mixing 62 grams Tween 80 in 6.2 L water in 2 gallon white bucket. Mix to form solution.
3. Add 6.2 grams Xanthan Gum to Tween solution and stir to dissolve.
4. Prepare terpene emulsion by mixing 1.5 Kg terpene mixture+6.2 L 1% Tween 80/0.1% Xanthan gum in white bucket using polytron mixer.
5. Add 1,000 grams of yeast cell wall particles—mix using paint mixer to form uniform suspension.
6. Add the terpene emulsion of step 4 to the yeast cell wall particles while mixing to form a thin mayonnaise-like consistency.
7. Pour terpene mixture into cans and incubate overnight.

Results: Encapsulated geraniol, eugenol and thymol in hollow glucan particles was obtained as a paste. The paste was easily converted to a dry powder by conventional spray drying techniques. The paste is the "liquid" composition referred to in the following protocols, and the "powder" is the spray dried form.

EXAMPLE 17

Field Trials of Encapsulated Terpene Composition on Downy Mildew

In grapes, downy mildew is caused by the fungus *Plasmopara viticola*, which infects vineyards worldwide and can cause devastating losses for grape-growers in terms of crop yield and wine quality. The fungus attacks the fruits and all green parts of the vine, causing the leaves to wither and the flowers and berries to rot. The disease manifests as irregular pale yellow or yellow-green spots on the upper surface of leaves, with dense, white-grey, cotton-like fungal growth covering the underside of the leaf lesions. Berries may also be covered with the downy growth and, depending on the time of infection, may turn brown and soft or may not soften at all. Downy mildew is spread through the dispersal of spores by the wind and rain, and requires wet conditions for infection. It is particularly problematic in environments with high humidity. Preventative measures are recommended for management of the disease, with early applications of fungicides followed by repeat applications at appropriate intervals. Resistance has arisen to some treatments, and although the development of resistance can be minimised by rotating the use of different fungicides, it remains a problem.

The purpose of this trial was to investigate the efficacy of the encapsulated terpene formulation of Example 16 (YGP-GET) supplied as a liquid or powder (spray dried) formulation, for the prevention of downy mildew in grapes.

Four adjacent blocks, each covering 0.1 ha, were identified on site 20 in the Kir-Yianni vineyard.

Kir-Yianni is a 35 ha vineyard at an elevation of 300 m. It is bordered by a mixed oak forest on the north and west, and overlooks orchards and vineyards to the south and east.

All four blocks had been treated with multiple products prior to application of the terpene formulation. On 26 Jun. 2004, two of the four blocks were sprayed with the terpene powder formulation at a dose of either 0.5 g/L or 2 g/L (see schematic illustration in FIG. 21). A third block was treated with conventional Bordeaux mix plus wettable sulphur, and the remaining block was left untreated. The vines in each block were monitored for signs of downy mildew over the following week.

Four further adjacent blocks, each covering 0.1 ha, were identified on site 18 in the Kir-Yianni vineyard. All four blocks had been treated with multiple products prior to application of the terpene formulation. On 26 Jun. 2004, two of the four blocks were sprayed with the terpene liquid formulation at a dose of either 1 g/L or 4 g/L (FIG. 21) (note: 1 g of the terpene liquid formulation has a volume of 1 ml). Of the remaining two blocks, one was left untreated and one was sprayed with Mikal®, a conventional treatment for downy mildew, on 28 Jun. 2004. The vines in each block were monitored for signs of downy mildew over the following week.

For both sites, the terpene product was applied at a rate of 1200 L/ha.

The following growth stages of the grapes were recorded:
bud break, 26 Mar. 2004
bloom, 1 Jun. 2004
veraison, 6 Aug. 2004

The study applications took place pre-veraison.

The 2004 growing season was exceptionally late and was wet throughout. Disease pressure from downy mildew was extremely high, *botrytis* levels were elevated, and powdery mildew pressure was moderate.

Both the powder and liquid YGP-GET formulations were stored at room temperature. No special storage conditions were used.

Details of Comparator Products

Powder formulation trial: Bordeaux mix, manufactured by Manica Spa, Italy, packed in Greece by Moscholios Chemicals SA; wettable sulphur.

Liquid formulation trial: Mikal® (fosetyl-al 50%, folpet 25%), manufactured by Bayer CropScience, distributed in Greece by Bayer Hellas SA.

The comparator products were applied as follows:

One application before bud-break at a dosage of 15 g/L followed by two more applications per year at a dosage of 6.5 g/L. A spraying rate of 1000 L/ha was used for all three applications.

Powder formulation trial: Bordeaux mix (2 g/L) and wettable sulphur (2.2 g/L) were applied on 26 Jun. 2004.

Liquid formulation trial: Mikal (3.2 g/L) was applied on 28 Jun. 2004.

Vines were visually examined for symptoms of downy mildew. Onset of the disease was marked by an average of two oily spots per leaf. Treatments that prevented the appearance of further spots were considered to provide effective protection against downy mildew.

Results

YGP-GET Powder Formulation (Spray Dried)

The conventional treatment of Bordeaux mixture provided good protection against downy mildew. Mild symptoms of downy mildew were observed in the control vines. The 0.5 g/L terpene product concentration did not provide protection, and the 2 g/L terpene product concentration provided only slightly better protection than the control. Note: the disease pressure at this site was very low because of the recent pesticide treatment.

Difficulties were encountered in dissolving the powder formulation as it was very fine, resulting in dispersion in the air. This may have adversely affected the efficacy of the product.

YGP-GET Liquid Formulation

When administered at a dose of 4 g/L, the terpene product provided excellent protection against downy mildew on exposed canopy. No protection was provided by the 1 g/L dosage. Serious symptoms of downy mildew were observed in the control block.

The liquid formulation was easy to use and had a pleasant odour.

Discussion

Downy mildew can cause devastating losses for grape-growers because of its effects on crop yield and wine quality. Management of the disease focuses on prevention because, once established, the infection can quickly spread. At the site sprayed with the powder formulation, YGP-GET did not exhibit efficacy at the lower dosage (0.5 g/L), and the dose of 2 g/L was less effective than the conventional treatment. At this site, the recent pesticide applications resulted in low disease pressure, which may have limited the apparent efficacy of the terpene treatment. However, it was considered that a dosage of less than 2 g/L of the terpene product was inadequate.

At the site sprayed with the liquid formulation, excellent protection of exposed canopy was provided by the higher dose level of 4 g/L. Excessive vegetative growth at this site resulted in more effective treatment of the outer, younger branches compared with the older growth in the inner canopy. Complete foliar coverage by the terpene product is useful, as the treatment is not systemic. It is estimated that an approximately 30% increase over the volume used for conventional systemic treatments would achieve good coverage using the terpene treatment.

Conclusions:

Foliar application of YGP-GET liquid formulation was highly effective at controlling downy mildew at a concentration of 4 g/L. The lower concentrations of 0.5 g/L powder and 1 g/L liquid were not effective.

EXAMPLE 18

Field Trials of Encapsulated Terpene Composition on Powdery Mildew

Powdery mildew of grapes is caused by the fungus *Uncinula necator*, and causes reductions in vine growth, fruit quality and winter hardiness of vines. In wine grapes, an infection level of only 3% of berries can affect wine quality. The disease is characterised by small white-grey patches of fungal growth that enlarge into a powdery, white coating on the leaves. The fungal growth can also occur on the berries, which may split. In contrast to downy mildew, which requires warm wet conditions, powdery mildew can be a problem in drier growing seasons, as it favours shaded areas with humid but not rainy weather conditions. Preventative measures are recommended for management of powdery mildew, with early applications of fungicides followed by repeat applications at appropriate intervals.

This study aimed to investigate the efficacy of application of the YGP-GET composition for the prevention of powdery mildew in grapes.

Three adjacent blocks, each covering 0.1 ha, were identified on site 18 in the Kir-Yianni vineyard. On 19 Jul. 2004, one of the three blocks was sprayed with the YGP-GET liquid formulation at a dose of 2 ml/L and one was left untreated. The remaining block was sprayed with the conventional treatment of Equesion (2.5 g/L), Alliete (0.9 g/L) and Punch (0.075 mL/L) (see FIG. 22). The vines in each block were monitored for signs of powdery mildew over the following week.

Three further adjacent blocks, each covering 0.1 ha, were identified on site 20 in the Kir-Yianni vineyard. On 20 Jul. 2004, one of the three blocks was sprayed with the YGP-GET liquid formulation at a dose of 2 mL/L and the two remaining blocks were left untreated (see FIG. 22). The vines in each block were monitored for signs of powdery mildew over the following week.

At both sites, the blocks had previously been treated with multiple products, including a prior application of terpene product.

All terpene treatments were applied at a rate of 1200 L/ha to ensure complete coverage.

The following growth stages of the grapes were recorded
bud break, 26 Mar. 2004
bloom, 1 Jun. 2004
veraison, 6 Aug. 2004

The study applications took place pre-veraison.

The 2004 growing season was exceptionally late and was wet throughout. Disease pressure from downy mildew was extremely high, *botrytis* levels were elevated, and powdery mildew pressure was moderate.

Details of Comparator Products

No comparator product was used at site 20. The comparator treatment used at site 18 is detailed below.
Punch® (flusilazole 40%), DuPont.

On 19 Jul. 2004, Punch was applied at a dose of 0.075 ml/L as a preventative treatment for powdery mildew according to the manufacturer's instructions.

Details of Additional Products

No additional products were used at site 20. The additional products used at site 18 are detailed below.
Equesion system (famoxadone 22.5% plus cymoxanil 30%)
Alliete (fosetyl-al 80%)

On 19 Jul. 2004, Equesion (2.5 g/L) and Alliete (0.9 g/L) were applied as preventative treatments for downy mildew. The dose was determined according to the manufacturer's instructions.

The comparator and additional products represent conventional treatments in the integrated pest management schedule.

Vines were visually examined for symptoms of powdery mildew.

Results:
Site 18

Approximately 20% of the peduncles and stems in the control block were black, indicating moderate infection from powdery mildew. In both the conventional treatment block and the terpene-treated block, all stems and bunches were green, indicating that adequate protection had been provided.

Site 20

No evidence of powdery mildew infection was observed in any of the blocks.

Additional Observations

At the end of the growing season, the blocks at sites 18 and 20 generally showed less stress due to disease than the rest of the vineyard.

Powdery mildew infections cause considerable losses to growers through reductions in vine growth, fruit quality and winter hardiness of vines. Furthermore, wine quality can be affected by an infection level of as little as 3% of berries. Management of the disease focuses on prevention because, once established, the infection can quickly spread. In this study, the application of terpene product YGP-GET at site 18 effectively prevented powdery mildew infection, and the level of control exhibited by the terpene product was comparable to that provided by the conventional treatment. The results from site 20 are inconclusive, however, due to the lack of powdery mildew infection. This lack of infection is likely to be due to the extensive application of pesticides prior to the study, which resulted in low disease pressure.

The lower level of stress due to disease at sites 18 and 20 suggests that the earlier terpene treatment applied at these sites may have been beneficial in control of infection in the long term.

Conclusions

YGP-GET effectively prevented powdery mildew infection, with a comparable level of control to that provided by the conventional treatment.

EXAMPLE 18

Further Field Trials of Encapsulated Terpene Composition on Powdery Mildew

The study aimed to further investigate the efficacy of YGP-GET for the treatment of powdery mildew in Grimson Seedless table grapes. A 0.1 ha plot on the Tsigaras vineyard (approximately 80 km south of the Kir-Yianni vineyard) was inadvertently left untreated during an application of Cisteine on 1 Jul. 2004. The vines in this plot subsequently showed severe symptoms of powdery mildew on the leaves, stems and grapes. On 12 Jul. 2004, the untreated plot was sprayed with 3 ml/L liquid YGP-GET formulation at a rate of 1200 l/ha, and the rest of the vineyard was sprayed with the comparator product Rogana. The vines were assessed for symptoms of powdery mildew after 24 hours.

Vines were trained in a high lyre trellis system.

Details of Comparator Product

Rogana (fenbuconazol 5%, binocap 16%), manufactured by BASF (BASF Agro Hellas S.A., Athens, Greece)

On 12 Jul. 2004, Rogana was applied to the Tsigaras vineyard as a treatment for powdery mildew. The dose was determined according to the manufacturer's instructions.

Vines were visually examined for symptoms of powdery mildew.

Results

Severe symptoms of powdery mildew were evident prior to application of YGP-GET. Only 24 hours after YGP-GET application, the white bloom of the powdery mildew turned black, indicating effective antifungal activity. As the disease was effectively halted at this time, no further treatments were applied. YGP-GET showed comparable efficacy to the conventional treatment.

Discussion:

In this study, an established powdery mildew infection was treated quickly and effectively using YGP-GET. Only 24 hours after application, the previously severe powdery mildew infection was halted by application of the terpene product, with comparable efficacy to the conventional treatment.

The preliminary data obtained from this study suggest that YGP-GET may be efficacious in treating established fungal infections in addition to showing preventative ability.

EXAMPLE 19

Further Field Trials of Encapsulated Terpene Composition on Powdery Mildew

Background and Rationale

In the current trial, the use of YGP-GET was investigated as part of a Tasmanian vineyard's (Frogmore Creek Vineyard, Hathaway Trading Pty Ltd, Box 187, Richmond TAS 7025, Australia) experimental programme to control powdery mildew using organic products. The aim of this study was to investigate the short-term efficacy of the application of YGP-GET in the organic control of powdery mildew in Chardonnay grapevines.

In this trial grapevines (Chardonnay variety) were either treated with the terpene product YGP-GET or left untreated (control) on 7 Feb. 2005. Although suppressed by previous organic treatments, the pre-trial severity of powdery mildew was at a level considered unacceptable commercially and was equivalent in the 6 active-treatment plots and 6 control plots. The crop stage was approximately E-L 33-34 (pre-veraison).

YGP-GET (4 mL/L) (liquid formulation) was sprayed onto 6 Chardonnay plots, which had been treated previously with milk. Six Chardonnay plots served as untreated controls, but they had been treated previously with oil/whey. The number of vines per plot was typically 7.

Details of the composition of the YGP-GET used in this protocol are given in Table 20.

TABLE 20

Formulation of Batch Used in Present Study

| Raw material mix details | Weight in lbs | % by Weight |
|---|---|---|
| Geraniol | 323.52 | 6.88 |
| Eugenol | 161.76 | 3.44 |
| Thymol | 323.52 | 6.88 |
| Yeast particles | 722.13 | 15.35 |
| Xanthan | 3.17 | 0.07 |
| Polysorbate | 3.17 | 0.07 |
| Water | 3166.62 | 67.32 |
| TOTAL | 4703.89 | 100.00 |

The severity of powdery mildew was assessed 3 days before terpene treatment and again 3 days post-treatment. In each plot, 20 grape bunches were selected at random (10 bunches per panel side), and disease severity was estimated as the percentage area of the bunches covered with active mildew colonies. No further assessment was possible because the grower subsequently sprayed the entire trial area with sulphur and a vegetable oil-based spraying adjuvant (Synertrol Horti Oil).

Number/Area of Plants to be Treated

Test product: YGP-GET (4 mL/L) to be applied to 6 Chardonnay plots (total of approximately 42 vines), which had been treated previously with milk.

Control: No treatment was applied to 6 Chardonnay plots (total of approximately 42 vines) to be used as controls, but they had been treated previously with oil/whey.

Cultivation Methods

Vitis vinifera (Chardonnay) vines in Block B2: vertical shoot positioning with arched canes.

Cultivation Arrangement

Spacing: Distance of 2.5 m between rows and 1.25 m between vines (within row), with 3,200 vines per hectare. Row orientation was north to south.

Canopy Density

The point-quadrat method was used to characterise the pre-trial canopy density of the Chardonnay vines (Table 21). Measurements were taken on 13 Jan. 2005 by selecting representative sections of the canopy within the Chardonnay plots that previously had been either treated with sulphur or left untreated. Ten measurements were taken in each of the 6 plots of each prior treatment (i.e. a total of 60 measurements for the sulphur-treated plots and 60 measurements for the untreated control plots). In addition, the length and number of nodes on 3 upright shoots (per plot) were measured.

TABLE 21

Pre-trial canopy density of the Chardonnay vines

| Prior Treatment | Gaps (%) | Leaf layer number (LLN) | Interior leaves (%) | Interior clusters (%) | Mean number of nodes | Mean shoot length (cm) |
|---|---|---|---|---|---|---|
| Untreated | 12 | 1.5 | 22 | 26 | 21 | 110 |
| Sulphur | 5 | 2.0 | 27 | 40 | 21 | 104 |
| Optimum Values | 20-40% | ≤1.0-1.5 | <10% | <40% | NA | NA |

NA, not applicable.

General Condition

Previous treatment of these plots with experimental materials suppressed powdery mildew in comparison to the untreated control. However, the level of powdery mildew was considered commercially unacceptable, although equivalent in both the milk- and oil/whey-treated plots.

Application Method, Dose and Regimen

YGP-GET treatment (4 mL/L) was applied on 7 Feb. 2005 with a hand gun connected to a hose reel and pump mounted on the flat tray of a utility vehicle. The spray was propelled with a pump pressure of 1500-1600 kPa (200-230 psi), delivering approximately 63 mL/second. The standard spray volume for conventional treatments (approximately 900 L/ha) was used.

The severity of powdery mildew, estimated as the area (%) of the grape bunches covered with active mildew colonies, was assessed for 20 bunches selected at random within each plot (10 bunches per panel side). Disease severity was assessed on 4 Feb. 2005, 3 days before application of the YGP-GET treatment, and again on 10 Feb. 2005, 3 days after terpene application.

Data were transformed using arcsin transformation to obtain mean separations.

Results

Prior to treatment, the mean severity of powdery mildew on Chardonnay grape bunches in the 6 plots to be treated with terpene (20.4%) was similar to that in the 6 control plots (23.2%; Table 22). Statistical analysis based on arcsin transformation of these data found that there was no significant difference in disease severity before treatment (Table 23). Three days after treatment, however, the mean severity of powdery mildew was 23.8% on the YGP-GET-treated bunches versus 37.8% on the controls (Table 22). Arcsin transformation of these data showed a statistically significant difference in favour of the terpene-treated grape bunches, which had a smaller area covered with active mildew colonies (p=0.058; Table 23).

TABLE 22

Mean severity of powdery mildew (%) on Chardonnay bunches before and after treatment with YGP-GET

| Treatment applied on | Mean severity | |
|---|---|---|
| 7 Feb. 2005 | On 4 Feb. 2005 | On 10 Feb. 2005 |
| YGP-GET | 20.4 | 23.8 |
| None | 23.2 | 37.8 |

TABLE 23

Statistical separation of treatments following arcsin transformation of data

| Treatment applied on | Mean severity (SEM) | |
|---|---|---|
| 7 Feb. 2005 | On 4 Feb. 2005 | On 10 Feb. 2005 |
| YGP-GET | 0.2063 (0.03857) | 0.2411 (0.04303) |
| None | 0.2401 (0.08534) | 0.3954 (0.07852) |
| | t = 0.36 | t = 1.72 |
| | df = 10 | df = 10 |
| | p = 0.726 | p = 0.058 |
| | Two-sided test: difference not significant | One-sided test: untreated > treated |

Discussion:

Infection of grapevines with powdery mildew can cause considerable losses to growers through detrimental effects on vine growth and hardiness, as well as on the quality of the fruit and wine. In organically managed vineyards, growers are searching for alternatives to treatments such as elemental sulphur.

This study investigated the efficacy of encapsulated terpene formulations (4 mL/L) as a liquid formulation in controlling powdery mildew in an organic vineyard in Tasmania, Australia. While other experimental treatments had been used as little as 3 weeks before terpene application, the level of powdery mildew infection was still considered commercially unacceptable. Three days after treatment of Chardonnay vines with YGP-GET, the severity of powdery mildew on treated grapes was significantly less than that on untreated controls. While the severity of infection in untreated controls worsened during the 6 days between pre- and post-treatment assessments, it remained steady in treated vines. Therefore, YGP-GET appeared to have slowed the rate of disease increase on grape bunches that had well-established colonies of sporulating powdery mildew before treatment. Presumably, colony expansion was inhibited, although existing colonies continued to sporulate to some degree. More long-term assessment of efficacy was not possible because the grower subsequently sprayed the entire trial area with sulphur.

These encouraging results demonstrate the efficacy of YGP-GET in controlling powdery mildew in grapevines.

EXAMPLE 20

Field Trials of Encapsulated Terpene Composition on *Botrytis*

*Botrytis* bunch rot of grapes is caused by *Botrytis cinerea*, a common fungus that can cause serious losses in fruit yield. Berries are the predominant site of infection, although the disease can also affect blossom and leaves. Initially, infected berries appear soft and watery, and may become covered with grey fungal growth in conditions of high humidity and moisture. Over time, infected berries shrivel and drop. *Botrytis* favours humid conditions with poor air circulation, and split or damaged berries are particularly susceptible to the spread of infection. Management strategies for *botrytis* include promotion of good air circulation, prevention of wounding and application of fungicides at appropriate times during the growing season.

The aim of this study was to investigate the efficacy of YGP-GET in the treatment of *botrytis* infection in grapes.

The emergence of *botrytis* in the Kir-Yianni vineyard in mid October 2004 (3 weeks after an application of Teldor® could not be treated with conventional agrochemicals because the associated re-entry time restrictions would prevent the planned harvest. Two adjacent 0.1 ha plots were therefore identified on site 7 of the vineyard, and, on 12 Oct. 2004, one of these plots was treated with 4 mL/L YGP-GET liquid formulation and the other was left untreated (see FIG. 23). The crop was harvested 3 days later, and the proportion of infected berries was determined for each plot (percentage weight of total yield). Uninfected berries from both the treated and untreated plots were then mixed in the fermentation tank.

Site 7 had been treated with multiple products prior to the application of the terpene formulation but still showed *botrytis* infection.

Vines were given a single application of 4 ml/L YGP-GET liquid formulation at a rate of 1200 l/ha.

The following growth stages of the grapes were recorded:
bud break, 26 Mar. 2004
bloom, 1 Jun. 2004
veraison, 6 Aug. 2004
harvest, 15 Oct. 2004

The study applications took place 3 days before harvest.

The 2004 growing season was exceptionally late and was wet throughout. Disease pressure from downy mildew was extremely high, powdery mildew pressure was moderate and *botrytis* levels were elevated.

YGP-GET was applied at this time to assess its potential efficacy against a *botrytis* infection that could not otherwise have been treated because of pesticide time restrictions prior to harvest.

Visual assessment of the site prior to terpene product application revealed evidence of *botrytis* infection. After harvest, the berries were displayed on a conveyor belt and infected berries were manually separated from uninfected berries prior to crushing. The proportion of infected berries was calculated as a percentage of the total yield (by weight) for each plot.

Results

Visual assessment of the site prior to YGP-GET application revealed evidence of *botrytis* infection. Following harvest (3 days after YGP-GET application), the proportions of infected berries were 13% and 23% in the treated and untreated plots, respectively. The tested areas were not sufficient to assess statistical significance; however, YGP-GET treatment clearly slowed the progression of the disease.

Fermentation was not affected by the mixing of uninfected berries from the untreated and terpene-treated plots.

Discussion

Conventional treatments for *botrytis* must be halted 3 weeks before harvest, leaving time for considerable damage to crop yield and quality to occur. The development of a treatment that could be used until harvest, or that could be continued closer to harvest than the existing products, could result in significant improvements in crop yield and wine quality, and would be of considerable benefit to growers. In this study, treatment with the terpene product YGP-GET visibly slowed progression of an established *botrytis* infection only 3 days prior to harvest, resulting in a lower proportion of infected berries in the terpene-treated plot than in the untreated plot. Furthermore, despite the use of YGP-GET close to harvest, fermentation was unaffected by the combination of treated and untreated grapes.

These results suggest that YGP-GET is efficacious in reducing the impact of established *botrytis* infections and can be used near to harvest without detrimental effects on subsequent fermentation.

EXAMPLE 21

Evaluation of Encapsulated Terpenes for the Treatment of Established Downy Mildew and Subsequent Evaluation of Grape Quality A trial of YGP-GET was carried out on 25 Aug. 2004 applying the composition at a rate of 1000 g per 250 liters.

A vineyard of Cabernet Sauvignon which was 100% infected and suffering substantial leaf loss due to Downy Mildew was sprayed. Any remaining leaves were infected with spots of Downy Mildew as evidenced by the yellow spot on top of the leaf and the fuzzy growth on the leaf bottom; the classical indication of Downy Mildew. Many of the leaves were almost entirely yellow indicating substantial infection. This leaf loss and the infection in general delays the maturity of the grapes and in many cases the grapes never fully ripen for winemaking purposes.

Observation of totally unripened (i.e. hard dark green berries ~1 cm diameter and oval in shape) bunches occasionally in the vines indicated that the vines were likely infected before veraison, and likely at bloom or before. No early copper (Bordeaux or basic Copper sulfate) application has been used. This vineyard was heavily infected in the previous harvest to the point that no crop was produced from the Cabernet Sauvignon. Leaf loss last year was 100% despite Potassium Bi-carbonate treatment in an attempt to contact kill the Downy Mildew, followed by Stilbourin application for longer term systemic protection.

On 19 Sep. 2004 the grapes treated in this trial were picked and crushed and the following observations were made on the must (Table 24):

TABLE 24

| | Control | Treated | Desirable |
|---|---|---|---|
| pH | 3.28 | 3.30 | 3.3-3.5 |
| TA | 0.92 | 0.85 | 0.7-0.75 |
| Brix | 17.4 | 18.7 | 20-22 |

These results indicate the grapes from the treated vines are riper than those of the untreated vines. Observation of the grapes themselves indicated that the untreated grapes were, on average, lighter in color, some with a transparent pinkish/purple/green tint, indicative of grapes just past veraison, whereas the treated grapes were dark purple on average and opaque, typical of fully or nearly fully ripened grapes.

Tasting of these grapes revealed the treated grapes to have a fuller fruitier taste typical of ripe Cabernet Sauvignon, whereas the untreated grapes did not have the full fruity taste. The untreated grapes had a green apple sour taste indicating probable a high malic/tartaric ratio unsuitable for good winemaking.

These grapes were crushed and destemmed in preparation for producing a wine from these grapes to demonstrate the difference in these grapes and to demonstrate the suitability of the treated grapes for winemaking. The grape grower was concerned that this treatment would affect the flavor of the wine, although at my suggestion he tasted treated grapes the day after application of YGP-GET and found no lingering taste or aroma.

The difference in the treated and untreated grapes is further demonstrated in the color of the must. The juice of the untreated grapes was light greenish/uncolored (somewhat like a white wine must) whereas the must from the treated grapes was a pinkish color typical of ripe Cabernet Sauvignon grapes immediately after crushing.

These results indicate that YGP-GET is efficacious in late summer vineyard treatment by killing and stopping Downy Mildew re-infection, in at least the short term.

Further research into the long term efficacy of the YGP-GET in controlling downy mildew would be useful, but the results presented show that YGP-GET is a useful treatment.

Late onset Downy Mildew can completely ruin a crop and there are currently no effective treatments which can be applied shortly before harvest and that retain their ability to provide protection. The great strength of YGP-GET is the ability to provide a quick kill and maintain this efficacy over a longer time than other contact fungicides.

There are a number of anti-fungals in this market which have an established track record against Downy Mildew, but all need some time after application before the crop can be harvested. Some treatments (like sulfur containing products) cannot be used if the temperature rises above 85° F. Phytotoxicity of copper containing fungicides is also significant depending on the variety of grape. Contact fungicides do not have a long term effect so a second application of a longer active fungicide is often needed, but may be restricted by relevant regulation (e.g. PHI or REI).

Many conventional treatments for Downy Mildew have a restricted reentry (REI and or PHI) which means the grower cannot apply the treatment in fear that he will apply something like Mancozeb, which has a PHI of 66 days; the grower would then be unable to harvest his grapes at peak maturity.

Downy Mildew is implicated as the primary cause of the many poor wines being produced east of the Mississippi. YGP-GET could allow affected grapes to ripen properly and be picked at peak maturity in this rapidly growing industry.

Advantageously YGP-GET should be eligible for approval by the various "organic" committees (many self-appointed) that this product is suitable for use on grapes grown under "organic" guidelines. This opens another niche in a rapidly growing market segment in the US and worldwide.

EXAMPLE 22

In Vitro Assessment of the Fungicidal Properties of Encapsulated and Non-Encapsulated Terpenes Further tests were conducted to assess the 31 non-encapsulated terpene preparations set out in Example 15 and preparations 16 and 22 encapsulated in glucan particles.

To conduct these assays, 20,000 spores were placed in ⅓ strength potato dextrose broth (PDB) and sufficient quantities of selected terpene formulations were added to give concentrations ranging from 10 to 1000 ppm. These test materials were placed in separate sterile capped Eppendorf tubes with *Botrytis cinerea* (B.c.) spores, incubated for 24 hr, then the spores were recovered by centrifugation, and the terpene solutions were discarded. The spores/biomass were rinsed with sterile water, centrifuged again and then taken back up in 300 µl of ⅓ strength PDB and transferred to 96 well plates. The optical density of the surviving spores growing into mycelia was measured over time. Fungicidal activity is defined as total killing of 20,000 spores after 24 hours terpene exposure, as evidence by the absence of mycelial growth.

The results suggest that certain formulations were not fungicidal at a statistically significant level under the present test conditions (results not shown). These were:

1, 2, 4, 5, 6, 8, 9, 11, 12, 14, 15, 17, 18, 19, 20, 21, 23, 24, 25, 27, 28, 29, 30. Refer to Example 15 (Table 17) for details of the compositions.

The minimum inhibitory concentration for the most effective compounds is set out in Table 26.

TABLE 25

| Material | Minimum inhibitory concentration (ppm) | Material | Minimum inhibitory concentration (ppm) |
|---|---|---|---|
| 3 | <1000; >750 | 7 | <1000; >750 |
| 10 | <1000; >500* | 13 | <1000; >750 |
| 16 | <1000; >750 | 22 | <750; >500 |
| 26 | <1000; >750 | 31 | <1000; >750 |

*In different tests, the lowest concentration that gave no growth was either 500 or 750 ppm.

Comparative Testing of Compounds in Water and Encapsulated in Hollow Glucan Particles.

Samples of formulations 16 (geraniol, eugenol and thymol) and 22 (eugenol, thymol and citral) encapsulated in hollow glucan particles were prepared in accordance with techniques previously described. The fungicidal properties were then assessed for encapsulated and non-encapsulated formulations using the protocol previously described for the non-encapsulated formulations.

The results were quite different with encapsulated terpene formulations as compared with the terpenes suspended in water, as shown in FIG. 24.

The minimum effective concentration is shown below in Table 26.

TABLE 26

| Material | MIC in suspension | MIC in yeast particles |
|---|---|---|
| 16 | <1000, >750 | <100, >250 |
| 22 | <750, >500 | <500, >250 |

Thus, the results with materials 16 and 22 are quite different when in aqueous suspension and when tested encapsulated in glucan particles. (Note: as mentioned later, there was some variability in the results with terpenes suspended in water, the experiment noted above is an example of this). The MIC values are composites from several trials. Importantly, the results with encapsulated terpene formulations do not suffer from the problems of variability associated with aqueous terpene suspensions. There have been five separate tests of terpenes suspended in water and three with the YPs.

Encapsulated terpene formulations are readily miscible with water and provide a slow release terpene formulation into the aqueous medium. This results in a longer exposure time of the spores to the terpenes.

Problems monitoring the non-encapsulated terpene formulations in suspension in the test media were encountered which may have affected the results in this regard.

EXAMPLE 23

In Vitro Evaluation of Encapsulated Terpenes for Powdery Mildew Control

The present study was conducted to determine the most effective terpene mixtures and the levels at which they are active in relation to powdery mildew.

31 terpenes or terpene mixtures encapsulated in yeast cell walls (YP-terpenes) were assessed; the codes used in relation to the particular compositions are set out in Table 17 of Example 15.

Protocol development was driven by the basic biology of the organism. The fungus is an obligate pathogen and so cannot be cultured other than on the leaves of grapes. We therefore inoculated plants ('Riesling' seedlings) and harvested conidia by washing infected leaves with copious sporulation.

A variation on the method used by Reuveni (2001; Can. J. Plant Pathol. 23:52-59) was employed. One to two leaves infected with *Uncinula necator* were placed in a sterile 50 mL plastic tube. Tween-20 (7.5 mL, 0.0005%) was added to the tube and the leaves were vigorously vortexed for 30 seconds. Conidia were counted using a Petroff-Hauser counting chamber and adjusted to $1-2\times10^5$ conidia/mL.

YP-terpenes were diluted to working solutions of 4000 ppm. Reactions took place in 600 μL siliconized eppendorf tubes and the final reaction volume was 60 μL. YP terpenes were diluted in the tube to give final concentrations of 100, 250, 500, 750 or 1000 ppm terpene. 40 μL of the conidia suspension was added to each tube and each tube was briefly vortexed. Water and test material 32 (particles only, no terpene) were included as controls. The test materials and conidia were incubated for 1-1.5 hr to provide sufficient contact time for inhibition of the spores without adversely affecting spore germination in the absence of the terpenes. This brief immersion was essential in order to permit adequate contact time with the terpenes since the terpene mixtures on the agar surface rapidly volatilized or were absorbed into the water.

Glass microscope slides were coated with 750 μL of 1.5% water agar. The glass slides were placed in germination boxes each containing a moist blotter. When attempts were made to directly place conidia and terpene mixtures directly on the agar, there were few effects of the terpenes, probably because of inadequate contact time. Lids were placed on each box and the materials were allowed to incubate for 48 h at room temperature on the benchtop. In some experiments, slides with different levels of terpenes were contained within the same box. This technique was found to permit erroneous results since the volatiles from slides with high levels of terpenes inhibited conidia on slides with lower levels of the materials. Therefore final data was taken from slides in boxes containing only one or two levels of the same test material.

After 48 h the slides were examined using a light microscope. Various settings of phase-contrast were used to obtain a sharp outline of each conidium. The YPs are many times smaller than the conidia and the two were easy to differentiate. At least 100 spores were assessed for germination per spot; if the number of observable spores was less than 100, every spore found was counted. Germ tube lengths of at least 10 germinated conidia were measured as well although this data was later not found to be very useful.

We also found that a small percentage of conidia are already germinated when they are washed off of the leaves. This is expected since powdery mildew conidia do not need free water to germinate and therefore can germinate at any time. We therefore set a maximum of 4% germination as our cutoff for fungicidal activity since this was the level frequently observed in the 0 time water controls. The age of the powdery mildew infection also resulted in some variability. Infections older than 3 weeks provided a lower level of overall germination in the controls (36% in water controls on agar slides) while younger infections gave much higher germination levels (around 70%). We observed all test materials several times, with data being collected at levels where inhibition occurred. 3 replicates per test were used.

Results:

Concentrations of materials ranged from 100 to 1000 ppm of terpene. Every test material was fungicidal at least at the highest concentration tested. Four classes of fungicidal efficacy were established for the 31 formulations. The terpene formulations and their grouping, based on minimal inhibitory dose (fungicidal), are provided below.

Group A (>100 ppm, <250 ppm): 7, 10, 22 and 30
Group B (>250, <500): 1, 2, 3, 7, 8, 13, 14, 16, 19, 20, 23-29 and 31
Group C (>500, <750): 4, 6, 9, 11, 15, 18 and 21
Group D (>750, <1000): 5, 12 and 17

The fungicidal dose was calculated based upon germination of powdery mildew conidia 48 hr after reaction as determined by microscopic observation. Since powdery mildew conidia germinate within 24 hr in the control, if germination did not occur with 48 hr, we considered that the spores were killed. In a few cases, we continued to observe for 72 hr or more, but no additional information was obtained.

EXAMPLE 24

In Vitro Evaluation of Encapsulated Terpenes for Downy Mildew Control

The present study was conducted to determine the most effective terpene mixtures and the levels at which they are active in relation to downy mildew.

*Plasmopara viticola*, the causal agent of downy mildew of grape, in vitro, was used in all studies. This was a wild type pathogenic strain obtained from colleagues at Cornell. The organism was maintained on leaves of seedlings obtained from 'Reisling' seeds.

Protocol development was driven by the basic biology of the organism. The fungus is an obligate pathogen and so cannot be cultured other than on the leaves of grapes. We therefore inoculated plants ('Riesling' seedlings) and harvested sporangia by gently washing infected leaves with water. We originally attempted to conduct assays by observing sporangia on glass slides with cover slips. However, we wanted to look at the slides over time and this method simply did not allow for this. The volumes used were too small for adequate assessment, the sporangia often would disintegrate from the pressure of the cover slip and the zoospores would encyst very quickly after release. A variation on the method used by Reuveni (2001; Can. J. Plant Pathol. 23:52-59) using depression slides was used. These slides do not require cover slips, the zoospores remain motile for many hours and the volumes used allowed for multiple assessments over time.

For all experiments, sporangia from 1-3 leaves infected with *Plasmopara viticola* were gently washed with sterile water into a beaker and counted using a Petroff-Hauser counting chamber. The concentration of sporangia was at least $1 \times 10^5$/ml.

YP-terpenes were diluted to working solutions of 4000 ppm. Reactions took place in 600 μL siliconized eppendorf tubes and the final reaction volume was 100 μL. YP-terpenes were diluted in the tube to give final concentrations of 10, 50, 100, 250 and 500 ppm terpene. Seventy-five μL of the sporangia suspension was added to each tube and gently mixed by pipetting the suspension up and down. Water and test material 32 (YP only, no terpene) were included as controls.

Assay #1—Closed Tubes

A preliminary assessment was done for all 31 test materials at 10, 50 and 100 ppm terpene to estimate the correct range of efficacy (i.e., no motile zoospores observed during the subsequent 8 hours). Once sporangia were observed to germinate and zoospores were observed in the controls (0.5-1 hour later), 15 μL were transferred to a glass depression slide from the tube one at a time and immediately observed using a light microscope. If motile zoospores were seen this concentration was not observed further. The slide was wiped clean. Every 2-3 hours, the process was repeated with new test material from the tube. At the end of 8 hours, the percent germination of the first 100 sporangia was determined. Samples were left at room temperature and observed again the next day. The criteria for cidal activity were (a) no greater sporangial germination than in 0 time controls (no more than 10%) and (b) no motile zoospores. The percentages of sporangial germination in the effective doses ranged from 1.8% to 6.7% compared to the controls of water (87%) and YP-32 (76%).

In this assay, the sporangia were in constant contact with the test materials in a sealed container.

Assay #2—One Hour Incubation

The assay system described above may not provide accurate data on cidal (i.e. lethal) concentrations since the absence of sporangial germination and motile zoospores are in the presence of the materials in closed tubes and the test materials are continually immersed in the test solutions. We cannot remove the cells from materials in solution because centrifugation is lethal to the sporangia and zoospores. Therefore, after 1 hr incubation in enclosed Eppendorf tubes, the test mixtures (40 μl) were transferred to depression slides. In this thin layer, the terpenes are expected to volatilize into the air and therefore cidal concentrations more accurately determined.

The slides were stored in germination boxes each containing a moist blotter. Every 2 hours the slides were inspected for motile zoospores. The concentration at which no motile zoospores were observed after 24 hours was considered the MIC in this assay.

Results:

Concentrations of test materials differed between assays but overall ranged from 10 to 500 ppm of terpene. Every test material was effective at least at the highest concentration tested in both assays. Three classes of Minimum Effective Concentrations (MICs) were established for the 31 terpenes for each test. The MIC for each test material is the concentration at which motile zoospores are absent.

The groups listed using the test numbers are as follows:
Assay #1—MICs—Closed Tubes (constant immersion in terpene suspensions)
Group A (<50 ppm): 3, 7, 11, 14, 17, 19, 25 and 26
Group B (>50, <100): 1, 4, 8, 10, 13, 16, 20, 22, 23, 27, 28, 30 and 31
Group C (>100, <250): 2, 5, 6, 9, 12, 15, 18, 21, 24 and 29
Assay #2—MICs—One Hour Incubation (terpenes dissipated by volatilization from thin layers)
Group A (<100 ppm): 4
Group B (>100, <250): 3, 7, 8, 10, 11, 13, 14, 16, 17, 19, 20 and 22-31
Group C (>250, <500): 1, 2, 5, 6, 9, 12, 15, 18 and 21

Thirty-one YP-terpene test materials were assessed for their abilities to inhibit the release of motile zoospores from sporangia of *Plasmopara viticola*. Two assays were conducted. In the first test we examined both sporangial germination and zoospore motility from materials incubated in closed tubes; in the second test we assessed only zoospore motility in depression slides after incubation in the closed tubes for only one hour.

The absence of motile zoospores is the clearest way to determine efficacy of the test materials and therefore was used as the definitive criterion. Zoospore motility is critical to infection by this pathogen. Inhibition of sporangial germination is the first step toward controlling downy mildew disease: if the sporangia remain intact, then the zoospores will not be released. Our data on sporangial germination supports the above MICs even though germination was never 0%. Some sporangia were already germinated when they were harvested from the leaves. The percent germination at 0 h (no zoospores observed) ranged from 6% to 16%.

In the first assay, the terpenes controlled the release of zoospores under ideal test conditions. Unmistakably, the test materials have a cidal effect on the downy mildew pathogen. However, Assay #2 provides a better test of lethality in situations, which also will occur on plant leaves, where the terpenes dissipate by volatility. Taken together, the two assays provide a complete assessment of the in vitro abilities of the YP-terpene materials to control the grape downy mildew pathogen.

EXAMPLE 25

In Vitro Evaluation of Encapsulated Terpenes for *Botrytis cinerea* Control 15 terpenes or terpene mixtures encapsulated in yeast cell walls were assessed. The formulations tested did not contain L-carvone.

*Botrytis cinerea* was used in all studies. The strain identification is B36 and was obtained from Cornell University. The organism was maintained on V8 agar at 25° C.

The protocol for this study combines aspects of a resazurin (Alamar Blue) assay with another protocol previously used with *B. cinerea*. The presence of the resazurin allows us to measure cidal levels of the terpenes in the presence of the yeast particles.

Spores of *Botrytis cinerea* were harvested in water and adjusted to a concentration of $1\times10^5$ spores/mL. YP terpenes were diluted to final concentrations of 100, 250 or 500 ppm in sterile 1.5 mL eppendorf tubes. 50 μL of the spore suspension and 375 μL of ⅓ strength PDB were added to the tubes. The suspensions were vortexed briefly and incubated at room temperature for 24 h. The inside of each tube was then scraped using a sterile toothpick to release hyphae from the walls.

Fungistatic Assay:

After 24 hr, two separate samples of 50 μl of the test suspensions were removed and placed in microtiter plate wells together with 30 μl of ⅓ strength PDB and 20 μL of 250 ppm resazurin. These mixtures were incubated overnight for 16-20 hours. Visual observations were then made. Those concentrations of YP and spore suspensions where the test mixtures remained purple were considered to be fungistatic. Resazurin suspensions are purple, but if reduced by biological activity the solutions become pink and then clear.

Fungicidal Assay:

After the two samples of the test suspensions were removed, the tubes were centrifuged at 3000 rpm for 10 min and the supernatant was discarded. The precipitate, which contained YPs, *Botrytis* spores and any germinated hyphae, was washed with 400 μL of water. The tubes were centrifuged again and the pellet was resuspended in 400 μl of sterile ⅓ PDB. To each tube, 150 μL of 250 ppm resazurin were added. The tubes were vortexed and incubated at room temperature overnight for 16-20 hours. Visual assessments were made and those concentrations of YP and spore suspensions where the test mixtures remained purple were considered to be fungicidal.

After 72 hours, visual assessments of the tubes were made again and purple samples were considered to be fungicidal.

Each well or tube was assigned a colour rating. No change in colour was rated 4; clear wells were rated 0. A rating of 3 or higher was considered static (little or no colour change) and only a rating of 4 (no change at all) was considered cidal.

Three replicates of each test material at each concentration were used for each experiment and each experiment was done twice.

Results:

Fungistatic Tests—Every test material was fungistatic at least at the highest concentration tested. The criterion for efficacy was at least 75% growth inhibition relative to the control. Ranges of efficacy were established for the 15 terpenes and are provided below.

Group A (<100 ppm): 3, 7, 10, 16, 19 and 26
Group B (>100, <250): 1, 2, 6, 11, 13, 17 and 22
Group C (>250, <500): 4 and 8

Fungicidal Tests—Visual assessment of colour change for fungicidal tests was measured twice: once after 16-20 h and once again after 72 h. After 20 h, all test materials were fungistatic at least at the highest concentration tested. However, after 72 h only a few of the samples were still considered fungicidal. The ranges of efficacy for each terpene at each time point are provided below.

After 16-20 hours:

Group A (>100, <250): 2, 3, 6, 7, 10, 13, 16, 17, 19, 22 and 26
Group B (>250, <500): 1, 4, 8 and 11

After 72 hours:

Group A (>100, <250): 7
Group B (>250, <500): 1, 3, 10, 13, 16, 19, 22 and 26
Group C (>500): 2, 4, 6, 8, 11 and 17

Composite Ratings

Each range of efficacy was assigned a rating (Group A=1, B=2 and C=3). The following tables (Tables 27 to 29) show the ratings for each test and the overall ratings for each YP terpene. The lower the number, the better the efficacy.

TABLE 27

| Ranges of Efficacy and Ratings for Each Test | | | | | | | |
|---|---|---|---|---|---|---|---|
| No. | CODE | Static | Rating | 16-20 h | Rating | 72 h Cidal | Rating |
| 1 | G | >100, <250 | 2 | >250, <500 | 2 | >250, <500 | 2 |
| 2 | E | >100, <250 | 2 | >100, <250 | 1 | >500 | 3 |
| 3 | T | <100 | 1 | >100, <250 | 1 | >250, <500 | 2 |
| 4 | C | >250, <500 | 3 | >250, <500 | 2 | >500 | 3 |
| 6 | GE | >100, <250 | 2 | >100, <250 | 1 | >500 | 3 |
| 7 | GT | <100 | 1 | >100, <250 | 1 | >100, <250 | 1 |
| 8 | GC | >250, <500 | 3 | >250, <500 | 2 | >500 | 3 |
| 10 | ET | <100 | 1 | >100, <250 | 1 | >250, <500 | 2 |
| 11 | EC | >100, <250 | 2 | >250, <500 | 2 | >500 | 3 |
| 13 | TC | >100, <250 | 2 | >100, <250 | 1 | >250, <500 | 2 |
| 16 | GET | <100 | 1 | >100, <250 | 1 | >250, <500 | 2 |
| 17 | GEC | >100, <250 | 2 | >100, <250 | 1 | >500 | 3 |
| 19 | GTC | <100 | 1 | >100, <250 | 1 | >250, <500 | 2 |
| 22 | ETC | >100, <250 | 2 | >100, <250 | 1 | >250, <500 | 2 |
| 26 | GETC | <100 | 1 | >100, <250 | 1 | >250, <500 | 2 |

TABLE 28

| Ratings for Each Test and Composite Scores | | | | | |
|---|---|---|---|---|---|
| No. | CODE | Static | 16-20 h Cidal | 72 h Cidal | Composite |
| 1 | G | 2 | 2 | 2 | 6 |
| 2 | E | 2 | 1 | 3 | 6 |
| 3 | T | 1 | 1 | 2 | 4 |
| 4 | C | 3 | 2 | 3 | 8 |
| 6 | GE | 2 | 1 | 3 | 6 |
| 7 | GT | 1 | 1 | 1 | 3 |
| 8 | GC | 3 | 2 | 3 | 8 |
| 10 | ET | 1 | 1 | 2 | 4 |
| 11 | EC | 2 | 2 | 3 | 7 |
| 13 | TC | 2 | 1 | 2 | 5 |
| 16 | GET | 1 | 1 | 2 | 4 |
| 17 | GEC | 2 | 1 | 3 | 6 |
| 19 | GTC | 1 | 1 | 2 | 4 |
| 22 | ETC | 2 | 1 | 2 | 5 |
| 26 | GETC | 1 | 1 | 2 | 4 |

TABLE 29

| Ratings of YP Terpenes from Most Effective to Least Effective | | |
|---|---|---|
| NO. | CODE | Composite |
| 7 | GT | 3 |
| 3 | T | 4 |
| 10 | ET | 4 |
| 16 | GET | 4 |
| 19 | GTC | 4 |
| 26 | GETC | 4 |
| 13 | TC | 5 |
| 22 | ETC | 5 |
| 1 | G | 6 |

TABLE 29-continued

| Ratings of YP Terpenes from Most Effective to Least Effective | | |
|---|---|---|
| NO. | CODE | Composite |
| 2 | E | 6 |
| 6 | GE | 6 |
| 17 | GEC | 6 |
| 11 | EC | 7 |
| 4 | C | 8 |
| 8 | GC | 8 |

The 8 most effective test materials have thymol (T) either alone or as a mixture component.

Discussion:

In previous in vitro studies, YP terpene test materials that contained L-carvone provided minimal effectiveness in controlling important plant pathogens. The 16 test materials that contained this component were therefore excluded.

Resazurin was included as an indicator dye. As *Botrytis* degrades resazurin a colour change from purple to pink to clear occurs. For the fungistatic assays, samples were transferred to 96-well microtiter plates and reacted with resazurin for 16-20 h before visual assessment of colour change. After centrifugation and washing, the remaining material in the tubes was reacted with resazurin to provide fungicidal assessments.

Test material YP-7 was the most effective sample in each test. YP-7 is the most effective material at controlling powdery mildew, in vitro, as well.

Conclusions:

All YP test materials were fungistatic against *Botrytis cinerea* at least at 500 ppm. After 16-20 h, all materials were considered to be fungicidal at least at 500 ppm. However, after 72 h, only 10 test materials were still considered to be fungicidal.

The most effective ones were fungicidal between 250 and 500 ppm.

EXAMPLE 26

In Vitro Evaluation of Encapsulated Terpenes for Control of Plant Bacteria

All three of the bacteria tested are Proteobacteria and are Gram-negative. They have an outer membrane mainly composed of lipopolysaccharides. *Erwinia amylovora* is in the family Enterobacteriaceae. Other bacteria in this family include *Salmonella* spp., *Escherichia coli*, and *Serratia marcescens*. *Pseudomonas syringae* is in the family Pseudomonadaceae. Other important members of this family include *Pseudomonas aeruginosa* (an opportunistic pathogen). Closely related to *Xanthomonas campestris* pv. *phaseoli* are several important pathovars including those that infect rice and carrot. *Pseudomonas* and *Xanthomonas* are very closely related.

During the 20th century, introductions of infested plant material served to establish *E. amylovora* in Europe, the Middle East, and New Zealand. *E. amylovora* causes fire blight in apple and in pear. In 1995, fire blight was first observed in the Po River Valley of northern Italy, which is the largest pear production area in the world. Since 1995, the Italian government has destroyed 500,000 pear trees in an attempt to eradicate *E. amylovora* (http://www.apsnet.org/education/LessonsPlantPath/FireBlight/HISTORY.HTM).

Common bean and halo blights are one of the most economically important and widespread diseases of dry and snap beans. The US, Canada and Colombia are some of the largest growers of these beans. Most management strategies involve planting only certified pathogen-free seed, rotating crops and making weekly chemical sprays (http://www.ip-genetics.com/commonbean.asp).

Methodology:

*Erwinia amylovora* (strain Ea273; fire blight of apple), *Pseudomonas syringae* pv. *phaseolicola* (strain Pph MF; halo blight of bean) and *Xanthomonas campestris* pv. *phaseoli* (strain Xph XPW; common blight of bean) were used in this study. These strains were obtained from Cornell University.

Cultures—All three bacteria were cultured on LB (Luria-Bertani) plates (Sambrook et al., 1989) at 28° C. Starter cultures (50 mL LB broth) were inoculated from plates and grown overnight (170 rpm, 28° C.). One mL of starter culture was transferred to a new 50 mL LB broth flask and grown under the same conditions until the stationary phase was reached. Cultures were read at 620 nm for optical density (OD) and then diluted with LB broth to give 105-106 cells/mL. This diluted material was used to inoculate the wells in the microtiter plate assays.

Bacteriostatic Assays:

The plate assays were conducted using LB broth as the growth medium. YP-Terpene test materials were diluted in the plate to give a range of 7.8 to 1000 ppm (Al terpene). Diluted bacteria were added to each well to give a final well volume of 200 µL. Control wells did not contain any YP-terpenes. Plates were read at 620 nm for initial measurements (initial OD) and incubated at 28° C. for two days.

After two days, the plates were read again at 620 nm (final OD). Final OD minus initial OD (delta OD) gives the change in growth over time. The criterion for efficacy was at least 75% inhibition of growth relative to the control. Therefore, the delta OD in test wells had to be less than 25% of the growth in the control wells in order to be considered effective at controlling the bacteria.

Bactericidal Assays:

After the bacteriostatic assays were completed, the plates were centrifuged at 2000 rpm for 10 minutes. The supernatant was removed and 100 µL of fresh LB broth were added to each well. The plates were read at 620 nm (initial OD), incubated at 28° C. for 3-4 days and read again at 620 nm (final OD). Effective concentrations provided at least 75% growth inhibition relative to the control.

Two replicates were used for each YP-terpene and both assays (static and cidal) were conducted three times for each bacterium.

Results:

Bacteriostatic Assay—For all three bacteria, every test material was bacteriostatic at least at the highest concentration tested. The assay ran for 48 hours. The criterion for efficacy was at least 75% growth inhibition relative to the control. Ranges of efficacy were established for the 31 terpenes and are provided below.

TABLE 30

| Bacteriosatic Results | | |
|---|---|---|
| Pathogen | Static MIC (ppm) | YP-Terpene |
| *Erwinia amylovora* | >15.625, <31.25 | 3, 7, 13, 16, 19, 20, 22, 24, 27 |
| | >31.25, <62.5 | 6, 8, 9, 10, 14, 17, 18, 21, 2326, 28, 29, 31 |
| | >125, <250 | n/a |
| | >250, <500 | 5 |

TABLE 30-continued

| Bacteriosatic Results | | |
|---|---|---|
| Pathogen | Static MIC (ppm) | YP-Terpene |
| *Pseudomonas syringae* | >125, <250 | 13, 14, 16, 22, 30 |
| | >250, <500 | 1-4, 6-12, 15, 17-20, 23-29, 31 |
| | >500, >1000 | 5, 21 |
| *Xanthomonas campestris* | >31.25, <62.5 | 3, 14 |
| | >31.25, <62.5 | 1, 2, 6, 7, 9, 10, 13, 16, 23, 25-28, 30 |
| | >125, <250 | 4, 8, 11, 12, 15, 18-20, 22, 24, 29, 31 |
| | >250, <500 | 5, 17, 21 |

Bactericidal Assay—A large number of terpene formulations were not effective at killing the bacteria at the highest concentration tested. Ranges of efficacy were established for the 31 terpenes and are provided below in Table 31.

TABLE 31

| Bactericidal Assay Results | | |
|---|---|---|
| Pathogen | Cidal MIC (ppm) | YP-Terpene |
| *Erwinia amylovora* | >250, <500 | 3, 7, 9, 10, 11, 13, 14, 16 |
| | >500, >1000 | 1, 2, 6, 8, 15, 19, 22, 26 |
| | 1000+ | 4, 5, 12, 17, 17, 20, 21, 23, 2425, 27-31 |
| *Pseudomonas syringae* | >500, >1000 | 3, 5, 7, 10, 13, 19, 26 |
| | 1000+ | 1, 2, 4, 6, 8, 9, 11, 12, 14-18, 20-25, 27-31 |
| *Xanthomonas campestris* | >250, <500 | 2, 13 |
| | >500, >1000 | 4, 7, 8, 10, 11, 14, 15, 19, 20, 22, 28 |
| | 1000+ | 1, 3, 5, 6, 9, 12, 16, 17, 18, 2123-27, 29-31 |

In each test, *Erwinia* was the pathogen most sensitive to the YP-terpene formulations followed by *Xanthomonas* and then *Pseudomonas*.

Ratings were assigned to each YP-terpene for each assay for each bacterium. The lower the rating number, the better the efficacy of the test material. The static and cidal ratings were multiplied to give a combination score. This number indicates how well the YP-terpene controlled each bacterium. The three combination scores (one for each bacterium) were added to give a composite score, which indicates YP-terpene efficacy across all three bacteria. Table 32 lists the YP-terpenes in order of efficacy based on the composite (overall) score along with the composition of each test material.

TABLE 32

| Overall Bacterial Control Composite Scores | | |
|---|---|---|
| YP Code | Composite Score | Terpenes |
| YP-13 | 4 | TC |
| YP-3 | 6 | T |
| YP-14 | 6 | TL |
| YP-7 | 7 | GT |
| YP-10 | 8 | ET |
| YP-16 | 9 | GET |
| YP-19 | 10 | GTC |
| YP-22 | 10 | ETC |
| YP-2 | 12 | E |
| YP-9 | 12 | GL |
| YP-26 | 12 | GETC |
| YP-11 | 13 | EC |
| YP-20 | 13 | GTL |

TABLE 32-continued

Overall Bacterial Control Composite Scores

| YP Code | Composite Score | Terpenes |
|---|---|---|
| YP-27 | 13 | ETCL |
| YP-6 | 14 | GE |
| YP-8 | 14 | GC |
| YP-28 | 14 | GTCL |
| YP-1 | 16 | G |
| YP-15 | 16 | CL |
| YP-23 | 16 | ETL |
| YP-24 | 16 | ECL |
| YP-30 | 17 | GETL |
| YP-4 | 19 | C |
| YP-18 | 19 | GEL |
| YP-25 | 19 | TCL |
| YP-29 | 19 | GECL |
| YP-31 | 19 | GETCL |
| YP-12 | 22 | EL |
| YP-17 | 22 | GEC |
| YP-21 | 24 | GCL |
| YP-5 | 30 | L |

Discussion:

The 8 best YP-terpene formulations for controlling these bacteria each contain thymol. Most combinations that contain L-carvone are very poor at controlling these bacteria.

Summary of Results of Examples 23 to 26

Certain combinations of encapsulated terpenes showed particular efficacy against certain types of plant pathogens. These combinations were observed to be:

1. For all organisms, the most effective compositions are 7 (Geraniol and Thymol), with 10 (Eugenol and Thymol), and 13 (Thymol and Citral) a close second.

2. 7 (Geraniol and Thymol) is the most effective overall for control of fungi/oomycetes.

3. 13 (Thymol and Citral) is the most effective overall for bacteria.

4. Combination 10 (Eugenol and Thymol) is highly effective against both fungi and bacteria.

5. In the next efficacy grouping are 3 (Thymol), 19 (Geraniol, Thymol and Citral), and 22 (Eugenol, Thymol, & Citral).

6. The fourth ranked group consists of 16 (Geraniol, Eugenol, & Thymol) and 26 (Geraniol, Eugenol, Thymol & Citral).

7. For downy mildew specifically, 4 (C) is highly effective but it is not in the top rank for anything else.

These results indicate that four terpenes citral, eugenol, geraniol and thymol alone or in combination, especially when encapsulated in yeast glucan particles exhibit strong anti-bacterial and antifungal activity. In most cases is the presence of thymol is significant.

Tables 33 to 35 summarise the rankings of the performance of the various formulations.

TABLE 33

Fungal/Oomycete Summary

| No | Content | B.c. | Powdery | Downy | Composite | Rank |
|---|---|---|---|---|---|---|
| 7 | GT | 1 | 1 | 2 | 4 | 1 |
| 3 | T | 2 | 2 | 2 | 6 | 3 |
| 10 | ET | 2 | 1 | 2 | 5 | 2 |
| 16 | GET | 2 | 2 | 2 | 6 | 3 |
| 19 | GTC | 2 | 2 | 2 | 6 | 3 |
| 26 | GETC | 2 | 2 | 2 | 6 | 3 |
| 13 | TC | 2 | 2 | 2 | 6 | 3 |

TABLE 33-continued

Fungal/Oomycete Summary

| No | Content | B.c. | Powdery | Downy | Composite | Rank |
|---|---|---|---|---|---|---|
| 22 | ETC | 2 | 1 | 2 | 5 | 2 |
| 1 | G | 2 | 2 | 3 | 7 | 4 |
| 2 | E | 3 | 2 | 3 | 8 | 4 |
| 6 | GE | 3 | 3 | 3 | 9 | 4 |
| 17 | GEC | 3 | 4 | 2 | 8 | 4 |
| 11 | EC | 3 | 3 | 2 | 8 | 4 |
| 4 | C | 3 | 3 | 1 | 7 | 4 |
| 8 | GC | 3 | 2 | 2 | 7 | 4 |

*Based on 72 hr cidal data

TABLE 34

Bacterial Summary

| Number | Content | E.a. cidal | Ps.p. cidal | X.cp. cidal | Sum | Ranking |
|---|---|---|---|---|---|---|
| 7 | GT | 1 | 1 | 2 | 4 | 2 |
| 3 | T | 1 | 1 | 3 | 5 | 3 |
| 10 | ET | 1 | 1 | 2 | 4 | 2 |
| 16 | GET | 1 | 2 | 3 | 6 | 4 |
| 19 | GTC | 2 | 1 | 2 | 5 | 3 |
| 26 | GETC | 2 | 1 | 3 | 6 | 4 |
| 13 | TC | 1 | 1 | 1 | 3 | 1 |
| 22 | ETC | 2 | 2 | 2 | 6 | 4 |
| 1 | G | 2 | 2 | 3 | 7 | 5 |
| 2 | E | 2 | 2 | 1 | 5 | 3 |
| 6 | GE | 2 | 2 | 3 | 7 | 5 |
| 17 | GEC | 3 | 2 | 3 | 8 | 6 |
| 11 | EC | 1 | 2 | 2 | 5 | 3 |
| 4 | C | 3 | 2 | 2 | 7 | 5 |
| 8 | GC | 2 | 2 | 2 | 6 | 4 |

TABLE 35

Combination Ranking of Fungal and Bacterial

| Number | Content | Fungal/Oomycete Rank | Bacterial Rank | Composite Rank |
|---|---|---|---|---|
| 7 | GT | 1 | 2 | 3 |
| 3 | T | 3 | 3 | 6 |
| 10 | ET | 2 | 2 | 4 |
| 16 | GET | 3 | 4 | 7 |
| 19 | GTC | 3 | 3 | 6 |
| 26 | GETC | 3 | 4 | 7 |
| 13 | TC | 3 | 1 | 4 |
| 22 | ETC | 2 | 4 | 6 |
| 1 | G | 4 | 5 | 9 |
| 2 | E | 4 | 3 | 7 |
| 6 | GE | 4 | 5 | 9 |
| 17 | GEC | 4 | 6 | 10 |
| 11 | EC | 4 | 3 | 7 |
| 4 | C | 4 | 5 | 9 |
| 8 | GC | 4 | 4 | 8 |

EXAMPLE 27

Efficacy of Encapsulated Compositions Against Mites

Two-spotted spider mites, which feed on a variety of plants including tomatoes. The purpose of the present study was to conduct preliminary in planta experiments in a commercial greenhouse to determine the efficacy of two YP-terpene mixtures against two-spotted spider mites (TSSM, *Tetranychus urticae*) and foliar diseases (*Botrytis*) of tomato. Naturally occurring populations of two-spotted spider mites were used.

YP-4 (citral) and YP-22 (thymol, eugenol, citral) (16% terpene formulations) were used.

On 28 March, a double row of 68 tomato plants (*Lycopersicon esculentum* var. Trust) were transplanted at the 6 true-leaf stage onto black plastic mulch covering native soil; the trial was conducted using 'Trust' as the tomato variety—this variety is more susceptible to TSSM than other varieties such as 'Boa'. Plant spacing was 12-inch in-row, offset. The cooperating grower pruned and trellised the plants vertically to a single growing point. Blocks of two plants per treatment were flagged and randomized in the double row with 4 replicates. Two untreated plants separated all blocks. Terpene formulations YP-4 and YP-22 were applied at a rate of 4 ml/L to leaf wetness on the following days: May 11 (Note: all dates in this example are in 2005), June 2 and 15, and July 1 and 18. Control treatments were treated with water until leaf wetness on the same dates.

Yield data (fruit numbers and weights), disease incidence and percent foliage damage by TSSM were recorded every 1-2 weeks beginning on 27 May until the trial conclusion on 29 July.

Numbers of mites per square centimeter were also measured on July 25. Leaf samples were taken from each plant ca. 1.5 meters from the ground (lower) and ca. 2.5 meters from the ground (upper). Leaves were placed in moist paper bags to avoid drying. The underside of each leaf was examined microscopically and counts were made. Total numbers of living mites (actively moving and quiescent) were determined. Mites in a quiescent phase strike a characteristic pose that is easily distinguishable from dead mites. No distinction was made between females and males or between adults and juveniles.

This trial was in some respects was complicated by, two factors. First, in most tomato greenhouse production older senescing leaves are removed as plants grow. This reduces mite populations since a substantial amount of the mites are removed along with these older leaves. These older leaves were intentionally left on the plant as a measure to increase the severity of the test.

Second, one plant in the trial, which was one of the plants treated with YP-22 in the fourth replicate, became infected with a virus that caused severe malformation of the plant. It also had the surprising result of being extremely attractive to mites and conducive to mite replication. This led to a tremendous population boom of mites that surrounded this plant. The plant was removed from the trial about June 25 but the very high level of mites that derived from this virus infected plant spread to adjacent plots over time and skewed the results.

This very high mite population could not have been controlled by any product. Mite populations, even if knocked back, rebound very quickly. For this reason, the data reported here shows results over time on a rep-by-rep basis.

Early Fungal Disease

Figure 25:
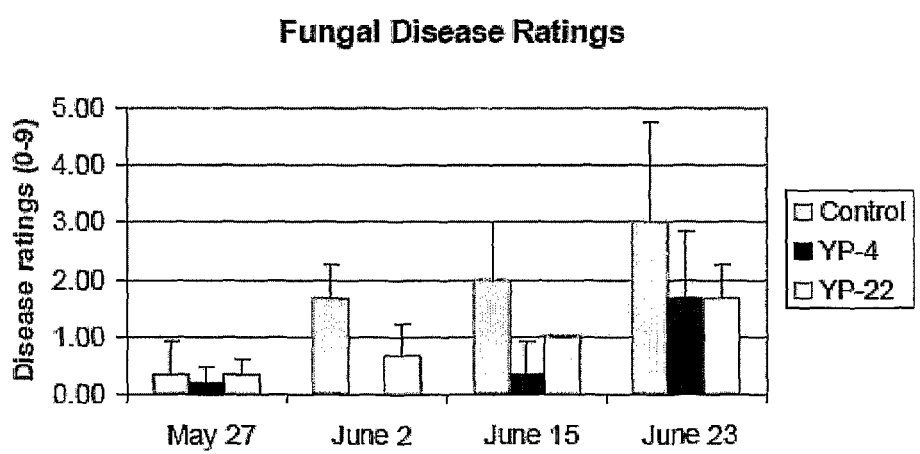
FIG. 25 shows fungal disease ratings for two yeast particle preparations as compared to a control preparation, which fungal disease was probably caused by *Botrytis cinerea*.

Early in the trials, there appeared to be a low level of fungal diseases that occurred, probably *Botrytis cinerea*. This disease was rated until the damage by mites became so overwhelming that no further ratings were possible. The results are shown below in FIG. 25.

Mite Damage Ratings

Figure 26A:
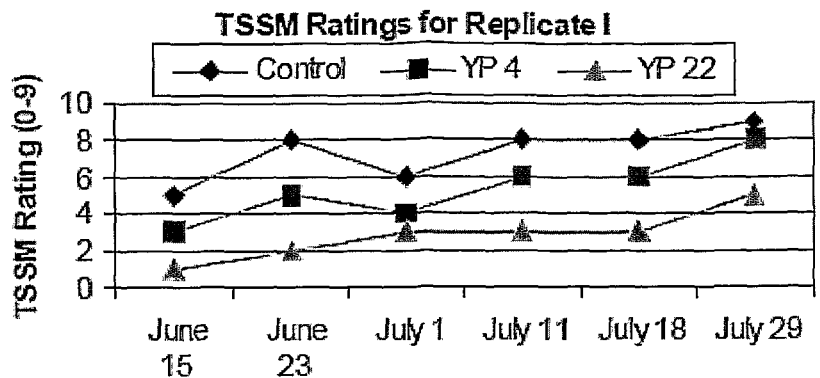
Figure 26B:
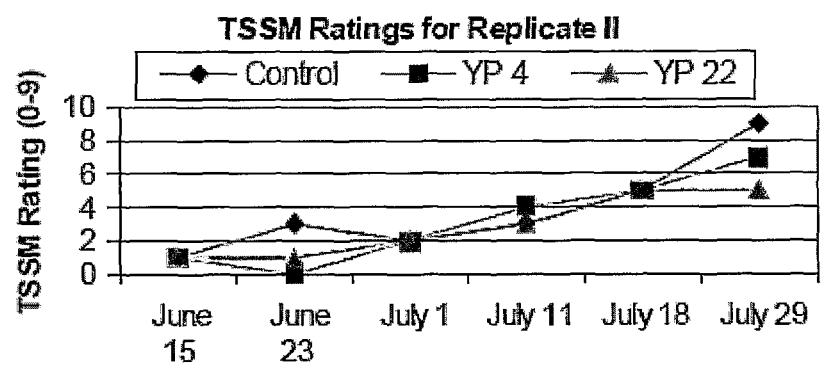
Figure 26C:
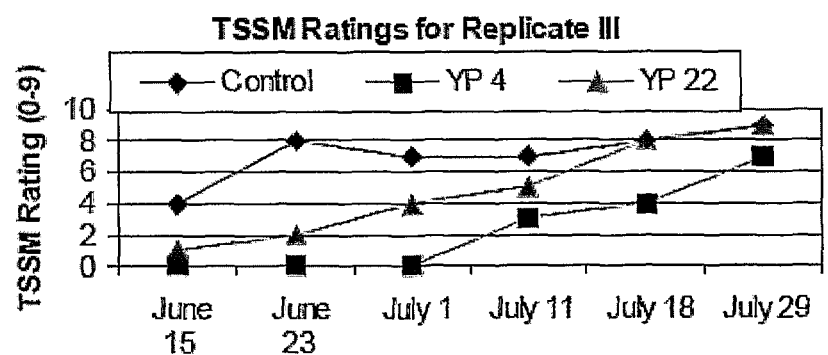
Figure 26D:
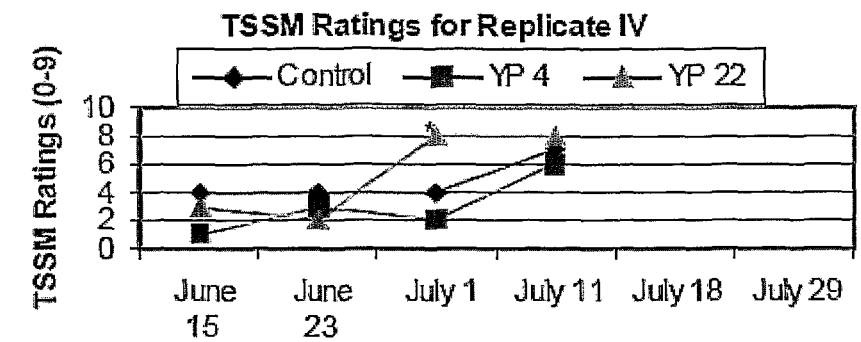

Given the virus plant issues, this discussion will focus on results by individual replicates, with a summary to follow. The results of the mite damage assessment are shown in FIGS. 26a-d. Replicate 1 (FIG. 26a) gave results very much as we would have hoped, with YP-22 substantially reducing two-spotted spider mite (TSSM) damage ratings over the entire course of the experiment. The treatments began on May 11 so the differences at the first TSSM ratings on June 15 are reasonable. Replicate 2 (FIG. 26b) followed a similar time course except for the fact that TSSM damage at the outset of the experiment was quite low. Replicate 4 (FIG. 26d) will be discussed next; its results affect replicate 3 (FIG. 26c). Until June 23, the TSSM ratings were consistent with the other replicates but increased tremendously by July 1 and was the greatest with YP-22. This no doubt occurred because the virus-infected plant was one that was treated with YP-22. This virus infection dramatically increased mite populations, either because it was very attractive or because it permitted rampant mite proliferation, or both. At any rate, the mite populations became very high. The mite population rapidly spread from the YP22-treated virus infected plant to the other plants in this replicate, and so by July 11, all the TSSM ratings were very high in replicate 4. To avoid infesting the rest of the house and experiment, the plants in replicate 4 were discarded after this time. In replicate 3, by July 1 the TSSM ratings began to climb and after this began to climb rapidly. Thus, no doubt replicate 3 received increasingly high pressure from the mites that began with the single plant in replicate 4. It is unlikely that any treatment could have contained the explosive population growth that arose from the virus-infected plant.

FIG. 27 is a photograph showing a comparison between a plant treated with YP-4 and a control. It can clearly be seen that treatment with the encapsulated terpene composition YP-4 results in a healthier and more productive plant.

Numbers of Mites

Mites were enumerated microscopically from the undersides of leaves taken from each plant ca. 1.5 meters (lower) from the ground and ca. 2.5 meters (upper) from the ground. The results are shown in Table 36.

TABLE 36

Comparison of mite infestation between treated and control plants

| Treatment | Plant Location | Av. Mites/m$^2$ | Std. Dev. | Max # | Min # |
| --- | --- | --- | --- | --- | --- |
| Control | lower | 10.86 | 11.06 | 27.55 | 0.00 |
| YP-4 | lower | 3.38 | 1.28 | 4.68 | 1.06 |
| YP-22 | lower | 0.36 | 0.34 | 0.84 | 0.04 |
| Control | upper | 9.59 | 22.11 | 54.71 | 0.00 |
| YP-4 | upper | 1.14 | 0.98 | 2.91 | 0.17 |
| YP-22 | upper | 0.85 | 1.35 | 3.21 | 0.00 |

These data indicate good mite control. There is great variation in the numbers of mites/leaf on the control plants, as would be expected for this pest. However, the maximum numbers with both treatments, especially the YP-22, treatment is substantially lower than the control.

Mites were controlled in this study especially by YP-22. However, where very high mite pressures occurred, YP-22 was insufficient in providing adequate control. It is likely that no acaricide would provide good control due to the very high mite populations in part of this study. It also is worthy of note that we applied the materials every two weeks and since mites have good rebound abilities, the YP test materials had residual activity; this was almost certainly provided as a result of encapsulation.

The results are extremely encouraging since the formulations to be used, the rate of application and the frequency of application were not optimised. It would no doubt be possible to improve efficacy by optimizing terpene mixtures, rates of application and frequency of application. Such optimisation would be a matter of trial and error to achieve.

Additionally, there are at least two types of adjuvants that can be used to increase efficacy. Silwet is an organosilicone surfactant that is added to pesticides as a tank mix. Good data indicate that this material increases activity of acaricides (reference available upon request). It can be used with all plants and is ready available. We have data also indicating that similar materials enhance efficacy of fungal disease control with biocontrol agents. Alternatively, Stirrup is a pheromone product that attracts mites to deposits of pesticides and enhances uptake of the material.

What is claimed is:

1. A composition for killing a plant bacterial infection caused by one or more of *Erwinia amylovora, Pseudomonas syringae* pv. *phaseolicola* and *Xanthomonas campestris* pv. *phaseoli* said composition comprising hollow yeast cell walls encapsulating 7.8 to 1000 ppm of a terpene component, the terpene component comprising a combination of thymol and citral; wherein the hollow yeast cell walls have a lipid content of 10% w/w or greater; and wherein the combination of thymol and citral has a greater bacteriostatic and bactericidal efficacy as it relates to *Erwinia amylovora, Pseudomonas syringae* pv. *phaseoficola* and *Xanthomonas campestris* pv. *phaseofi* as compared to thymol and citral separately.

2. The composition of claim 1 which comprises a terpene component comprising four or fewer terpenes.

3. The composition of claim 1 in which the terpene component consists of the specified terpenes.

4. The composition of claim 1 in which the terpene component is in suspension or solution in a solvent.

5. The composition of claim 4 in which the solvent is water.

6. The composition of claim 1 wherein the terpene component is in solution in water in the absence of a surfactant.

7. The composition of claim 1 wherein the terpene component is in association with a surfactant.

8. The composition of claim 1 in which the hollow yeast cell walls are a spray dried extract of *S. cerevisiae*.

9. The composition of claim 1 in which the encapsulated terpene component is associated with a surfactant.

10. The composition of claim 1 which comprises 1 to 99% by volume terpenes, 0 to 99% by volume surfactant and 1 to 99% hollow yeast cell walls.

11. The composition of claim 10 which comprises from about 10% to about 67% by volume terpenes, about 0.1 to about 10% by volume surfactant and from about 10 to about 90% hollow yeast cell walls.

12. The composition of claim 1 which comprises from about 500 to about 10,000 ppm hollow yeast cell walls, where the hollow yeast cell walls contain from about 1 to about 67% terpene component.

13. The composition of claim 1 in which the terpenes are at least food grade terpenes.

14. The composition of claim 1 which comprises an additional active compound.

15. The composition of claim 14 in which the additional active compound is an antimicrobial agent, an enzyme, an anti-fungal agent, an anti-bacterial agent, an insecticidal agent, an antimicrobial agent or an anaesthetic.

16. The composition of claim 1 comprising an antioxidant.

17. The composition of claim 1 in the form of a dry powder.

18. The composition of claim 1 in the form of a liquid.

19. The composition of claim 1 in the form of a pellet or tablet.

20. The composition of claim 19 in which the pellet or tablet contains a dispersal agent.

21. The composition of claim 1 in combination with an agriculturally or food or acceptable carrier or excipient.

22. The composition of claim 1 in combination with a chelating agent or inert gas.

* * * * *